(12) United States Patent
Thompson et al.

(10) Patent No.: US 9,340,511 B2
(45) Date of Patent: May 17, 2016

(54) PROCESS FOR MAKING ISOQUINOLINE COMPOUNDS

(71) Applicant: FIBROGEN, INC., San Francisco, CA (US)

(72) Inventors: Michael D. Thompson, Redwood City, CA (US); Jung Min Park, San Francisco, CA (US); Michael P. Arend, Foster City, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 14/414,879

(22) PCT Filed: Jul. 15, 2013

(86) PCT No.: PCT/US2013/050538
§ 371 (c)(1),
(2) Date: Jan. 14, 2015

(87) PCT Pub. No.: WO2014/014834
PCT Pub. Date: Jan. 23, 2014

(65) Prior Publication Data
US 2015/0175550 A1    Jun. 25, 2015

Related U.S. Application Data

(60) Provisional application No. 61/672,191, filed on Jul. 16, 2012.

(51) Int. Cl.
*C07D 217/26*    (2006.01)
(52) U.S. Cl.
CPC .................................... *C07D 217/26* (2013.01)
(58) Field of Classification Search
None
See application file for complete search history.

(56) References Cited

U.S. PATENT DOCUMENTS

| | | | |
|---|---|---|---|
| 3,989,704 A | 11/1976 | Houlihan et al. |
| 4,036,964 A | 7/1977 | Buckle et al. |
| 4,260,611 A | 4/1981 | Bartmann et al. |
| 4,559,403 A | 12/1985 | Bruderer et al. |
| 4,584,379 A | 4/1986 | Wagner |
| 4,673,682 A | 6/1987 | Konz et al. |
| 4,822,800 A | 4/1989 | Falotico et al. |
| 4,952,588 A | 8/1990 | Glamkowski et al. |
| 4,966,906 A | 10/1990 | Glamkowski et al. |
| 5,620,995 A | 4/1997 | Weidmann et al. |
| 5,658,933 A | 8/1997 | Weidmann et al. |
| 5,719,164 A | 2/1998 | Weidmann et al. |
| 5,726,305 A | 3/1998 | Weidmann et al. |
| 6,093,730 A | 7/2000 | Weidmann et al. |
| 6,319,931 B1 | 11/2001 | Kroemer et al. |
| 6,358,973 B1 | 3/2002 | Napoletano et al. |
| 6,358,976 B1 | 3/2002 | Wityak et al. |
| 6,369,053 B1 | 4/2002 | Yuan et al. |
| 6,762,318 B2 | 7/2004 | Kodra et al. |
| 6,777,425 B2 | 8/2004 | Burli et al. |
| 6,903,114 B2 | 6/2005 | Backstrom et al. |
| 7,208,601 B2 | 4/2007 | Mjalli et al. |
| 7,323,475 B2 | 1/2008 | Arend |
| 7,618,940 B2 | 11/2009 | Fourney |
| 7,629,357 B2 | 12/2009 | Arend |
| 7,696,223 B2 | 4/2010 | Deng |
| 7,863,292 B2 | 1/2011 | Arend |
| 7,928,120 B2 | 4/2011 | Arend |
| 8,017,625 B2 | 9/2011 | Arend |
| 8,124,582 B2 | 2/2012 | Guenzler-Pukall |
| 8,217,043 B2 | 7/2012 | Deng |
| 8,269,008 B2 | 9/2012 | Arend |
| 8,278,325 B2 | 10/2012 | Arend |
| 8,324,405 B2 | 12/2012 | Ho |
| 8,703,795 B2 | 4/2014 | Turtle |
| 8,759,373 B2 | 6/2014 | Arend |
| 8,765,956 B2 | 7/2014 | Arend |
| 8,883,823 B2 | 11/2014 | Witschi |
| 8,916,585 B2 | 12/2014 | Arend |
| 8,921,389 B2 | 12/2014 | Ng |
| 8,952,160 B2 | 2/2015 | Zhou |
| 9,115,085 B2 | 8/2015 | Witschi et al. |
| 2003/0153503 A1 | 8/2003 | Klaus et al. |
| 2003/0176317 A1 | 9/2003 | Guenzler-Pukall et al. |
| 2004/0204356 A1 | 10/2004 | Guenzler-Pukall et al. |
| 2004/0235082 A1 | 11/2004 | Fourney et al. |
| 2004/0254215 A1 | 12/2004 | Arend et al. |
| 2005/0020487 A1 | 1/2005 | Klaus et al. |
| 2006/0178316 A1 | 8/2006 | Klaus et al. |
| 2006/0178317 A1 | 8/2006 | Klaus et al. |
| 2006/0183695 A1 | 8/2006 | Klaus et al. |
| 2006/0199836 A1 | 9/2006 | Turtle et al. |
| 2006/0251638 A1 | 11/2006 | Guenzler-Pukall et al. |
| 2006/0258660 A1 | 11/2006 | Guenzler-Pukall et al. |
| 2006/0258702 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |

(Continued)

FOREIGN PATENT DOCUMENTS

CA    2134866 A1    5/1995
EP    0650960 A1    5/1995

(Continued)

OTHER PUBLICATIONS

Bruick et al., A Conserved Family of Proly-4-Hydroxylases That Modify HIF, *Science*, vol. 294, pp. 1337-1340, (2001).

(Continued)

*Primary Examiner* — Zinna Northington Davis
(74) *Attorney, Agent, or Firm* — Leanne C. Price; Sheppard Mullin Richter & Hampton LLP

(57) ABSTRACT

The present invention relates to methods for making isoquinoline compounds and the intermediate compounds achieved thereby. Such compounds can be used to prepare compounds and compositions capable of decreasing HIF hydroxylase enzyme activity, thereby increasing the stability and/or activity of hypoxia inducible factor (HIF).

48 Claims, No Drawings

(56) References Cited

U.S. PATENT DOCUMENTS

| | | |
|---|---|---|
| 2007/0004627 A1 | 1/2007 | Seeley et al. |
| 2007/0155784 A1 | 7/2007 | Arend et al. |
| 2007/0292433 A1 | 12/2007 | Seeley et al. |
| 2007/0293575 A1 | 12/2007 | Seeley et al. |
| 2010/0047367 A1 | 2/2010 | Deng et al. |
| 2010/0303928 A1 | 12/2010 | Arend et al. |
| 2010/0330199 A1 | 12/2010 | Zhou et al. |
| 2010/0331400 A1 | 12/2010 | Ho et al. |
| 2011/0212959 A1 | 9/2011 | Arend et al. |
| 2011/0305776 A1 | 12/2011 | Ho et al. |
| 2013/0178417 A1 | 7/2013 | Arend et al. |
| 2014/0024676 A1 | 1/2014 | Witschi et al. |
| 2014/0343094 A1 | 11/2014 | Arend |
| 2015/0031696 A1 | 1/2015 | Arend |
| 2015/0038528 A1 | 2/2015 | Ho |
| 2015/0038529 A1 | 2/2015 | Witschi et al. |
| 2015/0322015 A1 | 11/2015 | Witschi et al. |

FOREIGN PATENT DOCUMENTS

| | | |
|---|---|---|
| EP | 0650961 A1 | 5/1995 |
| EP | 0911340 A2 | 4/1999 |
| JP | H07-224039 A | 8/1995 |
| JP | H07-228571 A | 8/1995 |
| JP | H11302257 A | 11/1999 |
| JP | 2005-524612 A | 8/2005 |
| JP | 2006-514113 A | 4/2006 |
| JP | 2006-137763 A | 6/2006 |
| JP | 2006-527199 A | 11/2006 |
| WO | WO-96/18616 A1 | 6/1996 |
| WO | WO-01/58892 A1 | 8/2001 |
| WO | WO-02/070510 A2 | 9/2002 |
| WO | WO-02/074249 A2 | 9/2002 |
| WO | WO-02/074981 A2 | 9/2002 |
| WO | WO-02/100832 A1 | 12/2002 |
| WO | WO-02/101073 A2 | 12/2002 |
| WO | WO-03/053997 A2 | 7/2003 |
| WO | WO-2004/052285 A2 | 6/2004 |
| WO | WO-2004/108121 A1 | 12/2004 |
| WO | WO-2004/108681 A1 | 12/2004 |
| WO | WO-2005/007192 A2 | 1/2005 |
| WO | WO-2005/009962 A1 | 2/2005 |
| WO | WO-2005/011696 A1 | 2/2005 |
| WO | WO-2005/014533 A2 | 2/2005 |
| WO | WO 2010/056767 | 5/2010 |
| WO | WO-2013/013609 A1 | 1/2013 |
| WO | WO-2014/014834 A1 | 1/2014 |
| WO | WO-2014/014835 A2 | 1/2014 |
| WO | WO 2014/116849 | 7/2014 |

OTHER PUBLICATIONS

Cunliffe et al., Novel Inhibitors of Prolyl 4-Hydroxylase 3 Inhibition by the Substrate Analogue N-Oxaloglycine and Its Derivatives, *J. Med. Chem.*, vol. 35, pp. 2652-2658, (1992).

Duro et al., Sintesi Ed Attivita Farmacologica D1 Ammmino-E Dialchilamminoalchilammidi-D1 Derivati Della 3-Carbossi-4-Fenillisochinolina, *Ed. Sc.*, vol. 36, pp. 400-411, (1980) (Abstract in English).

Franklin et al., Approaches to the Design of Anti-Fibrotic Drugs, *Biochem. Soc. Trans.*, 19(4):812-815, (1991).

Guo et al., Selective Protection of 2',2'-Difluorodeoxycytidine (Gemcitabine), *J. Org. Chem.*, vol. 64, pp. 8319-8322, (1999).

International Search Report with Written Opinion for PCT/US2004/017773, dated Oct. 13, 2004.

International Search Report with Written Opinion for PCT/US2013/050539, dated Jul. 2, 2014.

Ivan et al., HIFα Targeted for VHL-Mediated Destruction by Proline Hydroxylation: Implications for O2 Sensing, *Science*, 292:464-468, (2001).

Jaakkola et al., Targeting of HIF-α to the von Hippel-Lindau Ubiquitylation Complex by O2-Regulated Prolyl Hydroxylation, *Science*, 292(5516):468-472, (2001).

Lando et al., Oxygen-Dependent Regulation of Hypoxia-Inducible Factors by Polyl and Asparaginyl Hydroxylation, Eur. J. Biochem, 270:781-790, (2003).

Richard et al., Nonhypoxic Pathway Mediates the Induction of Hypoxia-Inducible Factor 1α in Vascular Smooth Muscle Cells, J. Bio. Chm., 275:26765-26771, (2000).

Safran et al., HIF Hydroxylation and the Mammalian Oxygen-sensing Pathway, J. Clin. Invest., 111(6):779-783, (2003).

Sandau et al., Induction of Hypoxia-Inducible-Factor 1 by Nitric Oxide Is Mediated Via the PI 3K Pathway, Biochem. Biophys. Res. Commun., 278:263-267, (2000).

Sato et al., Stability and Physicochemical Properties of Viracept Tablets, Antibiotics and Chemotherapy, 14(9):1589-1592, (1998)—English Translation Not Available.

Sodhi et al., MAPK and Akt Act Cooperatively But Independently on Hypoxia Inducible Factor-1 α in rasV12 Unregulation of VEGF, *Biochem. Biophys. Res. Commun.*, 287:292-300, (2001).

Tacchini et al., Hepatocyte Growth Factor Signaling Stimulates Hypoxia Inducible Factor-1 (HIF-1) Activity in HepG2 Hepatoma Cells, *Carcinogenesis*, 22:1363-1371, (2001).

Wu et al., Regulatory Perspectives of Type II Prodrug Development and Time-Dependent Toxicity Management: Nonclinical Pharm/Tox Analysis and the Role of Comparative *Toxicology*, Toxicology, 236, pp. 1-6, (2007).

International Search Report for PCT Application No. PCT/US2013/050538 dated Sep. 17, 2013.

Written Opinion for PCT Application No. PCT/US2013/050538 dated Jan. 16, 2015.

PROCESS FOR MAKING ISOQUINOLINE COMPOUNDS

CROSS REFERENCE TO RELATED APPLICATION

This application is a U.S. National Stage Application under 35 U.S.C. §371 of International Application No. PCT/US2013/050538, filed Jul. 15, 2013, which claims the benefit under 35 U.S.C. §119(e) of United States Provisional Application No. 61/672,191, filed Jul. 16, 2012, the entirety of which are incorporated herein by reference.

BACKGROUND

1. Field

The present invention relates to methods for making isoquinoline compounds and the intermediate compounds achieved thereby.

2. State of the Art

Isoquinoline compounds are known to be effective in the treatment and prevention of conditions and disorders associated with HIF, including anemia and tissue damage caused by ischemia and/or hypoxia (see, e.g., Robinson et al. (2008) Gastroenterology 134(1): 145-155; Rosenberger et al. (2008) Nephrol Dial Transplant 23(11):3472-3478). Specifically, the compounds and methods disclosed herein can be used as, or in the preparation of, isoquinoline compounds for inhibiting HIF hydroxylase activity, thereby increasing the stability and/or activity of hypoxia inducible factor (HIF), which can then be used to treat and prevent HIF-associated conditions and disorders.

To date, a number of synthetic routes for the preparation of substituted isoquinoline compounds have been published. In 1966, Caswell et al. (*Heterocyclyl Chem* 1966, (3), 328-332) reported the synthesis of 4-hydroxy-3-carbomethoxy-1(2H)-isoquinoline, and the 6- and 8-methoxy substituted derivatives thereof, via the Gabriel-Coleman rearrangement of phthalimidoacetate with sodium in methanol, preferably at high temperatures (105° C.) in a sealed reaction vessel. Whereas such methods did provide an excess of one regioisomer, the substitution was dictated by the electronic nature of the substituent, not the desire of the chemist.

In 1978, Suzuki et al. (*Synthesis* 1978 (6), 461-462) reported the synthesis of 4-hydroxy-3-carbomethoxy-1(2H)-isoquinoline via the acid catalyzed ring opening and subsequent intramolecular cyclization of 4-methoxycarbonyl-1,3-oxazole, which was prepared from phthalic anhydride and methyl isocyanoacetate. Suzuki et al. also reported the synthesis of the nitro substituted 4-hydroxy-3-carbomethoxy-1 (2H)-isoquinoline, however, the methods disclosed therein provided a mixture of the 6- and 7-nitro isoquinoline compounds.

Weidmann et al. (U.S. Pat. No. 6,093,730) reported the synthesis of various substituted isoquinoline-3-carboxamides via chromatographic separation of the 4-hydroxy-3-carbomethoxy-1(2H)-isoquinoline isomers provided by the Caswell et al. synthesis, followed by hydrolysis of the methyl ester, activation of the corresponding acid to the acid halide, and condensation with glycine methyl ester.

Other methods for the preparation of substituted isoquinoline compounds have been reported in U.S. Pat. No. 7,629,357 and U.S. Pat. No. 7,928,120. U.S. Pat. No. 7,928,120 teaches the preparation of substituted cyanoisoquinoline compounds from an optionally substituted 2-methylbenzoic acid ester via reaction with a halogenating reagent to provide the corresponding 2-(halomethyl)benzoic acid ester, followed by reaction with a N-protected glycine ester, and finally cyclization/aromatization using a base and optionally an oxidizing agent. Such methods have an advantage over the documents described hereinabove in that the disclosed process affords only a single isomer of the 5-, 6-, 7-, or 8-substituted isoquinoline compounds. However, only halo and cyano substituents at the 1-position of the isoquinoline are provided. U.S. Pat. No. 7,629,357 discloses methods for the synthesis of various substituents at the 1-position of variously substituted isoquinoline compounds, including 1-methyl isoquinoline compounds. The 1-methyl isoquinoline compounds of U.S. Pat. No. 7,629,357 are prepared by first reacting the corresponding 1,4-dihydroxyisoquinoline compound with phosphorous oxychloride or phosphorous oxybromide to afford the 1-chloro or 1-bromoisoquinoline compound, followed by methylation using either trimethylboroxine with tetrakis(triphenylphosphine)palladium or an excess of n-butyllithium followed by methyliodide.

SUMMARY

The present invention relates to methods for synthesizing variously substituted isoquinoline compounds, and the intermediate compounds achieved thereby, safely and efficiently on a large scale. Specifically, the methods disclosed herein provide the desired 5-, 6-, 7-, or 8-substituted isoquinoline compound as a single regioisomer without the need for chromatographic separation, and do not utilize reagents such as phosphorous oxychloride, phosphorous oxybromide, n-butyllithium or trimethylboroxine, which can be unsafe and/or costly when used in a large scale.

Also provided are novel intermediate compounds achieved by the methods. The compounds disclosed herein can be used as, or in the preparation of, isoquinoline compounds for inhibiting HIF hydroxylase activity, thereby increasing the stability and/or activity of hypoxia inducible factor (HIF). Such compounds are useful for the treatment of disorders associated with ischemia and hypoxia, and for treatment of erythropoietin associated disorders, including inter alia, anemia (see, e.g., U.S. Pat. No. 7,629,357).

In one aspect, the present invention is directed to a method of making a compound of formula I or a stereoisomer or mixture of stereoisomers thereof:

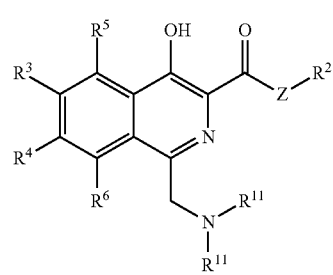

the method comprising contacting a compound of formula II:

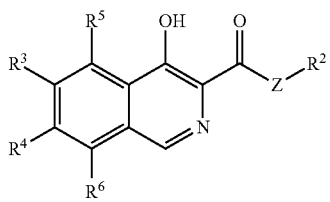

with a compound of formula III:

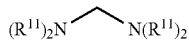

under reaction conditions sufficient to produce a compound of formula I; wherein Z is O, $NR^1$, or S;

$R^1$ is selected from the group consisting of hydrogen and alkyl;

$R^2$ is selected from the group consisting of hydrogen and alkyl which is unsubstituted or substituted with one or more substituents independently selected from the group consisting of cycloalkyl, heterocyclyl, aryl, and heteroaryl;

$R^3$ and $R^4$ are independently selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, $-S(O)_n-N(R^8)-R^8$, $-NR^8C(O)NR^8R^8$, and $-X^1R^8$;

where $X^1$ is oxygen, $-S(O)_n-$, or $-NR^9-$;

n is 0, 1, or 2;

each $R^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when $X^1$ is $-SO-$ or $-SO_2-$, then $R^8$ is not hydrogen; and $R^9$ is selected from the group consisting of hydrogen, alkyl, and aryl;

or $R^3$ and $R^4$ together with the carbon atoms pendent thereto, form a cycloalkyl, substituted cycloalkyl, heterocyclyl, substituted heterocyclyl, aryl, substituted aryl, heteroaryl, or substituted heteroaryl;

$R^5$ and $R^6$ are independently selected from the group consisting of hydrogen, halo, alkyl, substituted alkyl, alkoxy, substituted alkoxy, aryl, substituted aryl, heteroaryl, substituted heteroaryl and $-X^2R^{10}$;

where $X^2$ is oxygen, $-S(O)_n-$, or $-NR^{13}-$;

n is 0, 1, or 2;

$R^{10}$ is selected from the group consisting of alkyl, substituted alkyl, aryl, substituted aryl, heteroaryl, substituted heteroaryl, heterocyclyl and substituted heterocyclyl; and $R^{13}$ is selected from the group consisting of hydrogen, alkyl, and aryl;

or when $X^2$ is $-NR^{13}-$, then $R^{10}$ and $R^{13}$, together with the nitrogen atom to which they are bound, can be joined to form a heterocyclyl or substituted heterocyclyl group; and each $R^{11}$ is independently selected from alkyl, benzyl or aryl, or two $R^{11}$ together with the nitrogen atom to which they are attached form a 4-8 membered heterocyclyl or a heteroaryl.

In another aspect, the present invention is directed to a method of making a compound of formula IV or a stereoisomer or mixture of stereoisomers thereof:

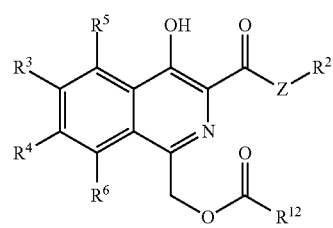

the method comprising contacting a compound of formula I:

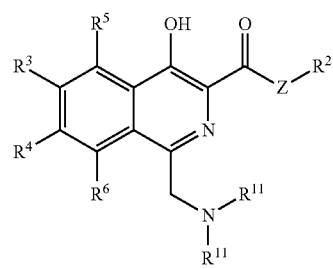

with one of the following:

(a) a compound of formula

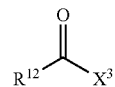

followed by a compound of formula

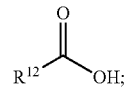

(b) a compound of formula $R^{12}-X^3$ followed by a compound of formula

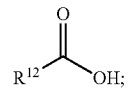

or (c) a compound of formula V:

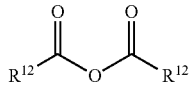

V under reaction conditions sufficient to produce a compound of formula IV; wherein $X^3$ is halo;

$R^{12}$ is selected from the group consisting of alkyl, aryl, heteroaryl, and heterocyclyl, or when two $R^{12}$ are present, two $R^{12}$ together with the carbon atom to which they are attached form a 4-8 membered heterocyclyl; and Z, $R^1$, $R^2$, $R^3$, $R^4$, $R^5$, $R^6$, $R^5$, $R^9$, $R^{10}$, $R^{11}$, $R^{13}$, n, $X^1$ and $X^2$ are as defined for formula I above.

In another aspect, the present invention is directed to a method of making a compound of formula VI or a stereoisomer or mixture of stereoisomers thereof:

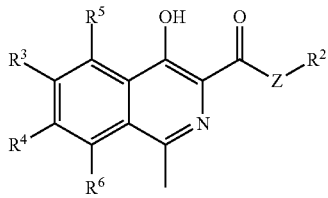

VI the method comprising converting a compound of formula IV:

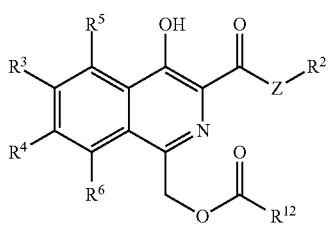

IV under reaction conditions sufficient to produce a compound of formula VI; wherein Z, $R^1$, $R^2$, $R^3$, $R^4$, $R^5$, $R^6$, $R^8$, $R^9$, $R^{10}$, $R^{11}$, $R^{13}$, n, $X^1$ and $X^2$ are as defined for formula I above; and $R^{12}$ is selected from the group consisting of alkyl, aryl, heteroaryl, and heterocyclyl.

In another aspect, the invention is directed to a compound of formula VIII:

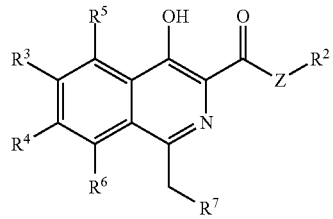

VIII wherein:
Z, $R^1$, $R^2$, $R^3$, $R^4$, $R^5$, $R^6$, $R^8$, $R^9$, $R^{10}$, $R^{11}$, $R^{13}$, n, $X^1$ and $X^2$ are as defined for formula I above;

$R^7$ is —N($R^{11}$)($R^{11}$) or —OC(O)$R^{12}$; and $R^{12}$ is selected from the group consisting of alkyl, aryl, heteroaryl, and heterocyclyl;

or a salt, ester, stereoisomer, or mixture of stereoisomers thereof;

provided that the compound is not 1-dimethylaminomethyl-4-hydroxy-7-phenylsulfanyl-isoquinoline-3-carboxylic acid butyl ester.

Additional embodiments of the invention are described throughout.

DETAILED DESCRIPTION

Before the compounds and methods are described, it is to be understood that the invention is not limited to the particular compounds, compositions, methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Definitions

It must be noted that as used herein, and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag.

The term "alkyl" refers to saturated monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like.

The term "substituted alkyl" refers to an alkyl group of from 1 to 10 carbon atoms, more particularly 1 to 5 carbon atoms, and having from 1 to 5 substituents, or 1 to 3 substituents, each of which substituents is independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic and —OSO$_2$—NR$^{40}$R$^{40}$, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently selected from hydrogen or alkyl. This group is exemplified by groups such as trifluoromethyl, benzyl, pyrazol-1-ylmethyl, etc.

The term "alkoxy" refers to the group "alkyl-O—," which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O-".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide", or the prefix "carbamoyl," "carboxamide," "substituted carbamoyl" or "substituted carboxamide", refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, or 2 to 4 carbon atoms, and having at least 1, or from 1 to 2 sites of vinyl (>C=C<) unsaturation. Such groups are exemplified by vinyl (ethen-1-yl), allyl, but-3-enyl and the like. This term includes both E (trans) and Z (cis) isomers as appropriate. It also includes mixtures of both E and Z components.

The term "substituted alkenyl" refers to alkenyl groups having from 1 to 3 substituents, or 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (trans) and Z (cis) isomers as appropriate. It also includes mixtures of both E and Z components.

The term "alkynyl" refers to acetylenic unsaturated monovalent hydrocarbyl groups having from 2 to 6 carbon atoms, or 2 to 3 carbon atoms, and having at least 1, or from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, or 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This group is exemplified by groups such as phenylethynyl, etc.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, or the R$^{41}$ groups can be joined together with the nitrogen atom to form a heterocyclic or substituted heterocyclic ring; provided that both R$^{41}$ groups are not hydrogen. This group is exemplified by phenylamino, methylphenylamino, and the like. This group is further exemplified by groups such as (ethanic acid-2-yl)amino, etc.

The term "acylamino" refers to the groups —$NR^{45}C(O)$alkyl, —$NR^{45}C(O)$substituted alkyl, —$NR^{45}C(O)$cycloalkyl, —$NR^{45}C(O)$substituted cycloalkyl, —$NR^{45}C(O)$alkenyl, —$NR^{45}C(O)$substituted alkenyl, —$NR^{45}C(O)$alkynyl, —$NR^{45}C(O)$substituted alkynyl, —$NR^{45}C(O)$aryl, —$NR^{45}C(O)$substituted aryl, —$NR^{45}C(O)$heteroaryl, —$NR^{45}C(O)$substituted heteroaryl, —$NR^{45}C(O)$heterocyclic, and —$NR^{45}C(O)$substituted heterocyclic where $R^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —$NR^{46}C(O)O$-alkyl, —$NR^{46}C(O)O$-substituted alkyl, —$NR^{46}C(O)O$-alkenyl, —$NR^{46}C(O)O$-substituted alkenyl, —$NR^{46}C(O)O$-alkynyl, —$NR^{46}C(O)O$— substituted alkynyl, —$NR^{46}C(O)O$-cycloalkyl, —$NR^{46}C(O)O$-substituted cycloalkyl, —$NR^{46}C(O)O$-aryl, —$NR^{46}C(O)O$-substituted aryl, —$NR^{46}C(O)O$-heteroaryl, —$NR^{46}C(O)O$-substituted heteroaryl, —$NR^{46}C(O)O$-heterocyclic, and —$NR^{46}C(O)O$-substituted heterocyclic where $R^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —$NR^{46}C(S)O$-alkyl, —$NR^{46}C(S)O$-substituted alkyl, —$NR^{46}C(S)O$-alkenyl, —$NR^{46}C(S)O$-substituted alkenyl, —$NR^{46}C(S)O$-alkynyl, —$NR^{46}C(S)O$-substituted alkynyl, —$NR^{46}C(S)O$-cycloalkyl, —$NR^{46}C(S)O$-substituted cycloalkyl, —$NR^{46}C(S)O$-aryl, —$NR^{46}C(S)O$-substituted aryl, —$NR^{46}C(S)O$-heteroaryl, —$NR^{46}C(S)O$-substituted heteroaryl, —$NR^{46}C(S)O$-heterocyclic, and —$NR^{46}C(S)O$-substituted heterocyclic where $R^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy," or the prefix "carbamoyloxy" or "substituted carbamoyloxy," refers to the groups —$OC(O)NR^{47}R^{47}$ where each $R^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each $R^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —$NR^{49}C(O)N(R^{49})_2$ where each $R^{49}$ is independently selected from the group consisting of hydrogen and alkyl.

The term "aminothiocarbonylamino" refers to the group —$NR^{49}C(S)N(R^{49})_2$ where each $R^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino (—C(=NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(=NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —$OS(O)_2$-alkyl, —$OS(O)_2$-substituted alkyl, —$OS(O)_2$-aryl, —$OS(O)_2$-substituted aryl, —$OS(O)_2$-heteroaryl, —$OS(O)_2$-substituted heteroaryl, —$OS(O)_2$-heterocyclic, —$OS(O)_2$-substituted heterocyclic, and —$OSO_2$—$NR^{51}R^{51}$, —$NR^{51}S(O)_2$—$NR^{51}$-alkyl, —$NR^{51}S(O)_2$—$NR^{51}$-substituted alkyl, —$NR^{51}S(O)_2$—$NR^{51}$-aryl, —$NR^{51}S(O)_2$—$NR^{51}$-substituted aryl, —$NR^{51}S(O)_2$—$NR^{51}$-hetero aryl, —$NR^{51}S(O)_2$—$NR^{51}$-substituted heteroaryl, —$NR^{51}S(O)_2$—$NR^{51}$-heterocyclic, —$NR^{51}S(O)_2$—$NR^{51}$-substituted heterocyclic, where each $R^{51}$ is independently selected from hydrogen or alkyl, wherein each of the terms is as defined herein. This group is exemplified by groups such as 4-fluorophenyl, 3-methoxyphenyl, 4-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 3,5-difluorophenyl, 4-methoxyphenyl, 3-cyanophenyl, 4-cyanophenyl, 4-phenoxyphenyl, 4-methanesulfonylphenyl, biphenyl-4-yl, etc.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl ester" refers to the groups —C(O)O-alkyl, —C(O)O-substituted alkyl, —C(O)O— alkenyl, —C(O)O-substituted alkenyl, —C(O)O-alkynyl, —C(O)O-substituted alkynyl, —C(O)O-cycloalkyl, —C(O)O-substituted cycloalkyl, —C(O)O-aryl, —C(O)O-substituted aryl, —C(O)O-heteroaryl, —C(O)O— substituted heteroaryl, —C(O)O-heterocyclic, and —C(O)O-substituted heterocyclic.

The term "cyano" refers to the group —CN.

The term "cycloalkyl" refers to a saturated or an unsaturated but nonaromatic cyclic alkyl group of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, or iodo.

The term "hydroxy" or "hydroxyl" refers to the group —OH.

The term "heteroaryl" refers to an aromatic ring of from 1 to 15 carbon atoms, or from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrimidinyl, pyrrolyl, pyrazolyl, indolyl, thiophenyl, thienyl, and furyl.

The term "substituted heteroaryl" refers to heteroaryl groups that are substituted with from 1 to 3 substituents selected from the same group of substituents defined for substituted aryl. This group is exemplified by groups such as 5-fluoro-pyridin-3-yl, 1-benzyl-1H-[1,2,3]triazol-4-yl, 5-bromo-furan-2-yl, trifluoromethyl-2H-pyrazol-3-yl, etc.

The term "heteroaryloxy" refers to the group —O-heteroaryl and "substituted heteroaryloxy" refers to the group —O-substituted heteroaryl.

The terms "heterocyclyl" and "heterocyclic" are used interchangeably herein. As used herein, the terms refer to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidinyl, pyrrolyl, imidazolyl, pyrazolyl, pyridinyl, pyrazinyl, pyrimidinyl, pyridazinyl, indolizinyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), piperidinyl, pyrrolidinyl, tetrahydrofuranyl, and the like.

The term "nitro" refers to the group —$NO_2$.

The term "oxo" refers to the atom (=O) or to the atom (=O).

The term "sulfonyl" refers to the group —$S(O)_2H$. The term "substituted sulfonyl" refers to the group —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-cycloalkyl, —$SO_2$-substituted cycloalkyl, —$SO_2$-cycloalkenyl, —$SO_2$-substituted cycloalkenyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclyl and substituted heterocyclyl are as defined herein. Substituted sulfonyl includes groups such as methyl-$SO_2$—, phenyl-$SO_2$—, and 4-methylphenyl-$SO_2$—.

The term "heterocyclyloxy" refers to the group —O-heterocyclic, and "substituted heterocyclyloxy" refers to the group —O-substituted heterocyclic.

The term "thio" or "mercapto" refers to the group —SH.

The term "alkylsulfanyl," "alkylthio," or "thioether" refers to the groups —S-alkyl where alkyl is as defined above.

The term "substituted alkylthio," "substituted alkylsulfanyl," or "substituted alkylthio" refers to the group —S-substituted alkyl where substituted alkyl is as defined above.

The term "cycloalkylthio" or "cycloalkylsulfanyl" refers to the groups —S-cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl, and "substituted arylthio" refers to the group —S-substituted aryl where aryl and substituted aryl are as defined above.

The term "heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic where heterocyclic, and substituted heterocyclic are as defined above.

The term "ester" refers to compounds as disclosed herein that include the group —$COOR^{54}$ where $R^{54}$ is alkyl, or substituted alkyl.

The term "amine" refers to an organic compound that contains a basic nitrogen atom with a lone pair of electrons Amines are derivatives of ammonia, wherein one or more hydrogen atoms have been replaced by a substituent such as an alkyl or aryl group. The basic nitrogen atom may also be part of a heterocyclic or heteroaryl ring.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

The term compound and molecule are used interchangeably. Other forms contemplated by the invention when the word "molecule" or "compound" is employed are salts, prodrugs, solvates, tautomers, stereoisomers and mixtures of stereoisomers. In some embodiments, the salts are pharmaceutically acceptable salts.

The term "pharmaceutically acceptable" refers to those properties and/or substances that are acceptable to a patient (e.g., human patient) from a toxicological and/or safety point of view.

The term "salt" means salts of the compounds of the present disclosure, which may be prepared with relatively nontoxic acids or bases, depending on the particular substituents found on the compounds described herein. When compounds of the present disclosure contain relatively acidic functionalities (e.g., —COOH group), base addition salts can be obtained by contacting the compound (e.g., neutral form of such compound) with a sufficient amount of the desired base, either neat or in a suitable inert solvent. Examples of pharmaceutically acceptable base addition salts include lithium, sodium, potassium, calcium, ammonium, organic amino, magnesium and aluminum salts and the like. When compounds of the present disclosure contain relatively basic functionalities (e.g., amines), acid addition salts can be obtained, e.g., by contacting the compound (e.g., neutral form of such compound) with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, diphosphoric, monohydrogenphosphoric, dihydrogenphosphoric, sulfuric, monohydrogensulfuric, hydriodic and the like, as well as the salts derived from relatively nontoxic organic acids like formic, acetic, propionic, isobutyric, malic, maleic, malonic, benzoic, succinic, suberic, fumaric, lactic, mandelic, phthalic, benzenesulfonic, p-tolylsulfonic, citric, tartaric, methanesulfonic, 2-hydroxyethylsulfonic, salicylic, stearic and the like. Also included are salts of amino acids such as arginate and the like, and salts of organic acids like glucuronic or galactunoric acids and the like (see, for example, Berge et al., *Journal of Pharmaceutical Science*, 1977, 66: 1-19). Certain specific compounds of the present disclosure contain both, basic and acidic, functionalities that allow the compounds to be converted into either base or acid addition salts. In addition, the counterion can be exchanged using conventional methods known in the art.

The neutral forms of the compounds can be regenerated, for example, by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present disclosure.

When a compound includes a negatively charged oxygen atom "O$^-$", e.g., in "—COO$^-$", then the formula is meant to optionally include a proton or an organic or inorganic cationic counterion (e.g., Na$^+$). In one example, the resulting salt form of the compound is pharmaceutically acceptable. Further, when a compound of the present disclosure includes an acidic group, such as a carboxylic acid group, e.g., written as the substituent "—COOH", "—CO$_2$H" or "—C(O)$_2$H", then the formula is meant to optionally include the corresponding "de-protonated" form of that acidic group, e.g., "—COO$^-$", "—CO$_2^-$" or "—C(O)$_2^-$", respectively.

Likewise, when a compound includes a positively charged nitrogen atom "N$^+$", then the formula is meant to optionally include an organic or inorganic anionic counterion (e.g., Cl$^-$). In one example, the resulting salt form of the compound is pharmaceutically acceptable. Further, when a compound of the present disclosure includes a basic group, such as an amine, then the formula is meant to optionally include the corresponding "protonated" form of that basic group, e.g., "NH$^+$".

Compounds of the present disclosure can exist in all tautomeric forms and, therefore, all tautomeric forms and mixtures of tautomers are included in the compounds disclosed herein.

Compounds of the present disclosure can also exist in particular geometric or stereoisomeric forms. The present disclosure contemplates all such compounds, including cis- and trans-isomers, (−)- and (+)-enantiomers, diastereomers, (D)-isomers, (L)-isomers, the racemic mixtures thereof, and other mixtures thereof, such as enantiomerically or diastereomerically enriched mixtures, as falling within the scope of the present disclosure. Additional asymmetric carbon atoms can be present in a substituent such as an alkyl group. All such isomers, as well as mixtures thereof, are intended to be included in this disclosure. When the compounds described herein contain olefinic double bonds or other centers of geometric asymmetry, and unless specified otherwise, it is intended that the compounds include both E and Z geometric isomers.

Optically active (R)- and (S)-isomers and d and l isomers can be prepared using chiral synthons or chiral reagents, or resolved using conventional techniques. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound. If, for instance, a particular enantiomer of a compound of the present disclosure is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The term "reaction conditions" is intended to refer to the physical and/or environmental conditions under which a chemical reaction proceeds. Examples of reaction conditions include, but are not limited to, one or more of following:

reaction temperature, solvent, pH, pressure, reaction time, mole ratio of reactants, the presence of a base or acid, or catalyst, etc. Reaction conditions may be named after the particular chemical reaction in which the conditions are employed, such as, coupling conditions, hydrogenation conditions, acylation conditions, reduction conditions, etc. Reaction conditions for most reactions are generally known to those skilled in the art or can be readily obtained from the literature. It is also contemplated that the reaction conditions can include reagents in addition to those listed in the specific reaction.

The term "amino-protecting group" refers to those organic groups intended to protect the nitrogen atom against undesirable reactions during synthetic procedures and includes, but is not limited to, silyl ethers, such as 2-(trimethylsilyl) ethoxymethyl (SEM) ether, or alkoxymethyl ethers, such as methoxymethyl (MOM) ether, tert-butoxymethyl (BUM) ether, benzyloxymethyl (BOM) ether or methoxyethoxymethyl (MEM) ether. Additional protecting groups include, tert-butyl, acetyl, benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like.

Certain protecting groups may be preferred over others due to their convenience or relative ease of removal, or due to their stereospecific effects in subsequent steps of the process. Additional suitable amino protecting groups are taught in T. W. Greene and P. G. M. Wuts, *Protecting Groups in Organic Synthesis*, Third Edition, Wiley, New York, 1999, and references cited therein which are all incorporated by reference in its entirety.

The term "anhydrous reaction conditions" is intended to refer to reaction conditions wherein water is excluded. Such conditions are known to one of skill in the art, and typically comprise one or more of dry or distilled solvents and reagents, dried reaction vessels, and/or the presence of a drying agent, such as activated molecular sieves, magnesium sulfate, sodium sulfate, etc.

The term "hydrogenation conditions" or "hydrogenation reaction conditions" is intended to refer to suitable conditions and catalysts for forming one or more new C—H bonds. Hydrogenation conditions or hydrogenation reaction conditions typically include a catalyst, such as those based on platinum group metals (platinum, palladium, rhodium, and ruthenium) (e.g. Pd/C or $PtO_2$).

The term "inert atmosphere" is intended to refer to an atmosphere comprising a gas which does not react with the reactants and reagents during the desired reaction process. Typically an inert atmosphere excludes oxygen and/or moisture. Exemplary gases include nitrogen and argon.

The term "under pressure" is intended to refer to reaction conditions which are conducted under a pressure of greater than 1 atmosphere. Such reactions can be carried out in a par hydrogenator or in an otherwise sealed reaction vessel (i.e. a screw capped flask) where the reaction is performed under heat such that the solvent vapors increase the pressure within the reaction vessel.

The term "acid" is intended to refer to a chemical species that can either donate a proton or accept a pair of electrons from another species. Examples of acids include organic acids, such as carboxylic acids (e.g. lactic acid, acetic acid, formic acid, citric acid, oxalic acid, uric acid, etc.) and sulfonic acids (e.g., methanesulfonic acid, p-toluenesulfonic acid), mineral acids (e.g. hydrochloric acid, nitric acid, phosphoric acid, sulfuric acid, boric acid, hydrofluoric acid, hydrobromic acid), Lewis acids, etc. The term "Lewis acid" is used herein refers to a molecule or ion that can combine with another molecule or ion by forming a covalent bond with two electrons from the second molecule or ion. For use in the process of the invention, a Lewis acid is considered as an electron deficient species that can accept a pair of electrons. Examples of Lewis acids that can be used in the present invention are cations of metals and their complexes including magnesium, calcium, aluminum, zinc, titanium, chromium, copper, boron, tin, mercury, iron, manganese, cadmium, gallium and barium. Their complex may include hydroxides, alkyls, alkoxides, halides and organic acid ligands such as acetates. Preferred examples of Lewis acids useful in the instant process are titanium alkoxides, particularly $Ti(OEt)_4$ which additionally possesses dehydrating properties.

The term "base" is intended to refer to a chemical species that are proton acceptors. Suitable bases for use in the present invention include inorganic or organic bases. Examples of inorganic base include, but are not limited to, potassium hydroxide (KOH), barium hydroxide ($Ba(OH)_2$), caesium hydroxide (CsOH), sodium hydroxide (NaOH), strontium hydroxide ($Sr(OH)_2$), calcium hydroxide ($Ca(OH)_2$), lithium hydroxide (LiOH), rubidium hydroxide (RbOH), and magnesium hydroxide ($Mg(OH)_2$). Organic bases can be neutral or negatively charged compounds which typically contain nitrogen atoms such as amines and nitrogen-containing heterocyclic compounds. Examples of neutral nitrogen containing organic bases include ammonia, pyridine, methyl amine, imidazole, 2,2,6,6-tetramethylpiperidine, 4-(dimethylamino) pyridine and the like. Examples of negatively charged organic bases includes alkyl lithium reagents, lithium dialkylamides, lithium alkyloxides, alkylmagnesium halides and the like.

Methods

The present invention provides methods for synthesizing variously substituted isoquinoline compounds, and the intermediate compounds achieved thereby. The methods enable the isoquinoline compounds to be prepared safely and efficiently on a large scale, such as would be desired for the commercial production of such compounds.

One advantage of the present methods over those disclosed previously is that the methods disclosed herein do not require the separation of regioisomers. For example, the methods disclosed in Suzuki et al. (supra), Weidmann et al. (supra), and U.S. Pat. No. 7,629,357, provide a regioisomeric mixture of the 5- and 8-substituted isoquinoline compounds or the 6- and 7-substituted isoquinoline compounds, which are then separated using standard chromatographic methods. However, such separations are undesireable as the maximum theoretical yield for the step can be only 50%.

Another advantage of the present methods over those disclosed previously, is that the methods disclosed herein do not utilize hazardous and/or costly reagents. Specifically, the methods disclosed herein avoid the halogenation step and thus avoid reagents such as phosphorous oxychloride and phosphorous oxybromide (see, for example, previously disclosed synthesis in U.S. Pat. No. 7,323,475 described in Scheme E herein, E-400 to E-500). These reagents are extremely destructive to tissue of the mucous membranes, upper respiratory tract, eyes, and skin. In addition, the methods avoid reagents such as n-butyllithium and trimethylboroxine, both of which require special handling procedures as they are very reactive to moisture. Therefore, the methods disclosed herein are advantageous over such methods which utilize undesirable reagents.

The methods of this invention employ starting compounds which can be prepared from readily available starting materials or the compounds as disclosed herein using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the methods of this invention may employ compounds which contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., U.S.A), Bachem (Torrance, Calif., U.S.A), Emka-Chemce or Sigma (St. Louis, Mo., U.S.A). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

In one aspect, the present invention is directed to a method of making a compound of formula I or a stereoisomer or mixture of stereoisomers thereof:

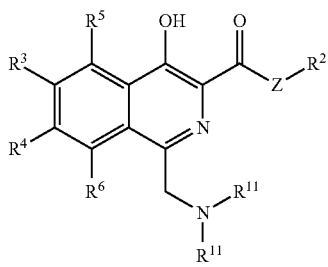

I the method comprising contacting a compound of formula II:

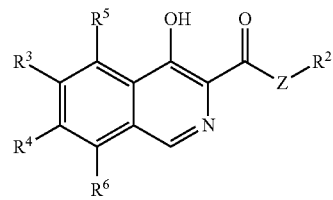

II with a compound of formula III:

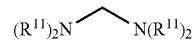

III under reaction conditions sufficient to produce a compound of formula I; wherein Z is O, NR$^1$, or S;

R$^1$ is selected from the group consisting of hydrogen and alkyl;

R$^2$ is selected from the group consisting of hydrogen and alkyl which is unsubstituted or substituted with one or more substituents independently selected from the group consisting of cycloalkyl, heterocyclyl, aryl, and heteroaryl;

R$^3$ and R$^4$ are independently selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, —S(O)$_n$—N(R$^8$)—R$^8$, —NR$^8$C(O)NR$^8$R$^8$, and —X$^1$R$^8$;

where X$^1$ is oxygen, —S(O)$_n$—, or —NR$^9$—;

n is 0, 1, or 2;

each R$^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when X$^1$ is —SO— or —SO$_2$—, then R$^8$ is not hydrogen; and R$^9$ is selected from the group consisting of hydrogen, alkyl, and aryl;

or R$^3$ and R$^4$ together with the carbon atoms pendent thereto, form a cycloalkyl, substituted cycloalkyl, heterocyclyl, substituted heterocyclyl, aryl, substituted aryl, heteroaryl, or substituted heteroaryl;

R$^5$ and R$^6$ are independently selected from the group consisting of hydrogen, halo, alkyl, substituted alkyl, alkoxy, substituted alkoxy, aryl, substituted aryl, heteroaryl, substituted heteroaryl and —X$^2$R$^{10}$;

where X$^2$ is oxygen, —S(O)$_n$—, or —NR$^{13}$—;

n is 0, 1, or 2;

R$^{10}$ is selected from the group consisting of alkyl, substituted alkyl, aryl, substituted aryl, heteroaryl, substituted heteroaryl, heterocyclyl and substituted heterocyclyl; and R$^{13}$ is selected from the group consisting of hydrogen, alkyl, and aryl;

or when X$^2$ is —NR$^{13}$—, then R$^{10}$ and R$^{13}$, together with the nitrogen atom to which they are bound, can be joined to form a heterocyclyl or substituted heterocyclyl group; and each $R^{11}$ is independently selected from alkyl, benzyl or aryl, or two $R^{11}$ together with the nitrogen atom to which they are attached form a 4-8 membered heterocyclyl or a heteroaryl.

In particular embodiments, the present invention is directed to a method of making a compound of formula IA or a stereoisomer or mixture of stereoisomers thereof:

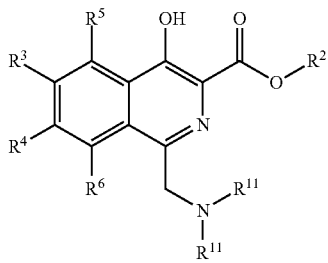

IA comprising contacting a compound of formula IIA:

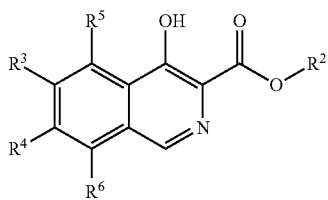

IIA with a compound of formula III:

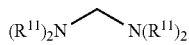

III under reaction conditions sufficient to produce a compound of formula IA; wherein $R^2$, $R^3$, $R^4$, $R^5$, $R^6$, $R^8$, $R^9$, $R^{10}$, $R^{11}$, $R^{13}$, n, $X^1$ and $X^2$ are as defined for formula I above.

The reaction may be carried out in glacial acetic acid or a polar aprotic solvent such as dioxane, tetrahydrofuran (THF), dimethylformamide (DMF), or dimethylacetamide (DMAc) to produce compounds of formula I or IA with or without an acid catalyst. In certain embodiments, the reaction conditions comprise an acid. The acid may be selected from, e.g., acetic acid, trifluoroacetic acid, sulfuric acid, hydrochloric acid, or an acidic ion exchange resin. In various embodiments, about 0.1-14 molar equivalents of acid may be used. In some embodiments, the acid is glacial acetic acid. In some embodiments, at least about 2 molar equivalents of glacial acetic acid are used. In particular embodiments, about 7 to about 8 molar equivalents of glacial acetic acid are used.

In certain embodiments, the reaction is conducted under an inert atmosphere, such as an argon or nitrogen atmosphere. In some embodiments, the reaction is conducted under a nitrogen atmosphere.

In certain embodiments, the reaction conditions are anhydrous reaction conditions. Such conditions typically include drying reagents (e.g. molecular sieves), conducting the reaction under an inert atmosphere, and the like. Such methods are well known in the art.

In certain embodiments, the reaction is conducted at a temperature between room temperature (ca 25° C.) and 110° C., and at a pressure from 0 to 60 psi. In some embodiments, the reaction is conducted at an elevated temperature, i.e., at a temperature greater than about 30° C. For example, the temperature can range from about 50° C. to about 60° C.

In certain embodiments, from about 1.1 to about 1.5 molar equivalents of the compound of formula III is used.

In certain embodiments, the reaction is conducted in glacial acetic acid, and at a temperature range from about 50° C. to about 60° C.; and $R^{11}$ of a compound of formula III is $C_1$ to $C_4$ alkyl.

In certain embodiments, the reaction is conducted in glacial acetic acid, under a nitrogen atmosphere, and at a temperature range from about 50° C. to about 60° C.; and $R^{11}$ of a compound of formula III is $C_1$ to $C_4$ alkyl.

In certain embodiments, the reaction is conducted in about 7 to about 8 molar equivalents of glacial acetic acid, at a temperature range from about 50° C. to about 60° C., and about 1.1 to about 1.5 molar equivalents of a compound of formula III is used where $R^{11}$ is $C_1$ to $C_4$ alkyl.

In certain embodiments, the reaction is conducted in about 7 to about 8 molar equivalents of glacial acetic acid, under a nitrogen atmosphere, at a temperature range from about 50° C. to about 60° C., and about 1.1 to about 1.5 molar equivalents of a compound of formula III is used where $R^{11}$ is $C_1$ to $C_4$ alkyl.

In certain embodiments, $R^{11}$ of a compound of formula III is $C_1$ to $C_4$ alkyl. In certain embodiments, the compound of formula III comprises a compound of formula IIIA:

IIIA

In another aspect, the present invention is directed to a method of making a compound of formula IV or a stereoisomer or mixture of stereoisomers thereof:

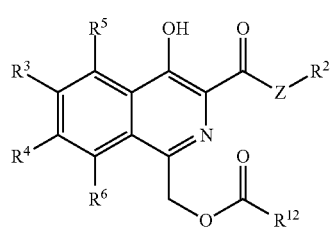

IV the method comprising contacting a compound of formula I:

$$\text{I}$$

(structure: isoquinoline with R$^3$, R$^4$, R$^5$, R$^6$ on benzene ring, OH at 4-position, C(=O)-Z-R$^2$ at 3-position, and CH$_2$-N(R$^{11}$)(R$^{11}$) at 1-position)

with one of the following:
  (a) a compound of formula $$\underset{R^{12}}{\overset{O}{\|}}\!\!-\!\!X^3$$

followed by a compound of formula $$\underset{R^{12}}{\overset{O}{\|}}\!\!-\!\!OH;$$

(b) a compound of formula R$^{12}$—X$^3$ followed by a compound of formula $$\underset{R^{12}}{\overset{O}{\|}}\!\!-\!\!OH;$$

or
  (c) a compound of formula V:

$$\underset{R^{12}}{\overset{O}{\|}}\!\!-\!\!O\!\!-\!\!\underset{R^{12}}{\overset{O}{\|}} \qquad \text{V}$$

under reaction conditions sufficient to produce a compound of formula IV; wherein
  X$^3$ is halo;
  R$^{12}$ is selected from the group consisting of alkyl, aryl, heteroaryl, and heterocyclyl, or when two R$^{12}$ are present, two R$^{12}$ together with the carbon atom to which they are attached form a 4-8 membered heterocyclyl; and
  Z, R$^1$, R$^2$, R$^3$, R$^4$, R$^5$, R$^6$, R$^8$, R$^9$, R$^{10}$, R$^{11}$, R$^{13}$, n, X$^1$ and X$^2$ are as defined for formula I above.

In one embodiment, the present invention is directed to a method of making a compound of formula IVA or a stereoisomer or mixture of stereoisomers thereof:

$$\text{IVA}$$

(structure showing isoquinoline with R$^3$, R$^4$, R$^5$, R$^6$ substituents, OH, C(=O)-O-R$^2$, and CH$_2$-O-C(=O)-R$^{12}$)

comprising contacting a compound of formula IA:

$$\text{IA}$$

(structure with R$^3$, R$^4$, R$^5$, R$^6$, OH, C(=O)-O-R$^2$, CH$_2$-N(R$^{11}$)(R$^{11}$))

with a compound of formula V:

$$\underset{R^{12}}{\overset{O}{\|}}\!\!-\!\!O\!\!-\!\!\underset{R^{12}}{\overset{O}{\|}} \qquad \text{V}$$

under reaction conditions sufficient to produce a compound of formula IVA; wherein
  R$^{12}$ is selected from the group consisting of alkyl, aryl, heteroaryl, and heterocyclyl, or when two R$^{12}$ are present, two R$^{12}$ together with the carbon atom to which they are attached form a 4-8 membered heterocyclyl; and
  R$^2$, R$^3$, R$^4$, R$^5$, R$^6$, R$^8$, R$^9$, R$^{10}$, R$^{11}$, R$^{13}$, n, X$^1$ and X$^2$ are as defined for formula I above.

The reaction may be carried out in glacial acetic acid or a polar aprotic solvent such as dioxane, THF, DMF, or DMAc with or without an acid catalyst. In certain embodiments, the reaction conditions comprise an acid. The acid may be selected from, e.g., acetic acid, trifluoroacetic acid, sulfuric acid, hydrochloric acid, or an acidic ion exchange resin. In various embodiments, about 0.1-14 molar equivalents of acid may be used. In some embodiments, the acid is glacial acetic acid. In some embodiments, at least about 2 molar equivalents of glacial acetic acid are used. In particular embodiments, about 7 to about 8 molar equivalents of glacial acetic acid are used.

In certain embodiments, the reaction is conducted under an inert atmosphere, such as an argon or nitrogen atmosphere. In some embodiments, the reaction is conducted under a nitrogen atmosphere.

In certain embodiments, the reaction conditions are anhydrous reaction conditions. Such conditions typically include drying reagents (e.g. molecular sieves), conducting the reaction under an inert atmosphere, and the like. Such methods are well known in the art.

In certain embodiments, the reaction is conducted at an elevated temperature, i.e., at a temperature greater than about 30° C. For example, in certain embodiments, the temperature is about 100° C.

In various embodiments, from about 1 to about 4 molar equivalents of the compound of formula V is used. In particular embodiments, where the compound of formula I or IA is isolated prior to reaction, about 1 molar equivalent of the compound of formula V is used. In other embodiments, from about 2 to about 3 molar equivalents of the compound of formula V is used. In certain embodiments, the compound of formula V comprises acetic anhydride.

In certain embodiments, the reaction conditions comprise a compound of formula V where $R^{12}$ is $C_1$ to $C_4$ alkyl; and the reaction is conducted at an elevated temperature.

In certain embodiments, the reaction conditions comprise a compound of formula V where $R^{12}$ is $C_1$ to $C_4$ alkyl; and the reaction is conducted at a temperature of about 100° C.

In certain embodiments the reaction conditions comprise a compound of formula V where $R^{12}$ is $C_1$ to $C_4$ alkyl; and the reaction is conducted under an inert atmosphere, and at an elevated temperature. In certain embodiments, further a compound of formula V is acetic anhydride.

In certain embodiments, the reaction conditions comprise about 2 to about 3 molar equivalents of a compound of formula V where $R^{12}$ is $C_1$ to $C_4$ alkyl; and the reaction is conducted at a temperature of about 100° C. In certain embodiments, further a compound of formula V is acetic anhydride.

In certain embodiments, the reaction conditions comprise about 2 to about 3 molar equivalents of a compound of formula V where $R^{12}$ is $C_1$ to $C_4$ alkyl; and the reaction is conducted under a nitrogen atmosphere, and at a temperature of about 100° C. In certain embodiments, further a compound of formula V is acetic anhydride.

In certain embodiments, the reaction conditions further comprise converting a compound of formula VII to a compound of formula IV:

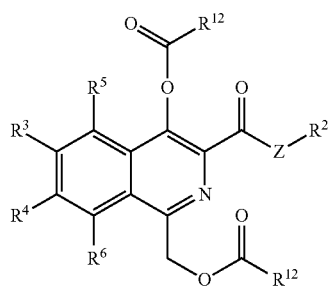

VII

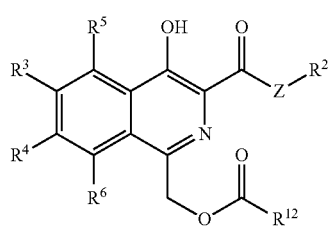

IV under reaction conditions sufficient to produce a compound of formula IV;
wherein Z, $R^1$, $R^2$, $R^3$, $R^4$, $R^5$, $R^6$, $R^8$, $R^9$, $R^{10}$, $R^{13}$, n, $X^1$ and $X^2$ are as defined for formula I above; and $R^{12}$ is selected from the group consisting of alkyl, aryl, heteroaryl, and heterocyclyl.

In certain embodiments, the reaction conditions further comprise converting a compound of formula VIIA to a compound of formula IVA:

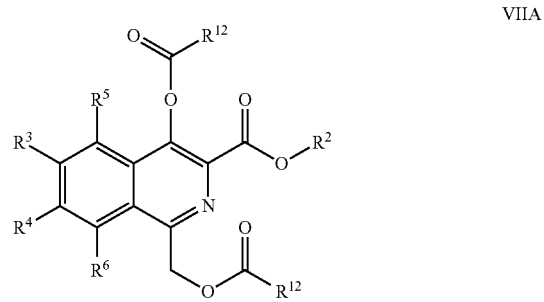

VIIA

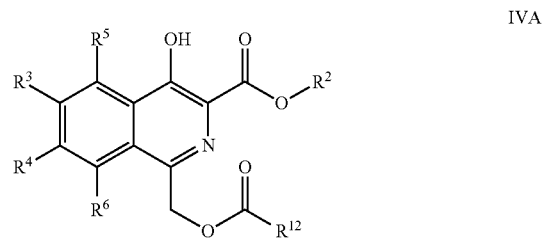

IVA under reaction conditions sufficient to produce a compound of formula IVA;
wherein $R^2$, $R^3$, $R^4$, $R^5$, $R^6$, $R^8$, $R^9$, $R^{10}$, $R^{13}$, n, $X^1$ and $X^2$ are as defined for formula I above; and $R^{12}$ is selected from the group consisting of alkyl, aryl, heteroaryl, and heterocyclyl.

In certain embodiments, the reaction is conducted in a solvent selected from dichloromethane, ethyl acetate or THF. In particular embodiments, the solvent is dichloromethane.

In certain embodiments, the reaction conditions comprise an amine In some embodiments, the amine is morpholine. In certain embodiments, the reaction is conducted at a temperature from about 0° C. to about 10° C.

In certain embodiments, the reaction conditions comprise morpholine; and the reaction is conducted in dichloromethane, and at a temperature from about 0° C. to about 10° C.

In another aspect, the present invention is directed to a method of making a compound of formula VI or a stereoisomer or mixture of stereoisomers thereof:

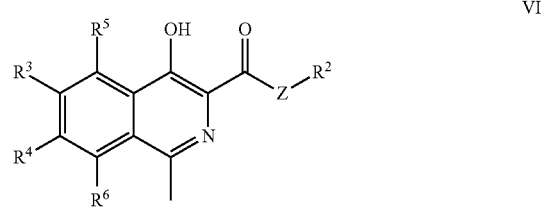

VI the method comprising converting a compound of formula IV:

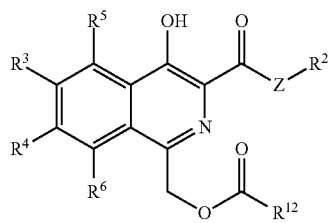

under reaction conditions sufficient to produce a compound of formula VI;

wherein Z, $R^1$, $R^2$, $R^3$, $R^4$, $R^5$, $R^6$, $R^8$, $R^9$, $R^{10}$, $R^{13}$, n, $X^1$ and $X^2$ are as defined for formula I above; and $R^{12}$ is selected from the group consisting of alkyl, aryl, heteroaryl, and heterocyclyl.

In another embodiment, the present invention is directed to a method of making a compound of formula VIA or a stereoisomer or mixture of stereoisomers thereof:

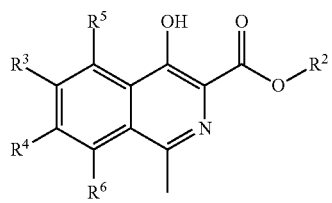

comprising converting a compound of formula IVA:

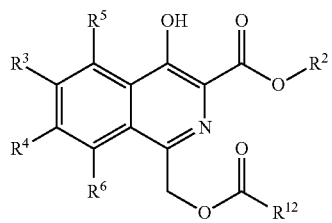

under reaction conditions sufficient to produce a compound of formula VIA;

wherein $R^2$, $R^3$, $R^4$, $R^5$, $R^6$, $R^8$, $R^9$, $R^{10}$, $R^{13}$, n, $X^1$ and $X^2$ are as defined for formula I above; and $R^{12}$ is selected from the group consisting of alkyl, aryl, heteroaryl, and heterocyclyl.

In certain embodiments, the reaction conditions to produce VI or VIA are hydrogenation reaction conditions. Such conditions typically comprise hydrogen. Such conditions also typically comprise a catalyst, such as a palladium catalyst (e.g. Pd/C, also known as palladium(0) on carbon). Alternatively, Pd(OH)$_2$/C or Raney nickel may be used.

In certain embodiments, the reaction conditions comprise a solvent selected from dichloromethane, ethyl acetate, or methanol. In particular embodiments, the reaction conditions comprise dichloromethane. In particular embodiments, the reaction conditions comprise ethyl acetate.

In some embodiments, the reaction is conducted in a hydrogen atmosphere and under pressure, e.g., at about 20 to about 300 psi, or at about 60 psi. In some embodiments, the reaction conditions comprise a base, such as sodium carbonate or sodium bicarbonate. In some embodiments, the hydrogenation reaction conditions comprise from about 0.5 to about 1 molar equivalents of sodium carbonate.

In certain embodiments, the reaction conditions comprise hydrogen, sodium carbonate, ethyl acetate, Pd/C, and a condition under pressure.

In certain embodiments, the reaction conditions comprise hydrogen, sodium carbonate, ethyl acetate, Pd/C, and a condition under pressure at about 60 psi.

In certain embodiments, the present invention is directed to a method of making a compound of formula VI or a stereoisomer or mixture of stereoisomers thereof:

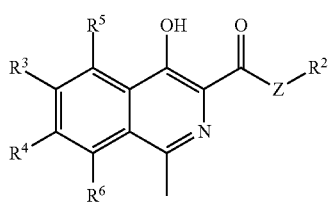

comprising the steps of:

a) contacting a compound of formula II with a compound of formula III

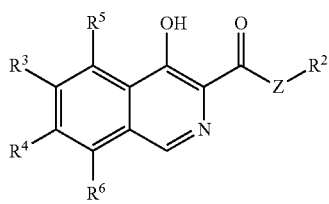

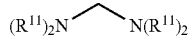

under reaction conditions sufficient to provide a compound of formula I:

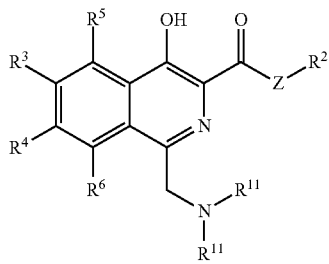

b) contacting a compound of formula I with one of the following:
(i) a compound of formula

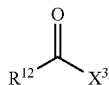

followed by a compound of formula

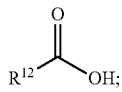

(ii) a compound of formula $R^{12}—X^3$ followed by a compound of formula

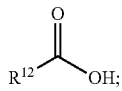

or
(iii) a compound of formula V:

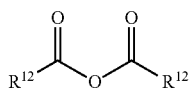

under conditions sufficient to produce a compound of formula IV:

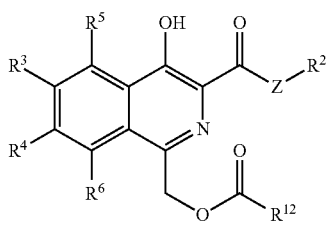

c) optionally converting a compound of formula VII:

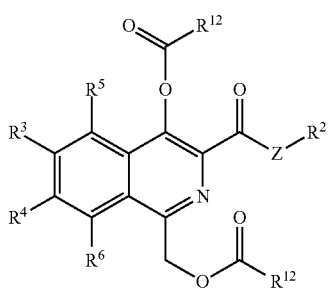

to a compound of formula IV; and d) converting a compound of formula IV under conditions sufficient to produce a compound of formula VI;
wherein
$X^3$ is halo;
$R^{12}$ is selected from the group consisting of alkyl, aryl, heteroaryl, and heterocyclyl, or when two $R^{12}$ are present, two $R^{12}$ together with the carbon atom to which they are attached form a 4-8 membered heterocyclyl; and
$Z, R^1, R^2, R^3, R^4, R^5, R^6, R^8, R^9, R^{10}, R^{11}, R^{13}, n, X^1$ and $X^2$ are as defined for formula I above.

In certain embodiments, the present invention is directed to a method of making a compound of formula VIA or a stereoisomer or mixture of stereoisomers thereof:

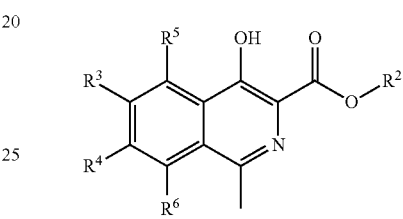

comprising the steps of:
a) contacting a compound of formula IIA with a compound of formula III

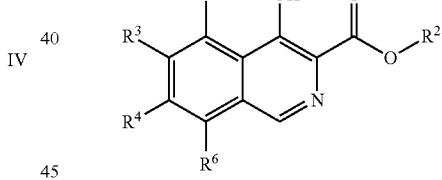

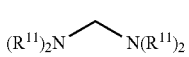

under reaction conditions to provide a compound of formula IA:

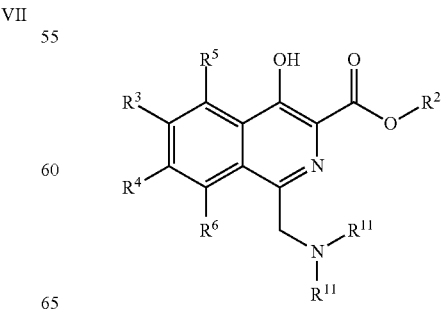

b) contacting a compound of formula IA with a compound of formula V

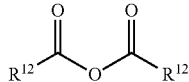

under reaction conditions sufficient to produce a compound of formula IVA:

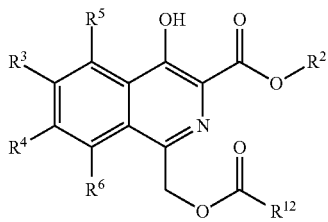

c) optionally converting a compound of formula VIIA

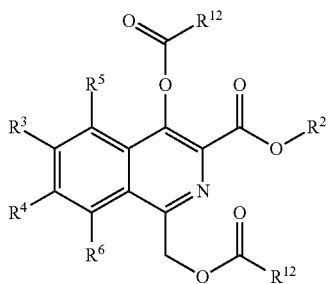

to a compound of formula IVA; and d) converting a compound of formula IVA under conditions sufficient to produce a compound of formula VIA;

wherein $R^2, R^3, R^4, R^5, R^6, R^8, R^9, R^{10}, R^{11}, R^{13}$, n, $X^1$ and $X^2$ are as defined for formula I above; and $R^{12}$ is selected from the group consisting of alkyl, aryl, heteroaryl, and heterocyclyl.

In certain embodiments, the present invention is directed to a method of making a compound of formula VIC or a stereoisomer or mixture of stereoisomers thereof:

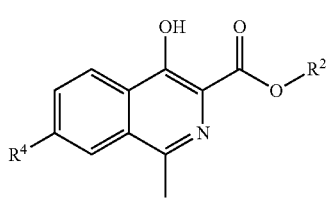

comprising the steps of:

a) contacting a compound of formula IIC with a compound of formula IIIA

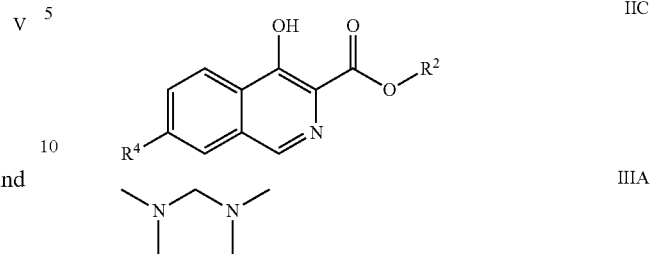

under reaction conditions sufficient to provide a compound of formula IC:

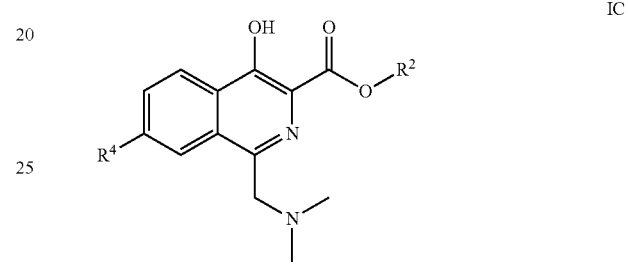

b) contacting a compound of formula IC with a compound of formula VA

under reaction conditions sufficient to produce a compound of formula IVC:

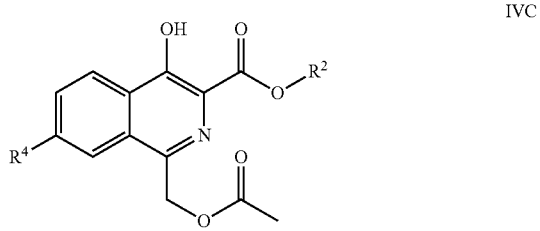

c) optionally converting a compound of formula VIIC

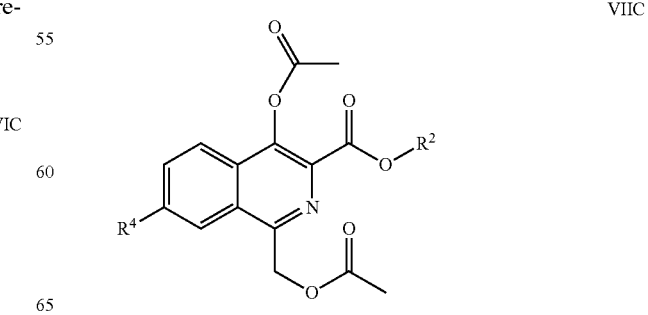

to a compound of formula IVC; and d) converting a compound of formula IVC under conditions sufficient to produce a compound of formula VIC;

wherein

R² is selected from the group consisting of hydrogen and alkyl which is unsubstituted or substituted with one or more substituents independently selected from the group consisting of cycloalkyl, heterocyclyl, aryl, and heteroaryl; and R⁴ is selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, —S(O)$_n$—N(R⁸)—R⁸, —NR⁸C(O)NR⁸R⁸, and —X¹R⁸;

where X¹ is oxygen, —S(O)$_n$—, or —NR⁹—;

n is 0, 1, or 2;

each R⁸ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when X¹ is —SO— and —SO₂—, then R⁸ is not hydrogen; and R⁹ is selected from the group consisting of hydrogen, alkyl, and aryl.

In certain embodiments, the present invention is directed to a method of making a compound of formula VID or a stereoisomer or mixture of stereoisomers thereof:

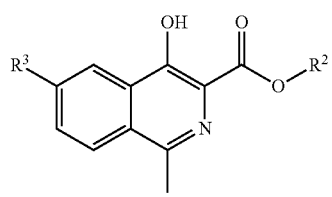

VID comprising the steps of:

a) contacting a compound of formula IID with a compound of formula IIIA

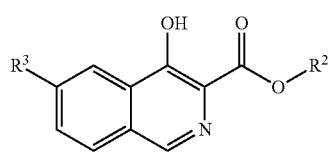

IID

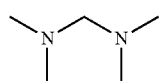

III under reaction conditions to provide a compound of formula ID:

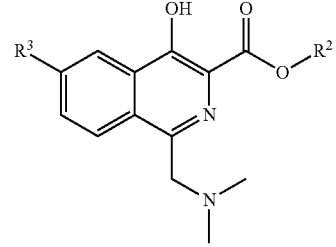

ID b) contacting a compound of formula ID with a compound of formula VA

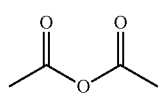

VA under reaction conditions sufficient to produce a compound of formula IVD:

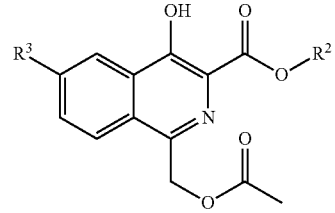

IVD c) optionally converting a compound of formula VIID

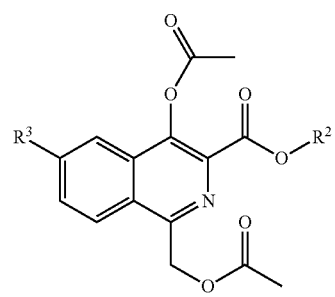

VIID to a compound of formula IVD; and d) converting a compound of formula IVD under conditions sufficient to produce a compound of formula VID;

wherein

R² is selected from the group consisting of hydrogen and alkyl which is unsubstituted or substituted with one or more substituents independently selected from the group consisting of cycloalkyl, heterocyclyl, aryl, and heteroaryl; and R³ is selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, —S(O)$_n$—N(R$^8$)—R$^8$, —NR$^8$C(O)NR$^8$R$^8$, and —X$^1$R$^8$;

where X$^1$ is oxygen, —S(O)$_n$—, or —NR$^9$—;

n is 0, 1, or 2;

each R$^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when X$^1$ is —SO— and —SO$_2$—, then R$^8$ is not hydrogen; and R$^9$ is selected from the group consisting of hydrogen, alkyl, and aryl.

In certain embodiments of the above methods, R$^2$ is hydrogen.

In certain embodiments of the above methods, R$^2$ is alkyl.

In certain embodiments of the above methods, R$^3$ is phenoxy.

In certain embodiments of the above methods, R$^3$ is 4-methoxyphenoxy.

In certain embodiments of the above methods, R$^3$ is 3,5-difluorophenoxy.

In certain embodiments of the above methods, R$^4$ is phenoxy.

In certain embodiments of the above methods, R$^4$ is 4-methoxyphenoxy.

In certain embodiments of the above methods, R$^4$ is 3,5-difluorophenoxy.

In certain embodiments of the above methods, R$^2$ is hydrogen and R$^3$ is phenoxy.

In certain embodiments of the above methods, R$^2$ is hydrogen and R$^3$ is 4-methoxyphenoxy.

In certain embodiments of the above methods, R$^2$ is hydrogen and R$^3$ is 3,5-difluorophenoxy.

In certain embodiments of the above methods, R$^2$ is hydrogen and R$^4$ is phenoxy.

In certain embodiments of the above methods, R$^2$ is hydrogen and R$^4$ is 4-methoxyphenoxy.

In certain embodiments of the above methods, R$^2$ is hydrogen and R$^4$ is 3,5-difluorophenoxy.

In certain embodiments of the above methods described herein, the compound of formula VI is represented by formula VIB:

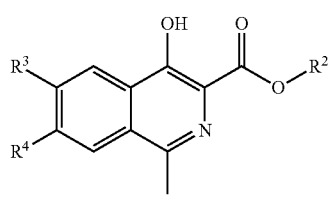

VIB where R$^2$, R$^3$ and R$^4$ are as defined for formula I above.

In certain embodiments of the above methods, the compound of formula II is represented by formula IIB:

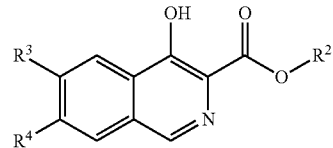

IIB wherein R$^2$, R$^3$ and R$^4$ are as defined for formula I above.

In certain embodiments of the above methods, the compound of formula III is represented by formula IIIA:

IIIA

In certain embodiments of the above methods, the compound of formula III is represented by:

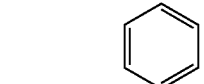

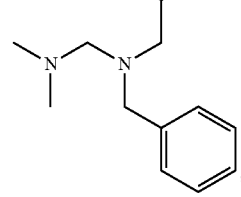

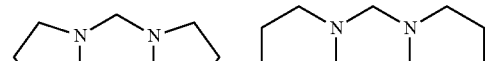

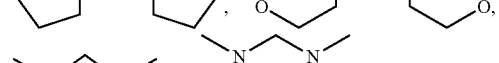

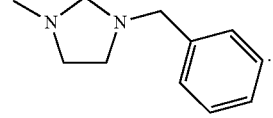

In certain embodiments of the above methods, the compound of formula I is represented by formula IB:

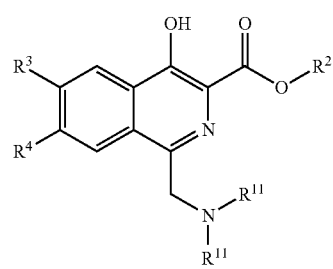

IB where R$^2$, R$^3$, R$^4$ and R$^{11}$ are as defined for formula I above.

In certain embodiments of the above methods, the compound of formula V is represented by formula VA:

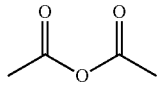
VA

In certain embodiments of the above methods, the compound of formula V is represented by:

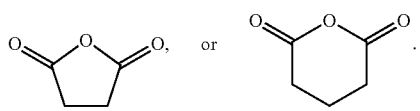 [SMILES: O=C1CCC(=O)O1 ; "or" ; O=C1CCCC(=O)O1]

In certain embodiments of the above methods, the compound of formula VII is represented by formula VIIB:

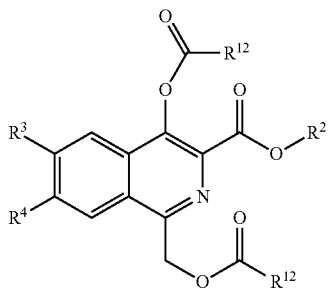
VIIB where $R^2$, $R^3$, and $R^4$ are as defined for formula I above, and $R^{12}$ is selected from the group consisting of alkyl, aryl, heteroaryl, and heterocyclyl.

In certain embodiments of the above methods, the compound of formula IV is represented by formula IVB:

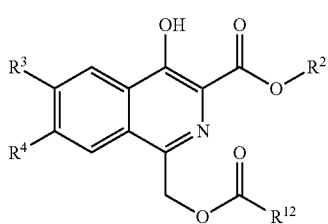
IVB where $R^2$, $R^3$, and $R^4$ are as defined for formula I above, and $R^{12}$ is selected from the group consisting of alkyl, aryl, heteroaryl, and heterocyclyl.

In an alternative embodiment, the present invention is directed to a method of making compounds represented by formula X or a stereoisomer or mixture of stereoisomers thereof:

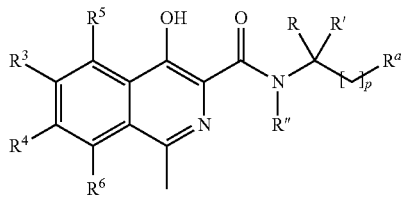
X comprising the steps of:

a) contacting a compound of formula II with a compound of formula III

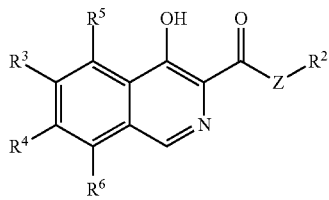
II

III under reaction conditions sufficient to provide a compound of formula I:

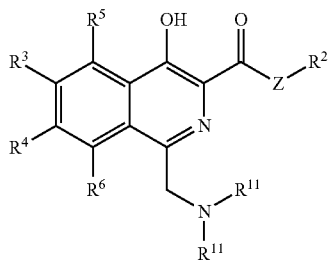
I b) contacting a compound of formula I with one of the following:

(iv) a compound of formula

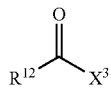

followed by a compound of formula

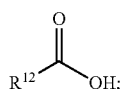

(v) a compound of formula $R^{12}$—$X^3$ followed by a compound of formula

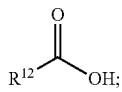

or (vi) a compound of formula V:

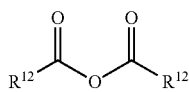

under conditions sufficient to produce a compound of formula IV:

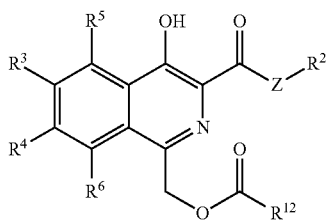

c) optionally converting a compound of formula VII:

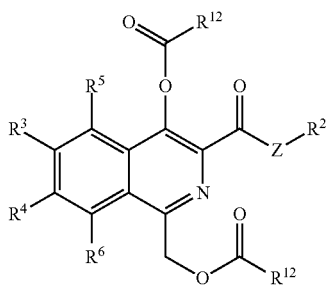

to a compound of formula IV;

d) converting a compound of formula IV; under conditions sufficient to produce a compound of formula VI; and

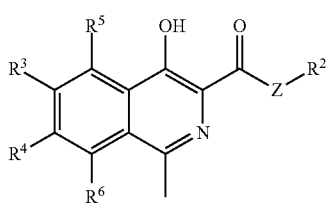

e) contacting a compound of formula VI with a compound of formula

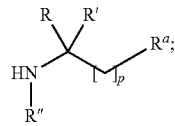

under reaction conditions sufficient to provide a compound of formula X:

wherein Z, $R^1$, $R^2$, $R^3$, $R^4$, $R^5$, $R^6$, $R^8$, $R^9$, $R^{10}$, $R^{11}$, $R^{13}$, n, $X^1$ and $X^2$ are as defined for formula I above;

$X^3$ is halo;

$R^{12}$ is selected from the group consisting of alkyl, aryl, heteroaryl, and heterocyclyl, or when two $R^{12}$ are present, two $R^{12}$ together with the carbon atom to which they are attached form a 4-8 membered heterocyclyl;

p is 0 when $R^a$ is —COOH; p is 1 when $R^a$ is —$WR^{18}$;

W is selected from the group consisting of oxygen, —S(O)$_n$— and —$NR^{19}$— where n is 0, 1, or 2, $R^{19}$ is selected from the group consisting of hydrogen, alkyl, substituted alkyl, acyl, aryl, substituted aryl, heteroaryl, substituted heteroaryl, heterocyclyl and substituted heterocyclyl and $R^{18}$ is selected from the group consisting of hydrogen, alkyl, substituted alkyl, aryl, substituted aryl, heteroaryl, substituted heteroaryl, heterocyclyl and substituted heterocyclyl, or when W is —$NR^{19}$— then $R^{18}$ and $R^{19}$, together with the nitrogen atom to which they are bound, can be joined to form a heterocyclyl or a substituted heterocyclyl group;

R is selected from the group consisting of hydrogen, deuterium and methyl;

R' is selected from the group consisting of hydrogen, deuterium, alkyl and substituted alkyl; alternatively, R and R' and the carbon pendent thereto can be joined to form cycloalkyl, substituted cycloalkyl, heterocyclyl or substituted heterocyclyl group; and R" is selected from the group consisting of hydrogen and alkyl or R" together with R' and the nitrogen pendent thereto can be joined to form a heterocyclyl or substituted heterocyclyl group;

and pharmaceutically acceptable salts, stereoisomers, mixture of stereoisomers, and esters thereof In another embodiment, the present disclosure is directed to a method of making methyl 4-hydroxy-1-methyl-7-phenoxyisoquinoline-3-carboxylate (3e):

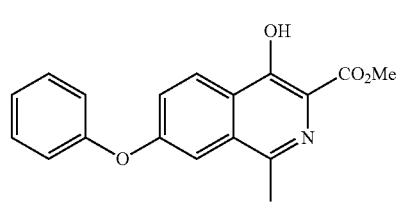

comprising the steps of:

a) contacting a compound of formula 3a with a compound of formula IIIA

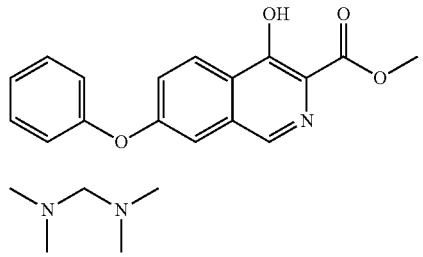

under reaction conditions sufficient to produce a compound of formula 3b:

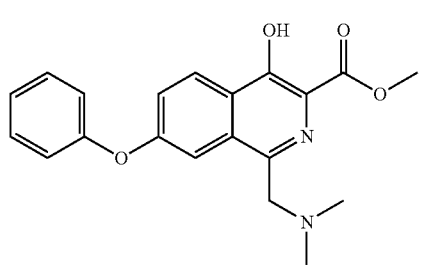

b) contacting a compound of formula 3b with a compound of formula VA

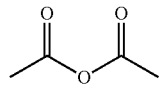

under reaction conditions sufficient to produce a compound of formula 3c:

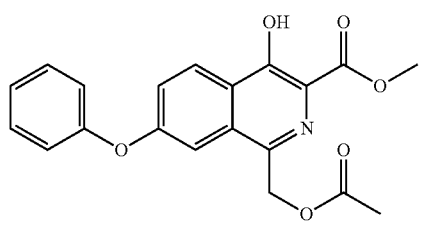

c) optionally converting a compound of formula 3d:

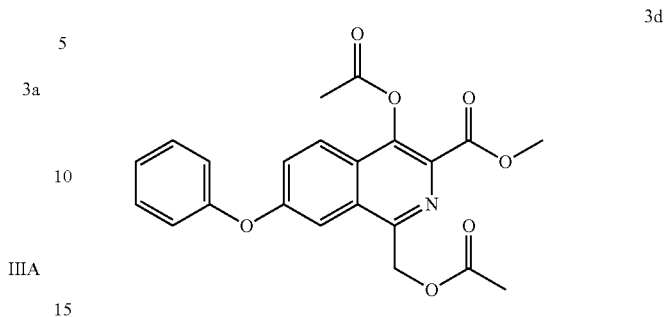

under reaction conditions sufficient to produce a compound of formula 3c; and d) converting a compound of formula 3c under reaction conditions sufficient to produce a compound of formula 3e.

In another embodiment, the present disclosure is directed to a method of making 2-(4-hydroxy-1-methyl-7-phenoxy-isoquinoline-3-carboxamido)acetic acid (3f)

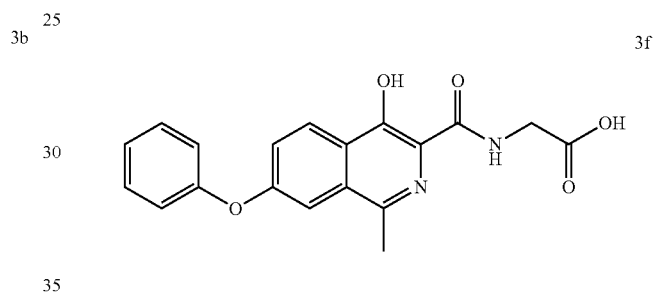

comprising contacting a compound of formula 3e with glycine or sodium glycinate

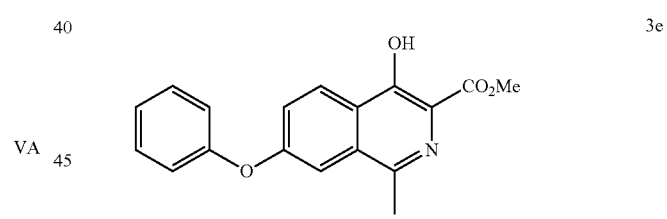

under reaction conditions sufficient to produce a compound of formula 3f.

Compounds of formula II:

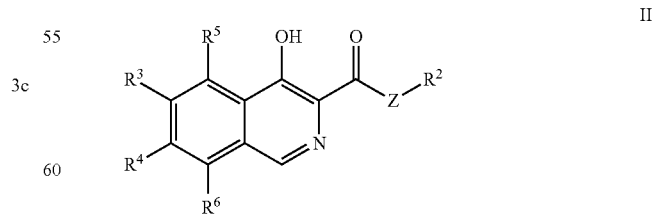

for use in the methods disclosed herein can be prepared according to published procedures (see, for example, U.S. Pat. No. 7,323,475, which is hereby incorporated by reference in its entirety).

In certain embodiments of the methods disclosed herein above, each of $R^3$, $R^4$, $R^5$, $R^6$, $R^8$, $R^9$, and $R^{10}$ are as defined below:

$R^3$ and $R^4$ are independently selected from the group consisting of hydrogen, alkyl, cycloalkyl, heterocyclyl, aryl, heteroaryl, halo, hydroxy, cyano, —S(O)$_n$—N(R$^8$)—R$^8$, —NR$^8$C(O)NR$^8$R$^8$, and —X$^1$R$^8$; where $X^1$ is oxygen, —S(O)$_n$—, or —NR$^9$—;

n is 0, 1, or 2;

each $R^8$ is independently selected from the group consisting of hydrogen, alkyl, aryl, cycloalkyl, heteroaryl, and heterocyclyl provided that when $X^1$ is —SO— or —SO$_2$—, then $R^8$ is not hydrogen; and $R^9$ is selected from the group consisting of hydrogen, alkyl, and aryl;

or $R^3$ and $R^4$ together with the carbon atoms pendent thereto, form a cycloalkyl, heterocyclyl, aryl, or heteroaryl;

$R^5$ and $R^6$ are independently selected from the group consisting of hydrogen, halo, alkyl, alkoxy, aryl, heteroaryl, and —X$^2$R$^{10}$; where $X^2$ is oxygen, —S(O)$_n$—, or —NR$^{13}$—;

n is 0, 1, or 2;

$R^{10}$ is selected from the group consisting of alkyl, aryl, heteroaryl, and heterocyclyl; and $R^{13}$ is selected from the group consisting of hydrogen, alkyl, and aryl;

or when $X^2$ is —NR$^{13}$—, then $R^{10}$ and $R^{13}$, together with the nitrogen atom to which they are bound, can be joined to form a heterocyclyl group;

wherein each alkyl, alkoxy, cycloalkyl, heterocyclyl, aryl, heteroaryl, and heterocyclyl described above can be optionally substituted with from 1 to 3 $R^{100}$, wherein each $R^{100}$ is independently selected from the group consisting of alkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicheterocyclylthio, sulfonyl, heteroaryl, heterocyclicheterocyclyl, cycloalkoxy, heteroaryloxy, heterocyclyloxy, oxycarbonylamino, oxythiocarbonylamino, —OS(O)$_2$-alkyl, —OS(O)$_2$-aryl, —OS(O)$_2$-heteroaryl, —OS(O)$_2$-heterocyclyl, —OSO$_2$—NR$^{40}$R$^{40}$, —NR$^{40}$S(O)$_2$—NR$^{40}$-alkyl, —NR$^{40}$S(O)$_2$—NR$^{40}$-aryl, —NR$^{40}$S(O)$_2$—NR$^{40}$-heteroaryl, and —NR$^{40}$S(O)$_2$—NR$^{40}$-heterocyclyl, where each $R^{40}$ is independently selected from hydrogen or alkyl.

In certain embodiments of the above methods, $R^1$ is hydrogen.

In certain embodiments of the above methods, $R^2$ is hydrogen or alkyl.

In certain embodiments of the above methods, $R^3$ and $R^4$ are independently selected from the group consisting of hydrogen, alkyl, substituted alkyl, aryl, substituted aryl, heteroaryl, substituted heteroaryl, halo, hydroxy, cyano, —S(O)$_n$—N(R$^8$)—R$^8$, —NR$^8$C(O)NR$^8$R$^8$, and —X$^1$R$^8$;

where $X^1$ is oxygen, —S(O)$_n$—, or —NR$^9$—;

n is 0, 1, or 2;

each $R^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when $X^1$ is —SO— or —SO$_2$—, then $R^8$ is not hydrogen; and $R^9$ is selected from the group consisting of hydrogen, alkyl, and aryl;

or $R^3$ and $R^4$ together with the carbon atoms pendent thereto, form a cycloalkyl, substituted cycloalkyl, heterocyclyl, substituted heterocyclyl, aryl, substituted aryl, heteroaryl, or substituted heteroaryl.

In certain embodiments of the above methods, $R^3$ and $R^4$ are independently selected from the group consisting of hydrogen, alkyl, aryl, heteroaryl, hydroxy, —S(O)$_n$—N(R$^8$)—R$^8$, —NR$^8$C(O)NR$^8$R$^8$, and —X$^1$R$^8$; where $X^1$ is oxygen, —S(O)$_n$—, or —NR$^9$—;

n is 0, 1, or 2;

$R^8$ is aryl or substituted aryl; and $R^9$ is hydrogen, alkyl or aryl;

or $R^3$ and $R^4$ together with the carbon atoms pendent thereto, form a cycloalkyl, heterocyclyl, aryl, or heteroaryl.

In certain embodiments of the above methods, $R^3$ and $R^4$ are independently selected from the group consisting of hydrogen and —X$^1$R$^8$; where $X^1$ is oxygen, and $R^8$ is aryl or substituted aryl.

In certain embodiments of the above methods, $R^5$ and $R^6$ are independently selected from the group consisting of hydrogen, halo, alkyl, substituted alkyl, aryl, substituted aryl, heteroaryl, substituted heteroaryl and —X$^2$R$^{10}$;

where $X^2$ is oxygen, —S(O)$_n$—, or —NR$^{13}$—;

n is 0, 1, or 2;

$R^{10}$ is aryl or substituted aryl; and $R^{13}$ is selected from the group consisting of hydrogen, alkyl, and aryl.

In certain embodiments of the above methods, $R^5$ and $R^6$ are independently selected from the group consisting of hydrogen and —X$^2$R$^{10}$; where $X^2$ is oxygen, and $R^{10}$ is aryl or substituted aryl.

In certain embodiments of the above methods, $R^5$ and $R^6$ are hydrogen.

In certain embodiments of the above methods, $R^2$ is hydrogen or alkyl;

$R^3$ and $R^4$ are independently selected from the group consisting of hydrogen, alkyl, substituted alkyl, aryl, substituted aryl, heteroaryl, substituted heteroaryl, halo, hydroxy, cyano, —S(O)$_n$—N(R$^8$)—R$^8$, —NR$^8$C(O)NR$^8$R$^8$, and —X$^1$R$^8$;

where $X^1$ is oxygen, —S(O)$_n$—, or —NR$^9$—;

n is 0, 1, or 2;

each $R^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when $X^1$ is —SO— or —SO$_2$—, then $R^8$ is not hydrogen; and $R^9$ is selected from the group consisting of hydrogen, alkyl, and aryl;

or $R^3$ and $R^4$ together with the carbon atoms pendent thereto, form a cycloalkyl, substituted cycloalkyl, heterocyclyl, substituted heterocyclyl, aryl, substituted aryl, heteroaryl, or substituted heteroaryl; and $R^5$ and $R^6$ are independently selected from the group consisting of hydrogen, halo, alkyl, substituted alkyl, aryl, substituted aryl, heteroaryl, substituted heteroaryl and —X$^2$R$^{10}$;

where $X^2$ is oxygen, —S(O)$_n$—, or —NR$^{13}$—;

n is 0, 1, or 2;

$R^{10}$ is aryl or substituted aryl; and

R[13] is selected from the group consisting of hydrogen, alkyl, and aryl.

In certain embodiments of the above methods,

R[2] is hydrogen or alkyl;

R[3] and R[4] are independently selected from the group consisting of hydrogen, alkyl, aryl, heteroaryl, hydroxy, —S(O)$_n$—N(R[8])—R[8], —NR[8]C(O)NR[8]R[8], and —X[1]R[8]; where X[1] is oxygen, —S(O)$_n$—, or —NR[9]—;

n is 0, 1, or 2;

R[8] is aryl or substituted aryl; and

R[9] is hydrogen, alkyl or aryl;

or R[3] and R[4] together with the carbon atoms pendent thereto, form a cycloalkyl, heterocyclyl, aryl, or heteroaryl; and R[5] and R[6] are independently selected from the group consisting of hydrogen and —X[2]R[10]; where X[2] is oxygen, and R[10] is aryl or substituted aryl.

In certain embodiments of the above methods,

R[2] is hydrogen or alkyl;

R[3] and R[4] are independently selected from the group consisting of hydrogen and —X[1]R[8]; where X[1] is oxygen, and R[8] is aryl or substituted aryl; and R[5] and R[6] are hydrogen.

In certain embodiments of the above methods, R[11] is $C_1$ to $C_4$ alkyl.

In certain embodiments of the above methods, R[11] is methyl.

In certain embodiments of the above methods, R[12] is $C_1$ to $C_4$ alkyl.

In certain embodiments of the above methods, R[12] is methyl.

In certain embodiments of the methods disclosed hereinabove, the methods further comprise the step of forming a corresponding salt of the compound. Such methods are well known in the art.

Other modifications to arrive at compounds of this invention are well within the skill of the art. For example, modification of the C-4 hydroxy group may be done by conventional means to corresponding ethers, acyloxy etc. to provide compounds of the invention. Specifically, esters can be prepared under standard coupling conditions by reacting a carboxylic acid containing compound with a compound comprising an alcohol in a suitable solvent, optionally at elevated temperatures. Accordingly, esters of the compounds disclosed herein can be formed at any carboxylic acid or hydroxyl functional group. Typical ester forming reactions to provide the compounds of the invention are shown below, where R[2] is as defined herein.

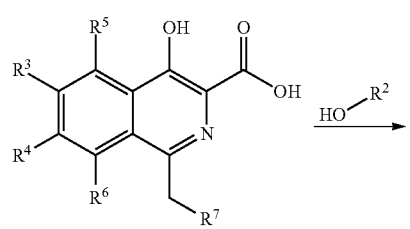

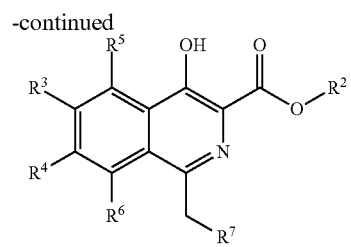

The N-oxide derivatives of the above described compounds can also be prepared using methods known within the skill of the art. Accordingly, compounds of the invention include N-oxide derivatives of the formula:

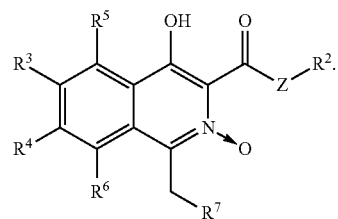

Compounds of the Invention

In another aspect, the invention is directed to a compound of formula VIII:

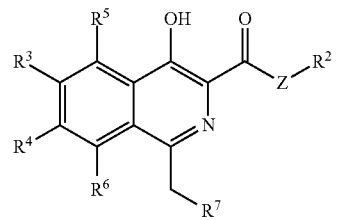

VIII wherein:

Z is O, NR[1], or S;

R[1] is selected from the group consisting of hydrogen and alkyl;

R[2] is selected from the group consisting of hydrogen and alkyl which is unsubstituted or substituted with one or more substituents independently selected from the group consisting of cycloalkyl, heterocyclyl, aryl, and heteroaryl;

R[3] and R[4] are independently selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, —S(O)$_n$—N(R[8])—R[8], —NR[8]C(O)NR[8]R[8], and —X[1]R[8];

where X[1] is oxygen, —S(O)$_n$—, or —NR[9]—;

n is 0, 1, or 2;

each R[8] is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when X[1] is —SO or —SO$_2$—, then R[8] is not hydrogen; and $R^9$ is selected from the group consisting of hydrogen, alkyl, and aryl;

or $R^3$ and $R^4$ together with the carbon atoms pendent thereto, form a cycloalkyl, substituted cycloalkyl, heterocyclyl, substituted heterocyclyl, aryl, substituted aryl, heteroaryl, or substituted heteroaryl;

$R^5$ and $R^6$ are independently selected from the group consisting of hydrogen, halo, alkyl, substituted alkyl, alkoxy, substituted alkoxy, aryl, substituted aryl, heteroaryl, substituted heteroaryl and $-X^2R^{10}$;

where $X^2$ is oxygen, $-S(O)_n-$, or $-NR^{13}-$;

n is 0, 1, or 2;

$R^{10}$ is selected from the group consisting of alkyl, substituted alkyl, aryl, substituted aryl, heteroaryl, substituted heteroaryl, heterocyclyl and substituted heterocyclyl; and $R^{13}$ is selected from the group consisting of hydrogen, alkyl, and aryl;

or when $X^2$ is $-NR^{13}-$, then $R^{10}$ and $R^{13}$, together with the nitrogen atom to which they are bound, can be joined to form a heterocyclyl or substituted heterocyclyl group; and $R^7$ is either $-N(R^{11})(R^{11})$ or $-OC(O)R^{12}$;

each $R^{11}$ is independently selected from alkyl, benzyl or aryl, or two $R^{11}$ together with the nitrogen atom to which they are attached form a 4-8 membered heterocyclyl or a heteroaryl; and $R^{12}$ is selected from the group consisting of alkyl, aryl, heteroaryl, and heterocyclyl;

or a salt, ester, stereoisomer, or mixture of stereoisomers thereof;

provided that the compound is not 1-dimethylaminomethyl-4-hydroxy-7-phenylsulfanyl-isoquinoline-3-carboxylic acid butyl ester.

In certain embodiments, the present invention is directed to a compound of formula VIIIA:

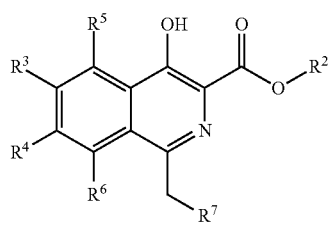

VIIIA wherein:

$R^2, R^3, R^4, R^5, R^6, R^7, R^8, R^9, R^{10}, R^{11}, R^{12}, R^{13}$, n, $X^1$ and $X^2$ are as defined for formula VIII above;

or a salt, ester, stereoisomer, or mixture of stereoisomers thereof;

provided that the compound is not 1-dimethylaminomethyl-4-hydroxy-7-phenylsulfanyl-isoquinoline-3-carboxylic acid butyl ester.

In certain embodiments of the above compounds, $R^2$ is hydrogen, alkyl, or substituted alkyl.

In certain embodiments, $R^2$ is alkyl.

In certain embodiments, $R^3$ and $R^4$ are independently selected from the group consisting of hydrogen, alkyl, cycloalkyl, aryl, heteroaryl, hydroxy, $-S(O)_n-N(R^8)-R^8$, $-NR^8C(O)NR^8R^8$, and $-X^1R^8$; where $X^1$ is oxygen, $-S(O)_n-$, or $-NR^9-$;

n is 0, 1, or 2;

$R^8$ is aryl or substituted aryl, and $R^9$ is hydrogen, alkyl, or aryl;

or $R^3$ and $R^4$ together with the carbon atoms pendent thereto, form a cycloalkyl, heterocyclyl, aryl, or heteroaryl.

In certain embodiments, $R^5$ and $R^6$ are hydrogen.

In certain embodiments, $R^2$ is alkyl which is unsubstituted or substituted with one or more substituents independently selected from the group consisting of cycloalkyl, heterocyclyl, aryl, and heteroaryl; and $R^5$ and $R^6$ are hydrogen.

In certain embodiments, $R^7$ is $-OC(O)R^{12}$. In certain embodiments, $R^7$ is $-N(R^{11})(R^{11})$. In certain embodiments, $R^7$ is $-N(R^{11})(R^{11})$; and $R^{11}$ is $C_1$ to $C_4$ alkyl. In certain embodiments, $R^7$ is $-OC(O)R^{12}$; and $R^{12}$ is $C_1$ to $C_4$ alkyl.

In certain embodiments, Z is O.

In certain embodiments of the compounds disclosed hereinabove, each of $R^3, R^4, R^5, R^6, R^8$, and $R^{10}$ are as defined below:

$R^3$ and $R^4$ are independently selected from the group consisting of hydrogen, alkyl, cycloalkyl, heterocyclyl, aryl, heteroaryl, halo, hydroxy, cyano, $-S(O)_n-N(R^8)-R^8$, $-NR^8C(O)NR^8R^8$, and $-X^1R^8$; where $X^1$ is oxygen, $-S(O)_n-$, or $-NR^9-$;

n is 0, 1, or 2;

each $R^8$ is independently selected from the group consisting of hydrogen, alkyl, aryl, cycloalkyl, heteroaryl, and heterocyclyl; and $R^9$ is selected from the group consisting of hydrogen, alkyl, and aryl;

or $R^3$ and $R^4$ together with the carbon atoms pendent thereto, form a cycloalkyl, heterocyclyl, aryl, or heteroaryl;

$R^5$ and $R^6$ are independently selected from the group consisting of hydrogen, halo, alkyl, alkoxy, aryl, heteroaryl, and $-X^2R^{10}$; where $X^2$ is oxygen, $-S(O)_n-$, or $-NR^{13}-$;

n is 0, 1, or 2;

$R^{10}$ is selected from the group consisting of alkyl, aryl, heteroaryl, and heterocyclyl; and $R^{13}$ is selected from the group consisting of hydrogen, alkyl, and aryl;

or when $X^2$ is $-NR^{13}-$, then $R^{10}$ and $R^{13}$, together with the nitrogen atom to which they are bound, can be joined to form a heterocyclyl group;

wherein each alkyl, alkoxy, cycloalkyl, heterocyclyl, aryl, heteroaryl, and heterocyclyl described above can be optionally substituted with from 1 to 3 $R^{100}$, wherein each $R^{100}$ is independently selected from the group consisting of alkoxy, acyl, acylamino, acyloxy, amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl ester, cycloalkyl, thio, alkylthio, arylthio, cycloalkylthio, heteroarylthio, heterocyclicheterocyclylthio, sulfonyl, heteroaryl, heterocyclicheterocyclyl, cycloalkoxy, heteroaryloxy, heterocyclyloxy, oxycarbonylamino, oxythiocarbonylamino, $-OS(O)_2$-alkyl, $-OS(O)_2$-aryl, $-OS(O)_2$-heteroaryl, $-OS(O)_2$-heterocyclyl, $-OSO_2-NR^{40}R^{40}$, $-NR^{40}S(O)_2-NR^{40}$-alkyl, $-NR^{40}S(O)_2-NR^{40}$-aryl, $-NR^{40}S(O)_2-NR^{40}$-heteroaryl, and $-NR^{40}S(O)_2-NR^{40}$-heterocyclyl, where each $R^{40}$ is independently selected from hydrogen or alkyl;

provided that the compound is not 1-dimethylaminomethyl-4-hydroxy-7-phenylsulfanyl-isoquinoline-3-carboxylic acid butyl ester.

In another aspect, the invention is directed to 4-hydroxy-7-phenoxyisoquinoline-3-carboxylic acid methyl ester (3a):

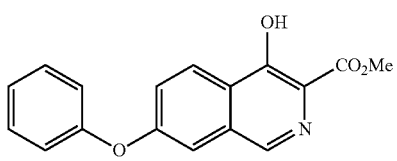

In another aspect, the invention is directed to methyl 4-hydroxy-1-methyl-7-phenoxyisoquinoline-3-carboxylate (3e):

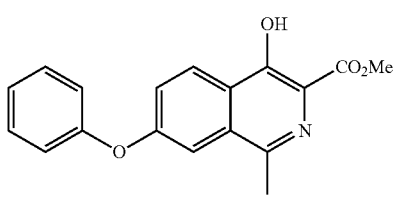

Isoquinoline Synthesis

The compounds and methods of the invention can be used for the synthesis of various isoquinoline compounds. Such compounds are known to be useful for inhibiting HIF hydroxylase activity, thereby increasing the stability and/or activity of hypoxia inducible factor (HIF), and can be used to treat and prevent HIF-associated conditions and disorders (see, e.g., U.S. Pat. No. 7,323,475). Exemplary substituted isoquinoline compounds which can be prepared using the methods disclosed herein include those represented by formula X:

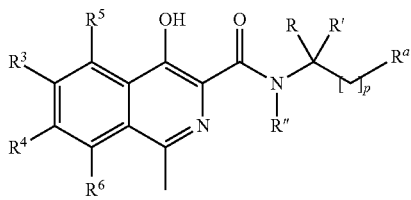

wherein $R^3$, $R^4$, $R^5$ and $R^6$ are as defined for formula I above and:

p is 0 when $R^a$ is —COOH; p is 1 when $R^a$ is —$WR^{18}$;

W is selected from the group consisting of oxygen, —$S(O)_n$— and —$NR^{19}$— where n is 0, 1, or 2, $R^{19}$ is selected from the group consisting of hydrogen, alkyl, substituted alkyl, acyl, aryl, substituted aryl, heteroaryl, substituted heteroaryl, heterocyclyl and substituted heterocyclyl and $R^{18}$ is selected from the group consisting of hydrogen, alkyl, substituted alkyl, aryl, substituted aryl, heteroaryl, substituted heteroaryl, heterocyclyl and substituted heterocyclyl, or when W is —$NR^{19}$— then $R^{18}$ and $R^{19}$, together with the nitrogen atom to which they are bound, can be joined to form a heterocyclyl or a substituted heterocyclyl group;

R is selected from the group consisting of hydrogen, deuterium and methyl;

R' is selected from the group consisting of hydrogen, deuterium, alkyl and substituted alkyl; alternatively, R and R' and the carbon pendent thereto can be joined to form cycloalkyl, substituted cycloalkyl, heterocyclyl or substituted heterocyclyl group;

R" is selected from the group consisting of hydrogen and alkyl or R" together with R' and the nitrogen pendent thereto can be joined to form a heterocyclyl or substituted heterocyclyl group;

and pharmaceutically acceptable salts, stereoisomers, mixture of stereoisomers, and esters thereof.

Exemplary methods for the preparation of compounds described herein are shown in the Schemes below, where Z, $X^3$, $R^2$, $R^3$, $R^4$, $R^5$, $R^6$, $R^{11}$, $R^{12}$, p, $R^a$, R, R' and R" are as defined for formula I and formula X above, and PG is a standard amine protecting group.

Scheme A

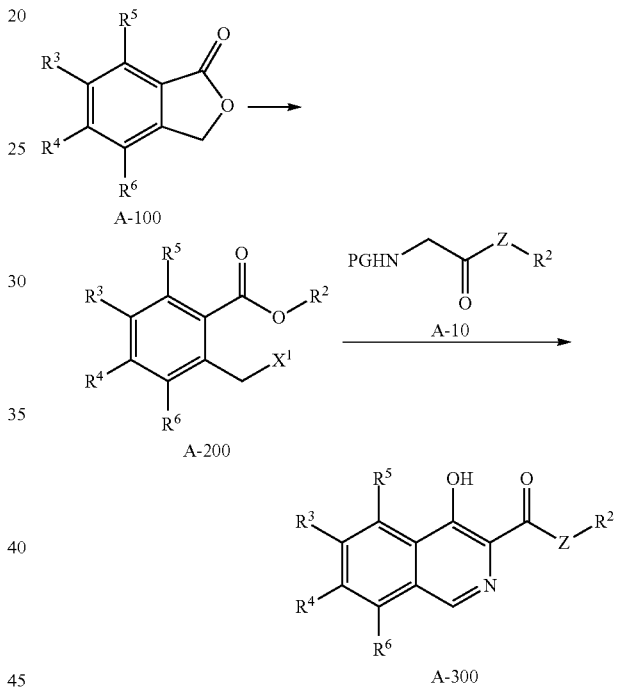

Compounds A-200 for use in the reactions depicted in Scheme A, can be prepared by contacting compounds A-100 with a suitable Lewis acid such as trimethyl borate, in the presence of a halogenating agent, such as dichlorotriphenylphosphorane and thionyl chloride to generate the acyl halide, which upon contact with an alcohol of the formula $R^2$—OH, such as methanol, yields the corresponding halogenated ester A-200. Upon reaction completion, A-200 can be recovered by conventional techniques such as neutralization, extraction, precipitation, chromatography, filtration, and the like; or, alternatively, used in the next step without purification and/or isolation.

Compounds A-200 can be modified to A-300 (formula II) by contacting A-200 with about a stoichiometric amount of a suitable alpha-amino acid of formula A-10 (wherein PG refers to a suitable protecting group such as mesyl, tosyl, etc.) and a catalytic amount of sodium iodide. The reaction is conducted under conventional coupling conditions well known in the art. A suitable base is then added, such as sodium methoxide, sodium ethoxide or another suitable base in methanol, DMF or another suitable solvent. The reaction is continued until it is substantially complete which typically occurs within about 1 to 72 h. Upon reaction completion, the compounds A-300 can be recovered by conventional techniques such as neutralization, extraction, precipitation, chromatography, filtration and the like.

Compounds A-300 can be modified to B-100 (formula I) by the methods of the present invention as shown in Scheme B.

Scheme B

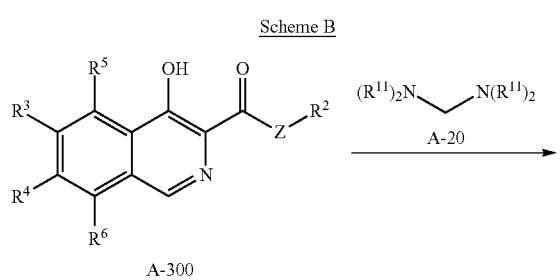

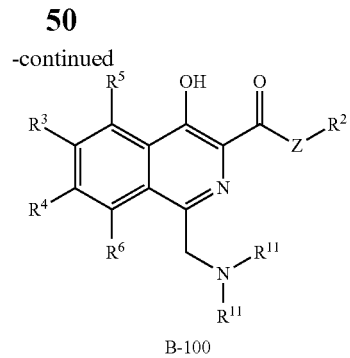

B-100

For example, contacting A-300 with about a stoichiometric amount or a slight excess thereof of a compound of formula A-20 (formula III) in the presence of an acid, such as acetic acid, provides compounds B-100. The reaction is continued until it is substantially complete which typically occurs within about 1 to 72 h. Upon reaction completion, the compounds B-100 may be recovered by conventional techniques such as neutralization, extraction, precipitation, chromatography, filtration and the like, or used in the next step without isolation and/or purification.

Compounds B-100 (formula I) can be modified to compounds C-100 (formula VII) and C-200 (formula IV) by the methods of the present invention as shown in Scheme C.

Scheme C

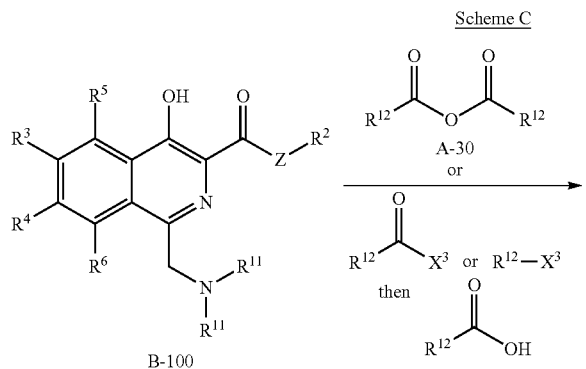

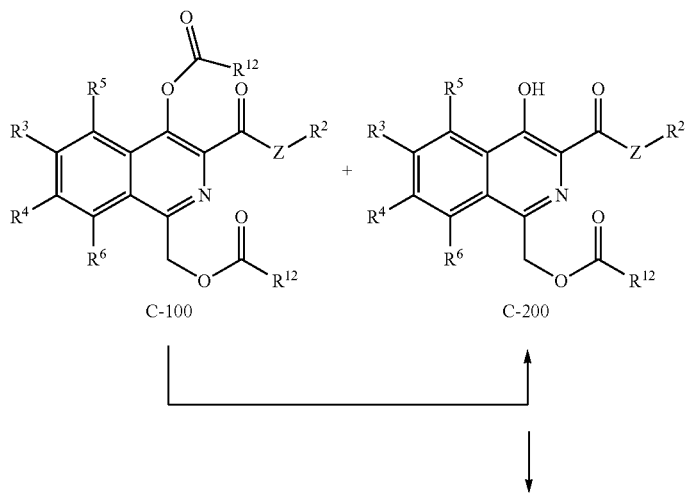

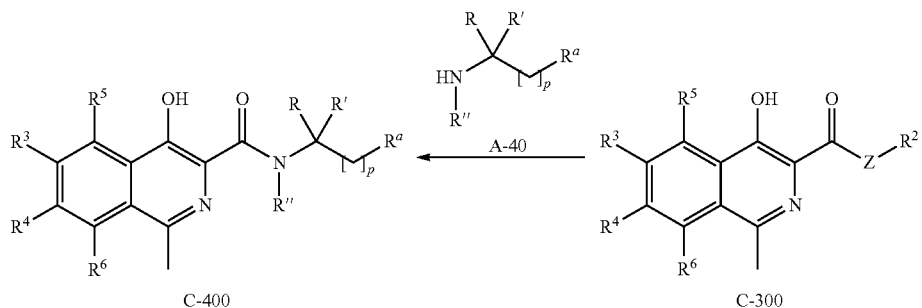

For example, contacting B-100 with an excess (e.g. 2-3 equivalents) of compound A-30 (formula V) in the presence of an acid, such as acetic acid, provides compounds C-100 and C-200. Alternatively, contacting B-100 with an acyl halide of formula $R^{12}$—$C(O)X^3$ or an alkyl halide of formula $R^{12}$—$X^3$, followed by an acid of formula $R^{12}$—$C(O)OH$, such as acetic acid, provides compounds C-100 and C-200. The reaction is typically conducted at temperatures of about 100° C., and is continued until it is substantially complete which typically occurs within about 1 to 72 h. Compounds C-200 can be provided by the methods of the present invention, such as reaction of the mixture of compounds C-100 and C-200 with an amine, such as morpholine in a suitable polar solvent, such as DMF. The reaction is typically performed at temperatures below room temperature (i.e. 0 to 10° C.). Upon reaction completion, the compounds C-200 can be recovered by conventional techniques such as neutralization, extraction, precipitation, chromatography, filtration and the like.

Compounds C-200 (formula IV) can be modified to C-300 (formula VI) under reaction conditions according to the present invention. In certain embodiments, the reaction conditions are hydrogenation reaction conditions. Such conditions typically comprise a catalyst, such as a palladium catalyst (e.g. palladium(0) on carbon), under a hydrogen atmosphere. In some embodiments, the hydrogenation reaction is conducted under pressure. In some embodiments, the hydrogenation reaction conditions comprise a base, such as sodium carbonate. In some embodiments, the hydrogenation reaction conditions comprise from about 0.5 to about 1 molar equivalents of sodium carbonate.

Compounds C-400 (formula X) can be synthesized by contacting compounds C-300 (formula VI) with at least a stoichiometric amount or an excess of a suitable amino acid or derivative thereof A-40 (particularly, but not limited to, glycine or its corresponding salts). The reaction is conducted under conventional coupling conditions well known in the art. In one embodiment, the reaction is conducted in the presence of sodium methoxide, sodium ethoxide or another suitable base in methanol, DMF or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compounds C-400 can be recovered by conventional techniques such as neutralization, extraction, precipitation, chromatography, filtration and the like.

Specific methods for the preparation of such substituted isoquinoline compounds are shown in Scheme D below, where $R^2$, $R^3$, $R^4$, $R^5$, $R^{11}$, $R^{12}$, p, $R^a$, R, R' and R" are as defined herein, and PG is a standard amine protecting group.

Scheme D

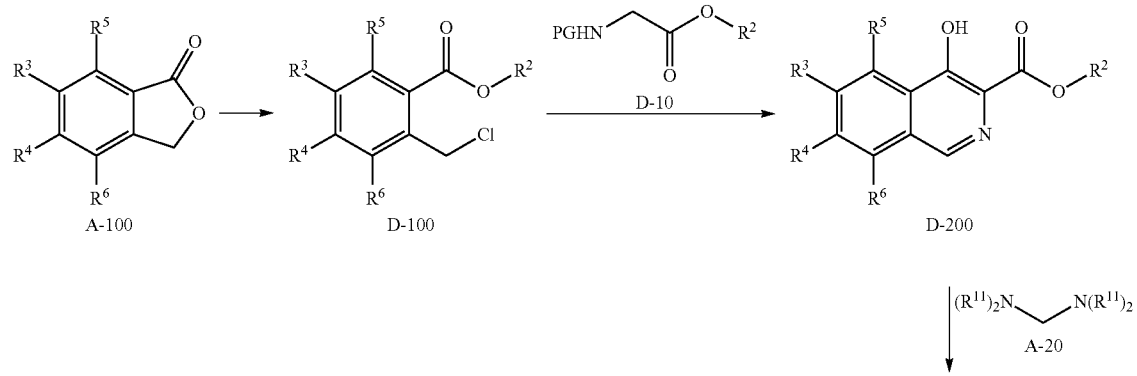

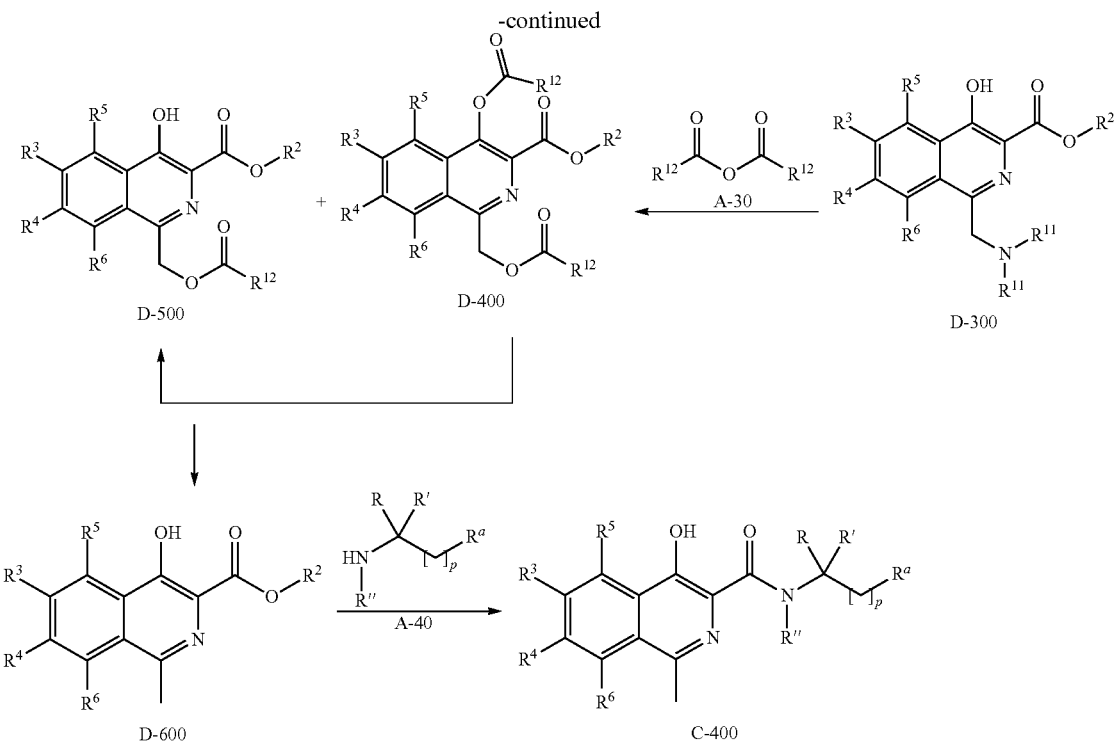

Compounds D-100 for use in the reactions depicted in Scheme D, can be prepared by contacting compounds A-100 with a suitable Lewis acid such as trimethyl borate, in the presence of dichlorotriphenylphosphorane and thionyl chloride to generate the acyl chloride, which upon contact with an alcohol, such as methanol, yields the corresponding ester D-100. Upon reaction completion, D-100 can be recovered by conventional techniques such as neutralization, extraction, precipitation, chromatography, filtration, and the like; or, alternatively, used in the next step without purification and/or isolation.

Compounds D-100 can be modified to D-200 (formula IIA) by contacting D-100 with about a stoichiometric amount of a suitable alpha-amino acid of formula D-10 (wherein PG refers to a suitable protecting group such as mesyl, tosyl, etc.) and a catalytic amount of sodium iodide. The reaction is conducted under conventional coupling conditions well known in the art. A suitable base is then added, such as sodium methoxide, sodium ethoxide or another suitable base in methanol, DMF or another suitable solvent. The reaction is continued until it is substantially complete which typically occurs within about 1 to 72 h. Upon reaction completion, the compounds D-200 can be recovered by conventional techniques such as neutralization, extraction, precipitation, chromatography, filtration and the like.

Compounds D-200 can be modified to D-300 (formula IA) by the methods of the present invention. For example, contacting D-200 with about a stoichiometric amount or a slight excess thereof of a compound of formula A-20 in the presence of an acid, such as acetic acid, provides compounds D-300. The reaction is continued until it is substantially complete which typically occurs within about 1 to 72 h. Upon reaction completion, the compounds D-300 can be recovered by conventional techniques such as neutralization, extraction, precipitation, chromatography, filtration and the like.

Compounds D-300 can be modified to compounds D-400 (formula VIIA) and D-500 (formula WA) by the methods of the present invention. For example, contacting D-300 with an excess (e.g. 2-3 equivalents) of compound A-30 in the presence of an acid, such as acetic acid, provides compounds D-400 and D-500. The reaction is typically conducted at temperatures of about 100° C., and is continued until it is substantially complete which typically occurs within about 1 to 72 h. Compounds D-500 can be provided by the methods of the present invention, such as reaction of the mixture of compounds D-400 and D-500 with an amine, such as morpholine in a suitable polar solvent, such as DMF. The reaction is typically performed at temperatures below room temperature (e.g., 0 to 10° C.). Upon reaction completion, the compounds D-500 can be recovered by conventional techniques such as neutralization, extraction, precipitation, chromatography, filtration and the like.

Compounds D-500 can be modified to D-600 (formula VIA) under reaction conditions according to the present invention. In certain embodiments, the reaction conditions are hydrogenation reaction conditions. Such conditions typically comprise a catalyst, such as a palladium catalyst (e.g. palladium(0) on carbon), under a hydrogen atmosphere. In some embodiments, the hydrogenation reaction is conducted under pressure. In some embodiments, the hydrogenation reaction conditions comprise a base, such as sodium carbonate. In some embodiments, the hydrogenation reaction conditions comprise from about 0.5 to about 1 molar equivalents of sodium carbonate.

Compounds C-400 (formula X) can be synthesized by contacting compounds D-600 with at least a stoichiometric amount or an excess of a suitable amino acid or derivative thereof A-40 (particularly, but not limited to, glycine or its corresponding salts). The reaction is conducted under conventional coupling conditions well known in the art. In one embodiment, the reaction is conducted in the presence of sodium methoxide, sodium ethoxide or another suitable base in methanol, DMF or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compounds C-400 can be recovered by conventional techniques such as neutralization, extraction, precipitation, chromatography, filtration and the like.

The compounds A-100, A-10, A-20, A-30, A-40, and D-10 for use in the reactions depicted in the above Schemes are either available from commercial sources or can be prepared according to known literature procedures. Other modifications to the compounds provided by this invention are well within the skill of the art. For example, modification of the C-4 hydroxy group may be done by conventional means to corresponding ethers, acyloxy, and the like. In addition, compounds A-40 can be used as provided in U.S. Pat. No. 7,323,475.

In the art, isoquinoline compounds have been prepared according to methods which are not desirable for large scale production (Scheme E, where $R^{20}$ is a general abbreviation that represents a substituent group as described herein (i.e., alkyl, alkoxy, aryl, aryloxy, etc)). Exemplary substituent groups include alkyl, alkoxy, heteroalkyl, aryl, aryloxy, etc., each as defined herein. For example, isoquinoline compounds prepared according to U.S. Pat. No. 7,323,475 involve the undesirable chromatographic separation of regioisomers E-200 and E-300. It is contemplated that such a process would be inefficient on a large scale. In addition, the conversion of E-400 to the corresponding bromide E-500 in order to furnish the alkyl substitution on the isoquinoline ring of compounds E-600 requires the use of phosphorus oxybromide which is both toxic and potentially explosive. Advantageously, in contrast to methods previously disclosed, the methods of the present invention do not require the use of such hazardous reagents for the synthesis of isoquinoline compounds.

Scheme E

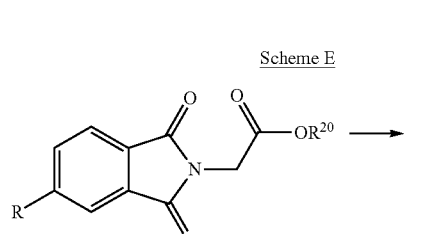

E-100

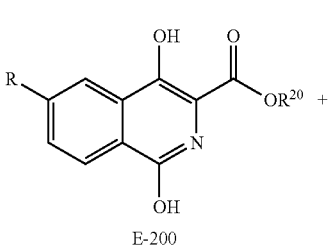

E-200

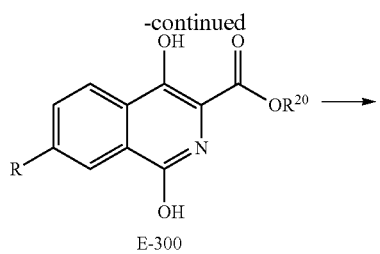

E-300

E-400

E-600          E-500

The synthesis of 1-dimethylaminomethyl-4-hydroxy-7-phenylsulfanyl-isoquinoline-3-carboxylic acid butyl ester has been reported in U.S. Pat. No. 7,323,475, using a mixture of 4-hydroxy-7-phenylsulfanyl-isoquinoline-3-carboxylic acid butyl ester, N,N-dimethylmethyleneammonium iodide, and potassium carbonate in anhydrous dichloromethane. However, only 16% of the desired 1-dimethylaminomethyl-4-hydroxy-7-phenylsulfanyl-isoquinoline-3-carboxylic acid butyl ester was obtained. Advantageously, in contrast to methods previously disclosed, the methods of the present invention provide good yields for the synthesis of compounds described herein.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius (° C.). Also, in these examples and elsewhere, abbreviations have the following meanings:

EtOH=Ethanol
Et=Ethyl
g=Gram
h=Hour

HPLC=High-performance liquid chromatography
L=Liter
MeOH=Methanol
mg=Milligram
min=Minute
mL=Milliliter
mM=Millimolar
mmol=Millimole
Ac=Acetyl
NaOMe=Sodium methoxide Example 1

Preparation of 2-(4-hydroxy-1-methyl-5-phenoxyisoquinoline-3-carboxamido)acetic acid a) Preparation of methyl 1-((dimethylamino)methyl)-4-hydroxy-5-phenoxyisoquinoline-3-carboxylate (1b)

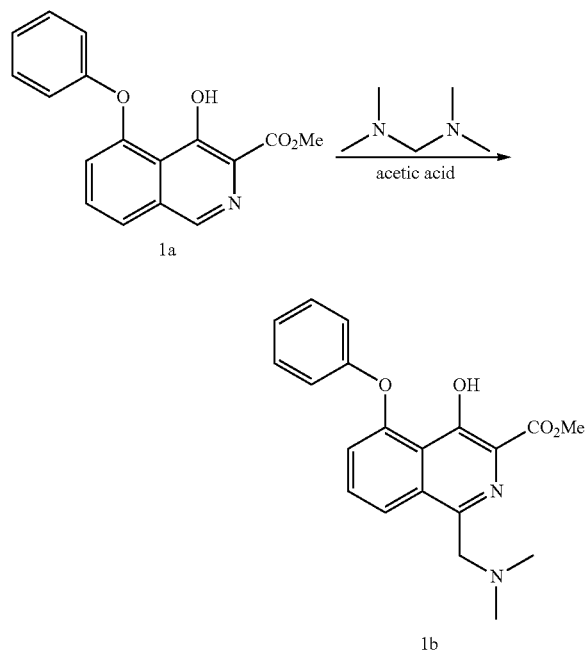

A round bottom flask fitted with thermocouple and condenser can be charged with 1a and acetic acid (about 7 molar equivalents±5%). The suspension of 1a in acetic acid can be stirred vigorously with magnetic stirring (note: overhead stirring should be done for larger scale work). A slight excess of bis-dimethylaminomethane (about 1.25 molar equivalents) can then be slowly added to the mixture [Note: Reaction is slightly exothermic, 15-20° C. temperature rise can be observed]. After the addition is complete, the mixture can be heated to 55±5° C. and maintained for at least 8 h. The reaction can then be evaluated by HPLC. If the amount of 1a is greater than 0.5%, the reaction can be stirred for additional 2 hours at 55±5° C. and reevaluated by HPLC.

b) Preparation of methyl 1-((acetoxy)methyl)-4-hydroxy-5-phenoxyisoquinoline-3-carboxylate (1c)

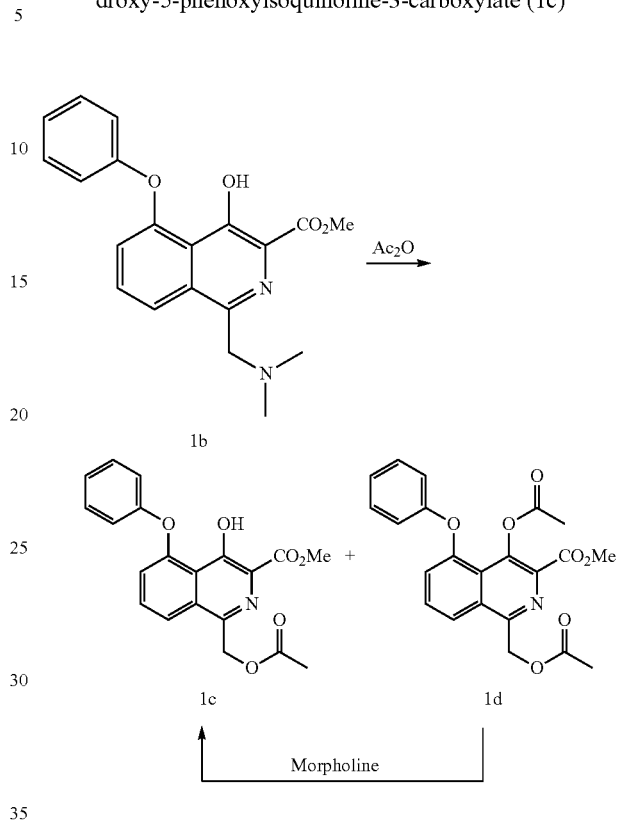

The solution of 1b from Example 1a) can be cooled to below 25° C., at which time acetic anhydride (about 3 molar equivalents) can be added slowly at a temperature below 50° C. [Note: Reaction is exothermic, 20-25° C. temperature rise can be observed. Rate of addition is important to control the exothermic reaction between acetic anhydride and dimethyl amine of 1b. Excess heat generated will cause unsafe rapid evolution of gaseous dimethyl amine]. After the addition is complete, the mixture can be heated to 100±5° C. for 20-24 hours. The reaction can then be evaluated by HPLC. If 1b is in an amount greater than 2%, the reaction can be stirred for an additional 2 hours and then reevaluated by HPLC.

1d can be converted to 1c by the following procedure. The solution of 1c and 1d from the above procedure can be cooled to less than 65±5° C. with good mixing. If the reaction temperature goes below 30° C., the reaction may solidify. Water can be slowly and steadily added (the first half can be added over 1 hour and the rest added over 30 minutes). The mixture can then be cooled and stirred at 20±5° C. for at least 3 hours, at which time the mixture can be filtered and the wet cake washed with water (3×) and added to a round bottom flask fitted with a mechanical stirrer. Dichloromethane and water (3:1 by volume) can be added and the mixture stirred for 30 minutes. The dichloromethane can be separated (without including the interface or aqueous layer) and the solution evaluated by HPLC.

1c can be further purified according to the following procedure. The above solution can be added to a flask, fitted with mechanical stirrer, and cooled to 5±5° C. Morpholine can be added and the mixture stirred at 5±5° C. for 30-60 minutes and evaluated by HPLC. If the amount of 1d is greater than 2%, the reaction can be stirred for an additional hour. Once the reaction reached completion, 1c can be precipitated from cold acetone/methanol solution, filtered, washed and dried under vacuum at 50±5° C.

c) Preparation of methyl 4-hydroxy-1-methyl-5-phenoxyisoquinoline-3-carboxylate (1e)

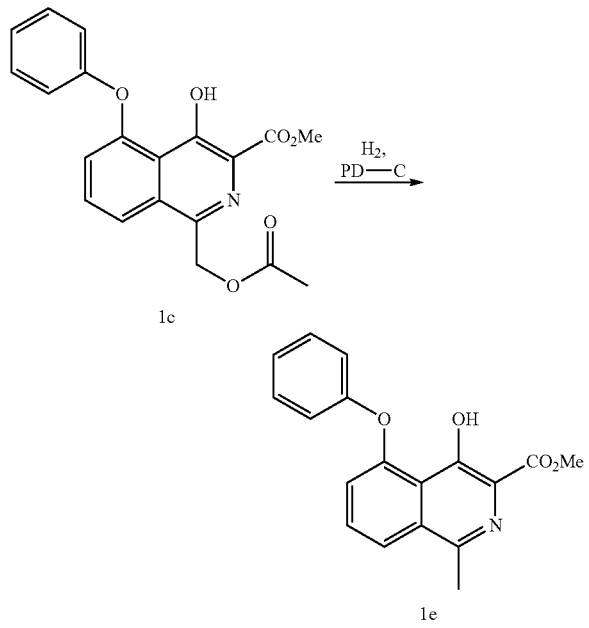

A glass lined Parr pressure reactor vessel equipped with a 4-blade impeller can be charged with 1c, Pd/C (about 0.4 to 0.5 molar equivalents), anhydrous $Na_2CO_3$ (about 0.5 molar equivalents), and ethyl acetate. The flask can then be vacuum-purged with nitrogen (3×) and vacuum-purged with hydrogen (3×). The flask can then be pressurized with hydrogen to set point 60 psi and stirred at 60° C. for 6-8 hrs until completion of reaction (1c <0.5%). The flask can then be cooled to 20-25° C., the pressure released to ambient, the head space purged with nitrogen three times and filtered through glass microfiber filter paper. The filtrate can be concentrated and precipitated from cold methanol and dried under vacuum at 50±5° C.

d) Preparation of 2-(4-hydroxy-1-methyl-5-phenoxyisoquinoline-3-carboxamido)acetic acid (1f)

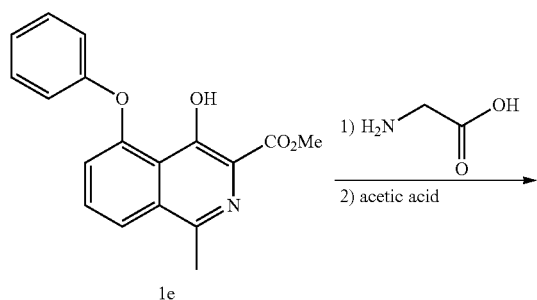

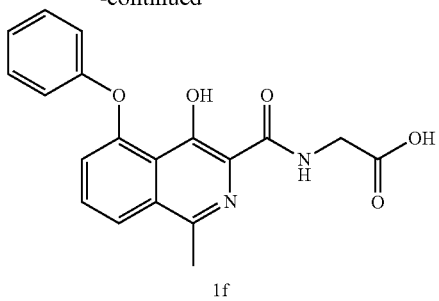

2-(4-Hydroxy-1-methyl-5-phenoxyisoquinoline-3-carboxamido)acetic acid can be prepared from 1e according to the following procedure.

A pressure glass reaction flask which included top threads for a screw cap lid can be fitted with a magnetic stirrer, charged with 1e, glycine (about 3 molar equivalents), methanol, and a sodium methoxide solution (with 1.2 molar eqivalents $NaOCH_3$) and sealed. The reaction can then be heated to 110° C. for at least 6 h during which time the reaction forms a yellow suspension. The reaction can then be cooled to 20-25° C. and evaluated by HPLC. The reaction can be continued until less than 1% 1e remains as determined by HPLC, filtered, washed with methanol, dried under vacuum, dissolved in water and extracted with ethyl acetate to remove impurities to below 0.1%. The ethyl acetate can be removed and an acetic acid solution (with 3 molar eqivalents acetic acid) can be added over one hour. The suspension can be stirred at room temperature for at least 3 hours, filtered, and the solid washed with water (3×), cold acetone (5-10° C., 2×) and evaluated for impurities by HPLC. If acetone removable impurities are present, the flask can be charged with acetone and refluxed for at least 8 h, slowly cooled to 5-10° C., stirred for at least 2-3 h, filtered, washed with cold acetone (5-10° C., 3×) and dried under vacuum to obtain 2-(4-hydroxy-1-methyl-5-phenoxyisoquinoline-3-carboxamido)acetic acid.

Example 2

Preparation of 2-(4-hydroxy-1-methyl-6-phenoxyisoquinoline-3-carboxamido)acetic acid a) Preparation of methyl 1-((dimethylamino)methyl)-4-hydroxy-6-phenoxyisoquinoline-3-carboxylate (2b)

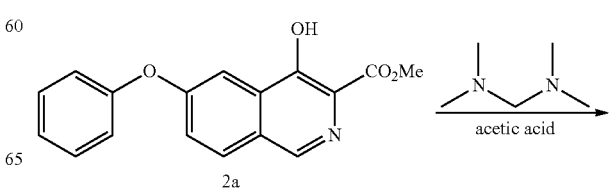

-continued

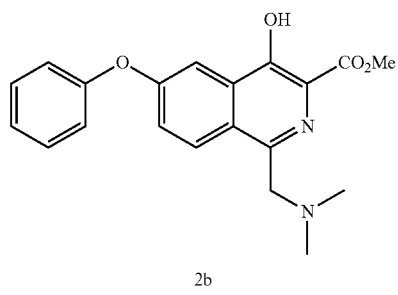

A round bottom flask fitted with thermocouple and condenser can be charged with 2a and acetic acid (about 7 molar equivalents±5%). The suspension of 2a in acetic acid can be stirred vigorously with magnetic stirring (note: overhead stirring should be done for larger scale work). A slight excess of bis-dimethylaminomethane (about 1.25 molar equivalents) can then be slowly added to the mixture [Note: Reaction is slightly exothermic, 15-20° C. temperature rise can be observed]. After the addition is complete, the mixture can be heated to 55±5° C. and maintained for at least 8 h. The reaction can then be evaluated by HPLC. If the amount of 2a is greater than 0.5%, the reaction can be stirred for additional 2 hours at 55±5° C. and reevaluated by HPLC.

b) Preparation of methyl 1-((acetoxy)methyl)-4-hydroxy-6-phenoxyisoquinoline-3-carboxylate (2c)

The solution of 2b from Example 2a) can be cooled to below 25° C., at which time acetic anhydride (about 3 molar equivalents) can be added slowly at a temperature below 50° C. [Note: Reaction is exothermic, 20-25° C. temperature rise can be observed. Rate of addition is important to control the exothermic reaction between acetic anhydride and dimethyl amine or 2b. Excess heat generated will cause unsafe rapid evolution of gaseous dimethyl amine]. After the addition is complete, the mixture can be heated to 100±5° C. for 20-24 hours. The reaction can then be evaluated by HPLC. If 2b is in an amount greater than 2%, the reaction can be stirred for an additional 2 hours and then reevaluated by HPLC.

2d can be converted to 2c by the following procedure. The solution of 2c and 2d from the above procedure can be cooled to less than 65±5° C. with good mixing. If the reaction temperature goes below 30° C., the reaction may solidify. Water can be slowly and steadily added (the first half can be added over 1 hour and the rest added over 30 minutes). The mixture can then be cooled and stirred at 20±5° C. for at least 3 hours, at which time the mixture can be filtered and the wet cake washed with water (3x) and added to a round bottom flask fitted with a mechanical stirrer. Dichloromethane and water (3:1 by volume) can be added and the mixture stirred for 30 minutes. The dichloromethane can be separated (without including the interface or aqueous layer) and the solution evaluated by HPLC.

2c can be further purified according to the following procedure. The above solution can be added to a flask, fitted with mechanical stirrer, and cooled to 5±5° C. Morpholine can be added and the mixture stirred at 5±5° C. for 30-60 minutes and evaluated by HPLC. If the amount of 2d is greater than 2%, the reaction can be stirred for an additional hour. Once

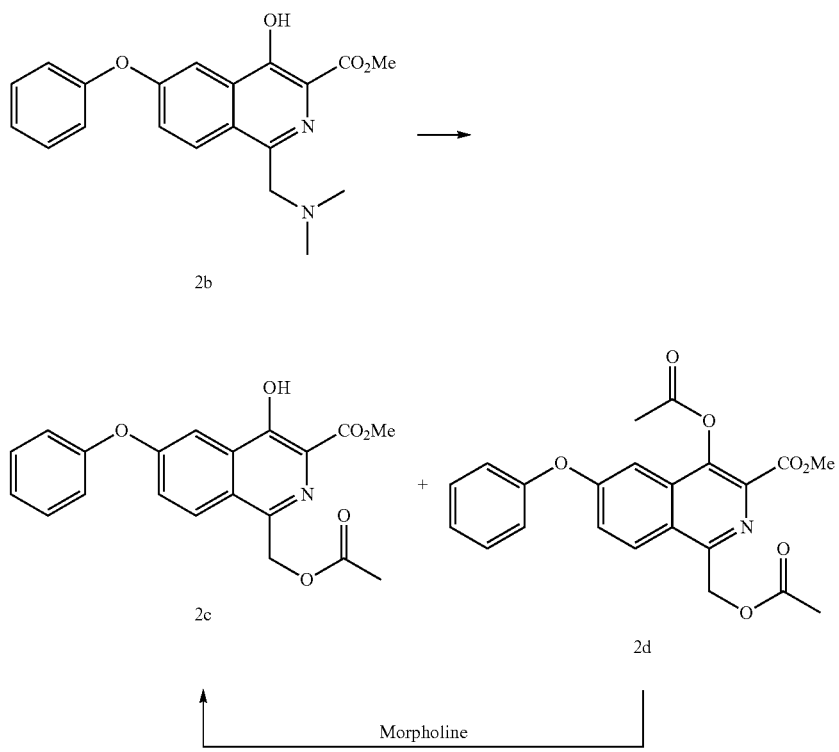

the reaction reached completion, 2c can be precipitated from cold acetone/methanol solution, filtered, washed and dried under vacuum at 50±5° C.

c) Preparation of methyl 4-hydroxy-1-methyl-6-phenoxyisoquinoline-3-carboxylate (2e)

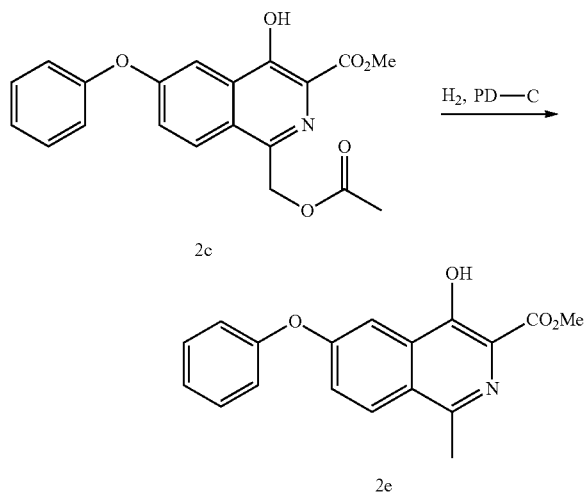

A glass lined Parr pressure reactor vessel equipped with a 4-blade impeller can be charged with 2c, Pd/C (about 0.4 to 0.5 molar equivalents), anhydrous $Na_2CO_3$ (about 0.5 molar equivalents), and ethyl acetate. The flask can then be vacuum-purged with nitrogen (3×) and vacuum-purged with hydrogen (3×). The flask can then be pressurized with hydrogen to set point 60 psi and stirred at 60° C. for 6-8 hrs until completion of reaction (2c <0.5%). The flask can then be cooled to 20-25° C., the pressure released to ambient, the head space purged with nitrogen three times and filtered through glass microfiber filter paper. The filtrate can be concentrated and precipitated from cold methanol and dried under vacuum at 50±5° C.

d) Preparation of 2-(4-hydroxy-1-methyl-6-phenoxyisoquinoline-3-carboxamido)acetic acid (2f)

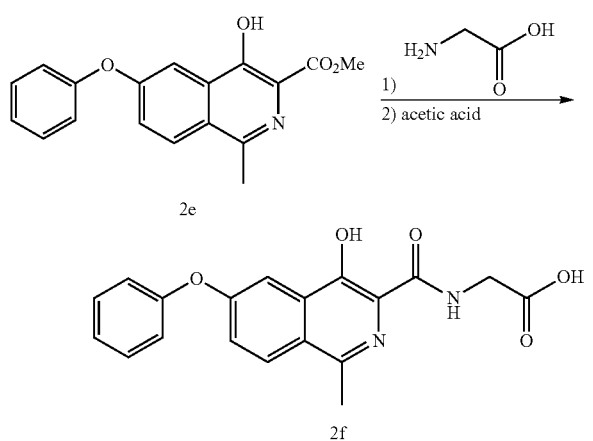

2-(4-Hydroxy-1-methyl-6-phenoxyisoquinoline-3-carboxamido)acetic acid is prepared from 2e according to the following procedure.

A pressure glass reaction flask which included top threads for a screw cap lid can be fitted with a magnetic stirrer, charged with 2e, glycine (about 3 molar equivalents), methanol, and a sodium methoxide solution (with 1.2 molar eqivalents $NaOCH_3$) and sealed. The reaction can then be heated to 110° C. for at least 6 h during which time the reaction forms a yellow suspension. The reaction can then be cooled to 20-25° C. and evaluated by HPLC. The reaction can be continued until less than 1% 2e remains as determined by HPLC, filtered, washed with methanol, dried under vacuum, dissolved in water and extracted with ethyl acetate to remove impurities to below 0.1%. The ethyl acetate can be removed and an acetic acid solution (with 3 molar eqivalents acetic acid) can be added over one hour. The suspension can be stirred at room temperature for at least 3 hours, filtered, and the solid washed with water (3×), cold acetone (5-10° C., 2×) and evaluated for impurities by HPLC. If acetone removable impurities are present, the flask can be charged with acetone and refluxed for at least 8 h, slowly cooled to 5-10° C., stirred for at least 2-3 h, filtered, washed with cold acetone (5-10° C., 3×) and dried under vacuum to obtain 2-(4-hydroxy-1-methyl-6-phenoxyisoquinoline-3-carboxamido)acetic acid.

Example 3

Preparation of 2-(4-hydroxy-1-methyl-7-phenoxyisoquinoline-3-carboxamido)acetic acid a) Preparation of 5-phenoxyphthalide

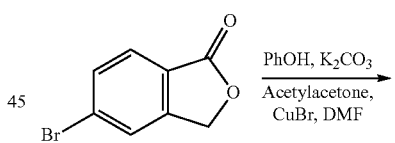

A reactor was charged with DMF (68 Kg), and stirring was initiated. The reactor was then charged with phenol (51 Kg), acetylacetone (8 Kg), 5-bromophthalide (85 Kg), copper bromide (9 Kg), and potassium carbonate (77 Kg). The mixture was heated above 85° C. and maintained until reaction completion and then cooled. Water was added. Solid was filtered and washed with water. Solid was dissolved in dichloromethane, and washed with aqueous HCl and then with water. Solvent was removed under pressure and methanol was added. The mixture was stirred and filtered. Solid was washed with methanol and dried in an oven giving 5-phenoxyphthalide (Yield: 72%, HPLC: 99.6%).

b) Preparation of 2-chloromethyl-4-phenoxybenzoic acid methyl ester

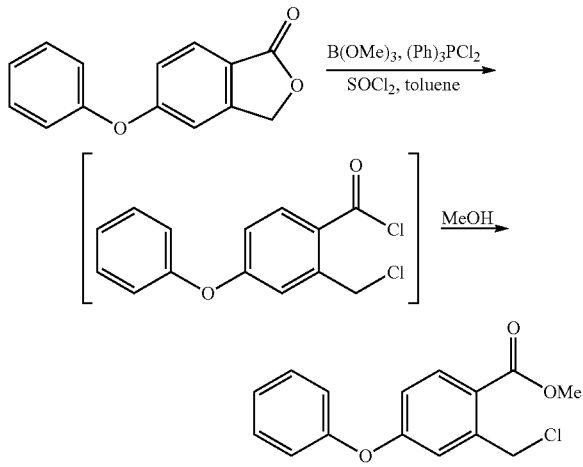

A reactor was charged with toluene (24 Kg), and stirring was initiated. The reactor was then charged with 5-phenoxyphthalide (56 Kg), thionyl chloride (41 Kg), trimethyl borate (1 Kg), dichlorotriphenylphosphorane (2.5 Kg), and potassium carbonate (77 Kg). The mixture was heated to reflux until reaction completion and solvent was removed leaving 2-chloromethyl-4-phenoxybenzoyl chloride. Methanol was charged and the mixture was heated above 50° C. until reaction completion. Solvent was removed and replaced with DMF. This solution of the product methyl 2-chloromethyl-4-phenoxybenzoic acid methyl ester in DMF was used directly in the next step (HPLC: 85%).

c) Preparation of 4-hydroxy-7-phenoxyisoquinoline-3-carboxylic acid methyl ester (3a)

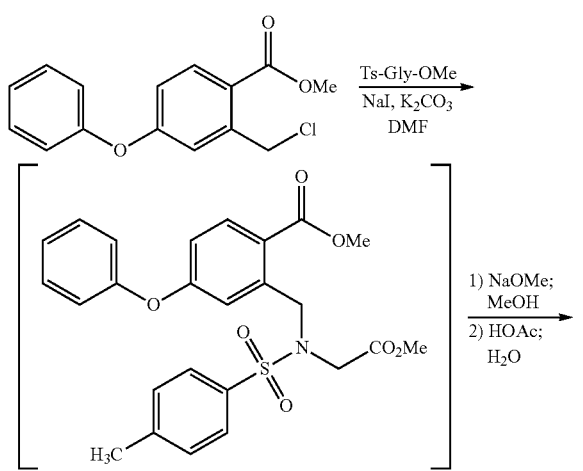

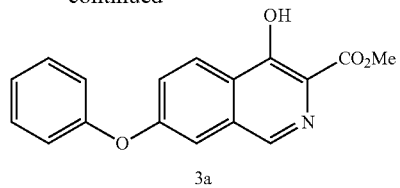

A reactor was charged with a solution of 2-chloromethyl-4-phenoxybenzoic acid methyl ester (~68 Kg) in DMF, and stirring was initiated. The reactor was then charged with p-toluenesulfonylglycine methyl ester (66 Kg), potassium carbonate (60 Kg), and sodium iodide (4 Kg). The mixture was heated to at least 50° C. until reaction completion. The mixture was cooled. Sodium methoxide in methanol was charged and the mixture was stirred until reaction completion. Acetic acid and water were added, and the mixture was stirred, filtered and washed with water. Solid was purified by acetone trituration and dried in an oven giving 3a (Yield from step b): 58%; HPLC: 99.4%). $^1$H NMR (200 MHz, DMSO-d6) δ 11.60 (s, 1 H), 8.74 (s, 1H), 8.32 (d, J=9.0 Hz, 1 H), 7.60 (dd, J=2.3 & 9.0 Hz, 1H), 7.49 (m, 3 H), 7.24 (m, 3 H), 3.96 (s, 3 H); MS-(+)-ion M+1=296.09 d) Preparation of methyl 1-((dimethylamino)methyl)-4-hydroxy-7-phenoxyisoquinoline-3-carboxylate (3b)

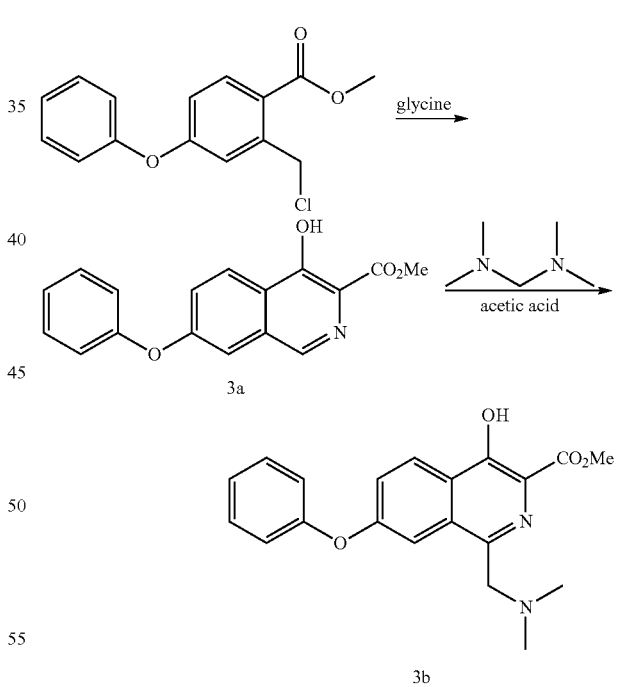

A flask was charged with 3a (29.5 g) and acetic acid (44.3 g±5%), and then stirred. Bis-dimethylaminomethane (12.8 g±2%) was slowly added. The mixture was heated to 55±5° C. and maintained until reaction completion. The reaction product was evaluated by MS, HPLC and $^1$H NMR. $^1$H NMR (200 MHz, DMSO-d6) δ 11.7 (S, 1 H), 8.38 (d, J=9.0 Hz, 1 H), 7.61 (dd, J=9.0, 2.7 Hz, 1 H), 7.49 (m, 3 H), 7.21 (m, 3 H), 5.34 (s, 2 H), 3.97 (s, 3 H), 1.98 (s, 3 H); MS-(+)-ion M+1=368.12.

e) Preparation of methyl 1-((acetoxy)methyl)-4-hydroxy-7-phenoxyisoquinoline-3-carboxylate (3c)

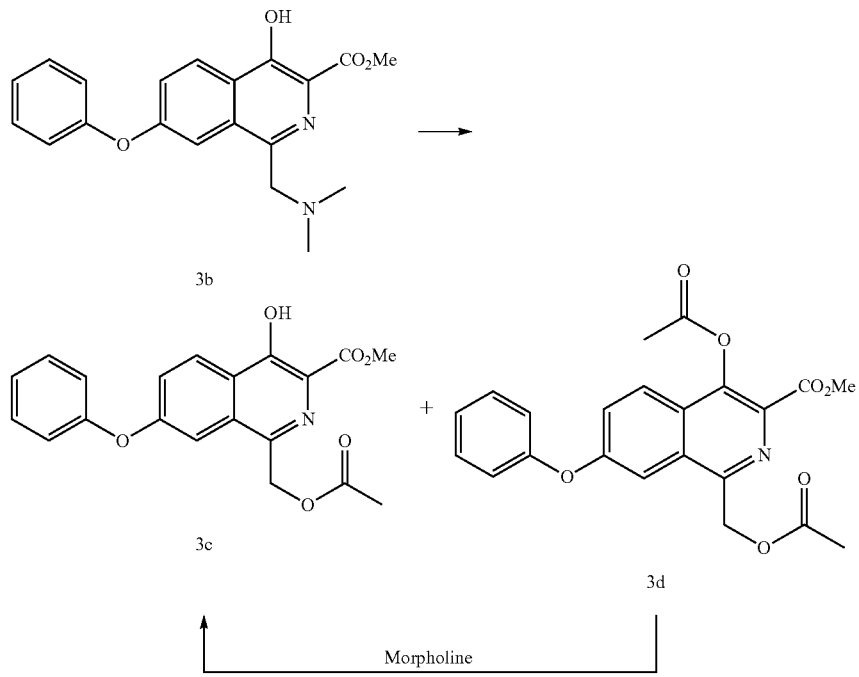

The solution of 3b from a) above was cooled below 25° C., at which time acetic anhydride (28.6 g±3.5%) was added to maintain temperature below 50° C. The resulting mixture was heated to 100±5° C. until reaction completion.

The solution of 3c and 3d from above was cooled to less than 65±5° C. Water (250 mL) was slowly added. The mixture was then cooled to below 20±5° C. and filtered. The wet cake was washed with water (3×50 mL) and added to a new flask. Dichloromethane (90 mL) and water (30 mL) were added, and the resulting mixture was stirred. The dichloromethane layer was separated and evaluated by HPLC.

The organic layer was added to a flask and cooled 5±5° C. Morpholine was added and the mixture was stirred until reaction completion. Solvent was replaced with acetone/methanol mixture. After cooling, compound 3c precipitated and was filtered, washed and dried in an oven (Yield: 81%, HPLC: >99.7%). $^1$H NMR (200 MHz, DMSO-d6) δ 11.6 (S, 1 H), 8.31 (d, J=9.0 Hz, 1 H), 7.87 (d, J=2.3 Hz, 1 H), 7.49 (m, 3 H), 7.24 (m, 3 H), 3.95 (s, 3 H), 3.68 (s, 2H), 2.08 (s, 6 H); MS-(+)-ion M+1=357.17.

f) Preparation of methyl 4-hydroxy-1-methyl-7-phenoxyisoquinoline-3-carboxylate (3e)

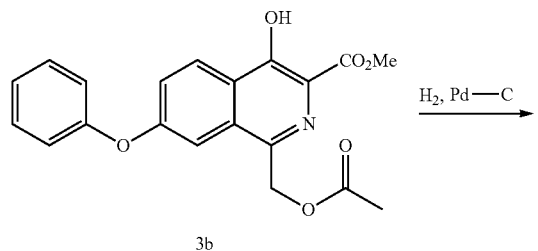

A reactor was charged with 3c (16.0 g), Pd/C (2.08 g), anhydrous $Na_2CO_3$ (2.56 g) and ethyl acetate (120 mL). The flask was vacuum-purged with nitrogen (3×) and vacuum-purged with hydrogen (3×). The flask was then pressurized with hydrogen and stirred at about 60° C. until completion of reaction. The flask was cooled to 20-25° C., the pressure released to ambient, the head space purged with nitrogen three times and mixture was filtered. The filtrate was concentrated. Methanol was added. The mixture was stirred and then cooled. Product precipitated and was filtered and dried in an oven (Yield: 90%, HPLC: 99.7%).

g) Preparation of 2-(4-hydroxy-1-methyl-7-phenoxyisoquinoline-3-carboxamido)acetic acid (3f)

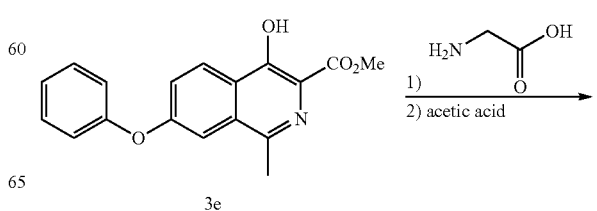

-continued

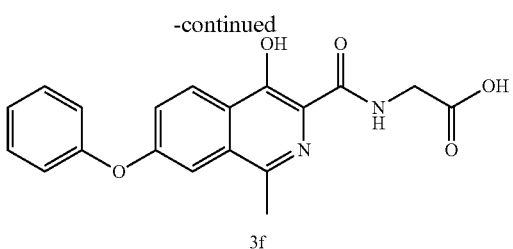

3f 2-(4-hydroxy-1-methyl-7-phenoxyisoquinoline-3-carboxamido)acetic acid was prepared from 3e according to the following procedure.

A pressure flask was charged with 3e (30.92 g), glycine (22.52 g), methanol (155 mL), sodium methoxide solution (64.81 g) and sealed (as an alternative, sodium glycinate was used in place of glycine and sodium methoxide). The reaction was heated to about 110° C. until reaction was complete. The mixture was cooled, filtered, washed with methanol, dried under vacuum, dissolved in water and washed with ethyl acetate. The ethyl acetate was removed and to the resulting aqueous layer an acetic acid (18.0 g) solution was added. The suspension was stirred at room temperature, filtered, and the solid washed with water (3×30 mL), cold acetone (5-10° C., 2×20 mL), and dried under vacuum to obtain 2-(4-hydroxy-1-methyl-7-phenoxyisoquinoline-3-carboxamido)acetic acid (Yield: 86.1%, HPLC: 99.8%).

Example 4

Preparation of 2-(4-hydroxy-1-methyl-8-phenoxyisoquinoline-3-carboxamido)acetic acid a) Preparation of methyl 1-((dimethylamino)methyl)-4-hydroxy-8-phenoxyisoquinoline-3-carboxylate (4b)

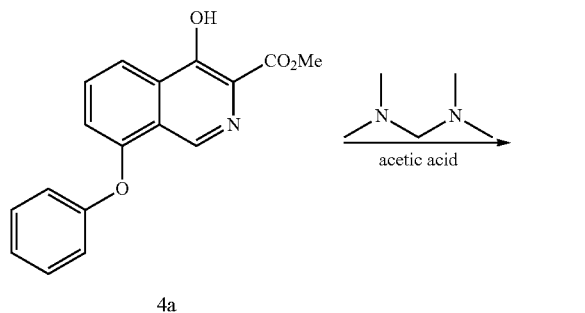

A round bottom flask fitted with thermocouple and condenser can be charged with 4a and acetic acid (about 7 molar equivalents±5%). The suspension of 4a in acetic acid can be stirred vigorously with magnetic stirring (note: overhead stirring should be done for larger scale work). A slight excess of bis-dimethylaminomethane (about 1.25 molar equivalents) can then be slowly added to the mixture [Note: Reaction is slightly exothermic, 15-20° C. temperature rise can be observed]. After the addition is complete, the mixture can be heated to 55±5° C. and maintained for at least 8 h. The reaction can then be evaluated by HPLC. If the amount of 4a is greater than 0.5%, the reaction can be stirred for additional 2 hours at 55±5° C. and reevaluated by HPLC.

b) Preparation of methyl 1-(((acetoxy)methyl)-4-hydroxy-8-phenoxyisoquinoline-3-carboxylate (4c)

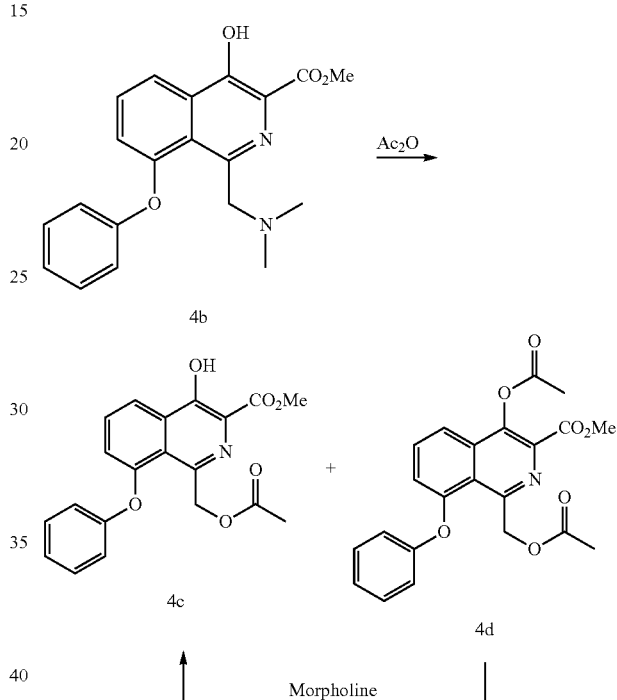

The solution of 4b from Example 4a) can be cooled to below 25° C., at which time acetic anhydride (about 3 molar equivalents) can be added slowly at a temperature below 50° C. [Note: Reaction is exothermic, 20-25° C. temperature rise can be observed. Rate of addition is important to control the exothermic reaction between acetic anhydride and dimethyl amine 4b. Excess heat generated will cause unsafe rapid evolution of gaseous dimethyl amine]. After the addition is complete, the mixture can be heated to 100±5° C. for 20-24 hours. The reaction can then be evaluated by HPLC. If 4b is in an amount greater than 2%, the reaction can be stirred for an additional 2 hours and then reevaluated by HPLC.

4d can be converted to 4c by the following procedure. The solution of 4c and 4d from the above procedure can be cooled to less than 65±5° C. with good mixing. If the reaction temperature goes below 30° C., the reaction may solidify. Water can be slowly and steadily added (the first half can be added over 1 hour and the rest added over 30 minutes). The mixture can then be cooled and stirred at 20±5° C. for at least 3 hours, at which time the mixture can be filtered and the wet cake washed with water (3×) and added to a round bottom flask fitted with a mechanical stirrer. Dichloromethane and water (3:1 by volume) can be added and the mixture stirred for 30 minutes. The dichloromethane can be separated (without including the interface or aqueous layer) and the solution evaluated by HPLC.

4c can be further purified according to the following procedure. The above solution can be added to a flask, fitted with mechanical stirrer, and cooled to 5±5° C. Morpholine can be added and the mixture stirred at 5±5° C. for 30-60 minutes and evaluated by HPLC. If the amount of 4d is greater than 2%, the reaction can be stirred for an additional hour. Once the reaction reached completion, 4c can be precipitated from cold acetone/methanol solution, filtered, washed and dried under vacuum at 50±5° C.

c) Preparation of methyl 4-hydroxy-1-methyl-8-phenoxyisoquinoline-3-carboxylate (4e)

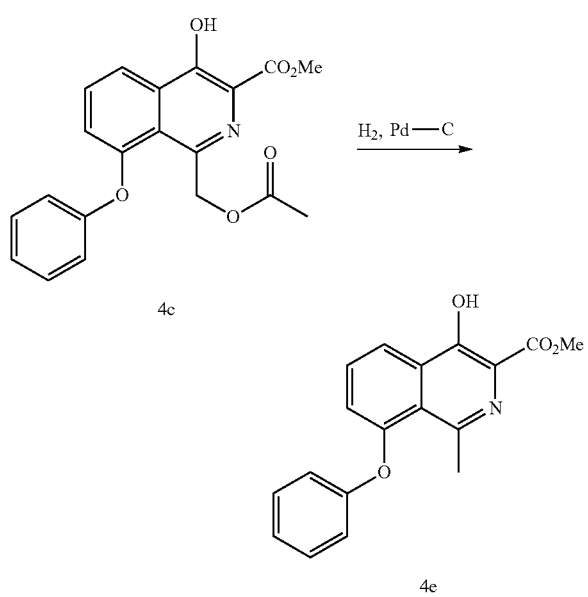

A glass lined Parr pressure reactor vessel equipped with a 4-blade impeller can be charged with 4c, Pd/C (about 0.4 to 0.5 molar equivalents), anhydrous Na₂CO₃ (about 0.5 molar equivalents), and ethyl acetate. The flask can then be vacuum-purged with nitrogen (3×) and vacuum-purged with hydrogen (3×). The flask can then be pressurized with hydrogen to set point 60 psi and stirred at 60° C. for 6-8 hrs until completion of reaction (4c <0.5%). The flask can then be cooled to 20-25° C., the pressure released to ambient, the head space purged with nitrogen three times and filtered through glass microfiber filter paper. The filtrate can be concentrated and precipitated from cold methanol and dried under vacuum at 50±5° C.

d) Preparation of 2-(4-hydroxy-1-methyl-8-phenoxyisoquinoline-3-carboxamido)acetic acid (4f)

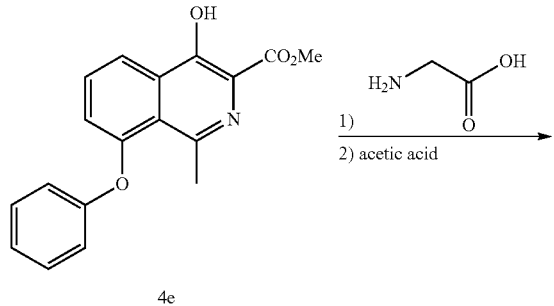

-continued

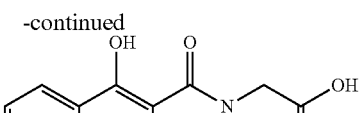

4f 2-(4-hydroxy-1-methyl-8-phenoxyisoquinoline-3-carboxamido)acetic acid is prepared from 4e according to the following procedure.

A pressure glass reaction flask which included top threads for a screw cap lid can be fitted with a magnetic stirrer, charged with 4e, glycine (about 3 molar equivalents), methanol, and a sodium methoxide solution (with 1.2 molar eqivalents NaOCH₃) and sealed. The reaction can then be heated to 110° C. for at least 6 h during which time the reaction forms a yellow suspension. The reaction can then be cooled to 20-25° C. and evaluated by HPLC. The reaction can be continued until less than 1% 4e remains as determined by HPLC, filtered, washed with methanol, dried under vacuum, dissolved in water and extracted with ethyl acetate to remove impurities to below 0.1%. The ethyl acetate can be removed and an acetic acid solution (with 3 molar eqivalents acetic acid) can be added over one hour. The suspension can be stirred at room temperature for at least 3 hours, filtered, and the solid washed with water (3×), cold acetone (5-10° C., 2×) and evaluated for impurities by HPLC. If acetone removable impurities are present, the flask can be charged with acetone and refluxed for at least 8 h, slowly cooled to 5-10° C., stirred for at least 2-3 h, filtered, washed with cold acetone (5-10° C., 3×) and dried under vacuum to obtain 2-(4-hydroxy-1-methyl-8-phenoxyisoquinoline-3-carboxamido)acetic acid.

Example 5

Preparation of 2-[4-hydroxy-1-methyl-7-(4-methoxy-phenoxy)-isoquinoline-3-carboxamido]acetic acid a) Preparation of methyl 1-((dimethylamino)methyl)-4-hydroxy-7-(4-methoxy-phenoxy)-isoquinoline-3-carboxylate (5b)

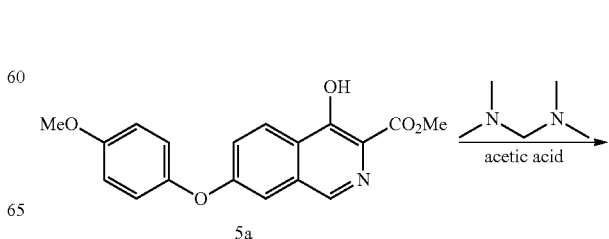

5a

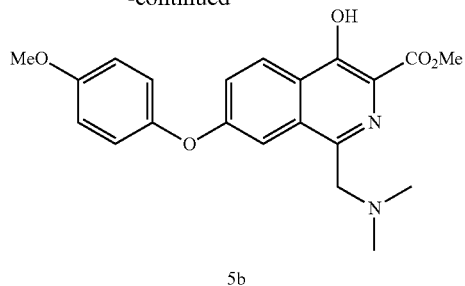

5b

A round bottom flask fitted with thermocouple and condenser can be charged with 5a and acetic acid (about 7 molar equivalents±5%). The suspension of 5a in acetic acid can be stirred vigorously with magnetic stirring (note: overhead stirring should be done for larger scale work). A slight excess of bis-dimethylaminomethane (about 1.25 molar equivalents) can then be slowly added to the mixture [Note: Reaction is slightly exothermic, 15-20° C. temperature rise can be observed]. After the addition is complete, the mixture can be heated to 55±5° C. and maintained for at least 8 h. The reaction can then be evaluated by HPLC. If the amount of 5a is greater than 0.5%, the reaction can be stirred for additional 2 hours at 55±5° C. and reevaluated by HPLC.

b) Preparation of methyl 1-((acetoxy)methyl)-4-hydroxy-7-(4-methoxy-phenoxy)-isoquinoline-3-carboxylate (5c)

The solution of 5b from Example 5a) can be cooled to below 25° C., at which time acetic anhydride (about 3 molar equivalents) can be added slowly at a temperature below 50° C. [Note: Reaction is exothermic, 20-25° C. temperature rise can be observed. Rate of addition is important to control the exothermic reaction between acetic anhydride and dimethyl amine or 5b. Excess heat generated will cause unsafe rapid evolution of gaseous dimethyl amine]. After the addition is complete, the mixture can be heated to 100±5° C. for 20-24 hours. The reaction can then be evaluated by HPLC. If 5b is in an amount greater than 2%, the reaction can be stirred for an additional 2 hours and then reevaluated by HPLC.

5d can be converted to 5c by the following procedure. The solution of 5c and 5d from the above procedure can be cooled to less than 65±5° C. with good mixing. If the reaction temperature goes below 30° C., the reaction may solidify. Water can be slowly and steadily added (the first half can be added over 1 hour and the rest added over 30 minutes). The mixture can then be cooled and stirred at 20±5° C. for at least 3 hours, at which time the mixture can be filtered and the wet cake washed with water (3×) and added to a round bottom flask fitted with a mechanical stirrer. Dichloromethane and water (3:1 by volume) can be added and the mixture stirred for 30 minutes. The dichloromethane can be separated (without including the interface or aqueous layer) and the solution evaluated by HPLC.

5c can be further purified according to the following procedure. The above solution can be added to a flask, fitted with mechanical stirrer, and cooled to 5±5° C. Morpholine can be added and the mixture stirred at 5±5° C. for 30-60 minutes and evaluated by HPLC. If the amount of 5d is greater than

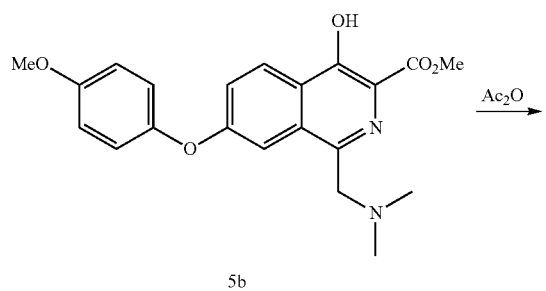

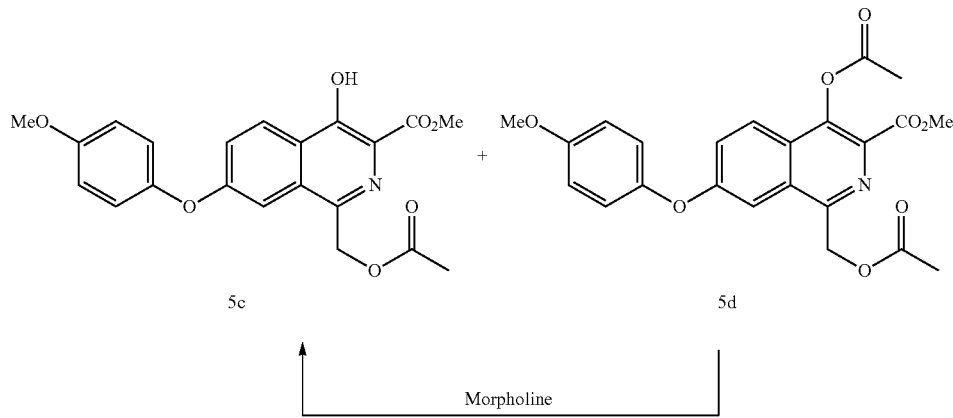

c) Preparation of methyl 4-hydroxy-1-methyl-7-(4-methoxy-phenoxy)-isoquinoline-3-carboxylate (5e)

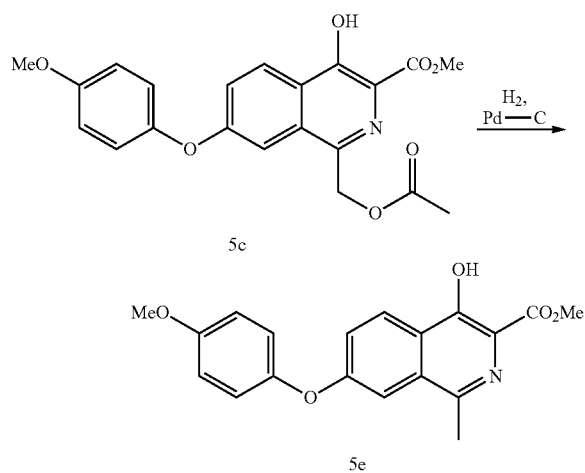

A glass lined Parr pressure reactor vessel equipped with a 4-blade impeller can be charged with 5c, Pd/C (about 0.4 to 0.5 molar equivalents), anhydrous Na₂CO₃ (about 0.5 molar equivalents), and ethyl acetate. The flask can then be vacuum-purged with nitrogen (3×) and vacuum-purged with hydrogen (3×). The flask can then be pressurized with hydrogen to set point 60 psi and stirred at 60° C. for 6-8 hrs until completion of reaction (5c <0.5%). The flask can then be cooled to 20-25° C., the pressure released to ambient, the head space purged with nitrogen three times and filtered through glass microfiber filter paper. The filtrate can be concentrated and precipitated from cold methanol and dried under vacuum at 50±5° C.

d) Preparation of 2-[4-hydroxy-1-methyl-7-(4-methoxy-phenoxy)-isoquinoline-3-carboxamido]acetic acid (5f)

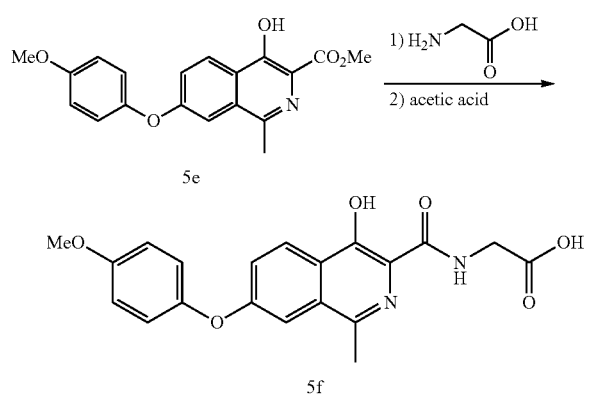

2-[4-Hydroxy-1-methyl-7-(4-methoxy-phenoxy)-isoquinoline-3-carboxamido]acetic acid is prepared from 5e according to the following procedure.

A pressure glass reaction flask which included top threads for a screw cap lid can be fitted with a magnetic stirrer, charged with 5e, glycine (about 3 molar equivalents), methanol, and a sodium methoxide solution (with 1.2 molar eqivalents NaOCH₃) and sealed. The reaction can then be heated to 110° C. for at least 6 h during which time the reaction forms a yellow suspension. The reaction can then be cooled to 20-25° C. and evaluated by HPLC. The reaction can be continued until less than 1% 5e remains as determined by HPLC, filtered, washed with methanol, dried under vacuum, dissolved in water and extracted with ethyl acetate to remove impurities to below 0.1%. The ethyl acetate can be removed and an acetic acid solution (with 3 molar eqivalents acetic acid) can be added over one hour. The suspension can be stirred at room temperature for at least 3 hours, filtered, and the solid washed with water (3×), cold acetone (5-10° C., 2×) and evaluated for impurities by HPLC. If acetone removable impurities are present, the flask can be charged with acetone and refluxed for at least 8 h, slowly cooled to 5-10° C., stirred for at least 2-3 h, filtered, washed with cold acetone (5-10° C., 3×) and dried under vacuum to obtain 2-[4-hydroxy-1-methyl-7-(4-methoxy-phenoxy)-isoquinoline-3-carboxamido] acetic acid.

Example 6

Preparation of 2-[4-hydroxy-1-methyl-6-(4-methoxy-phenoxy)-isoquinoline-3-carboxamido]acetic acid a) Preparation of methyl 1-((dimethylamino)methyl)-4-hydroxy-6-(4-methoxy-phenoxy)-isoquinoline-3-carboxylate (6b)

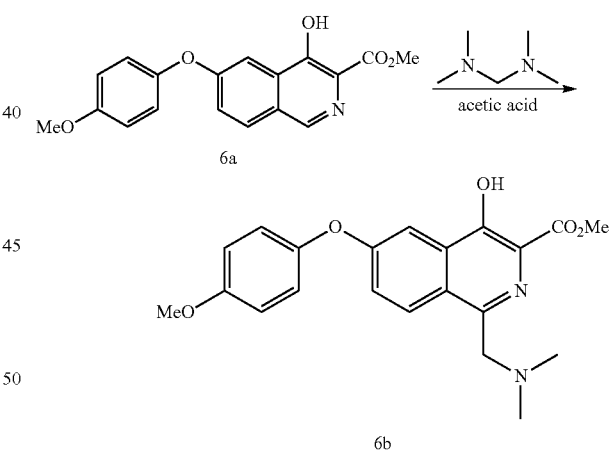

A round bottom flask fitted with thermocouple and condenser can be charged with 6a and acetic acid (about 7 molar equivalents±5%). The suspension of 6a in acetic acid can be stirred vigorously with magnetic stirring (note: overhead stirring should be done for larger scale work). A slight excess of bis-dimethylaminomethane (about 1.25 molar equivalents) can then be slowly added to the mixture [Note: Reaction is slightly exothermic, 15-20° C. temperature rise can be observed]. After the addition is complete, the mixture can be heated to 55±5° C. and maintained for at least 8 h. The reaction can then be evaluated by HPLC. If the amount of 6a is greater than 0.5%, the reaction can be stirred for additional 2 hours at 55±5° C. and reevaluated by HPLC.

b) Preparation of methyl 1-((acetoxy)methyl)-4-hydroxy-6-(4-methoxy-phenoxy)-isoquinoline-3-carboxylate (6c)

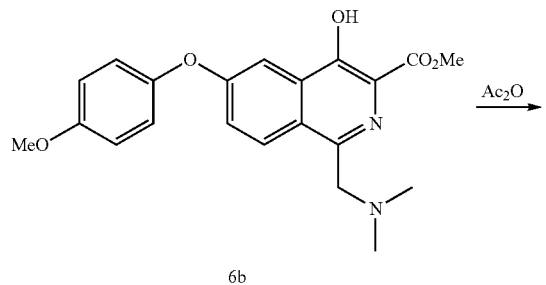

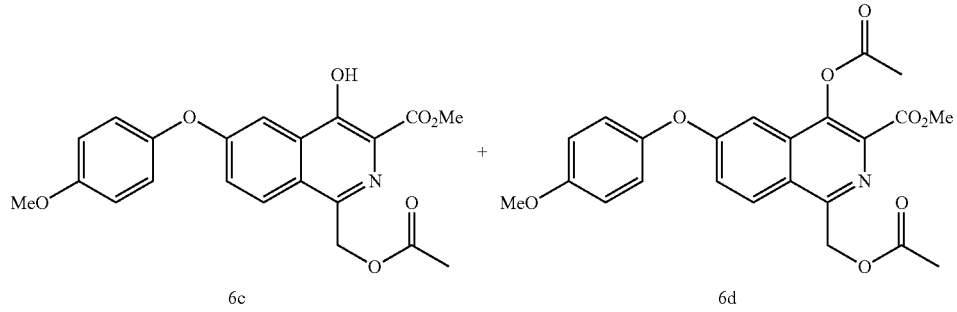

The solution of 6b from Example 6a) can be cooled to below 25° C., at which time acetic anhydride (about 3 molar equivalents) can be added slowly at a temperature below 50° C. [Note: Reaction is exothermic, 20-25° C. temperature rise can be observed. Rate of addition is important to control the exothermic reaction between acetic anhydride and dimethyl amine or 6b. Excess heat generated will cause unsafe rapid evolution of gaseous dimethyl amine]. After the addition is complete, the mixture can be heated to 100±5° C. for 20-24 hours. The reaction can then be evaluated by HPLC. If 6b is in an amount greater than 2%, the reaction can be stirred for an additional 2 hours and then reevaluated by HPLC.

6d can be converted to 6c by the following procedure. The solution of 6c and 6d from the above procedure can be cooled to less than 65±5° C. with good mixing. If the reaction temperature goes below 30° C., the reaction may solidify. Water can be slowly and steadily added (the first half can be added over 1 hour and the rest added over 30 minutes). The mixture can then be cooled and stirred at 20±5° C. for at least 3 hours, at which time the mixture can be filtered and the wet cake washed with water (3×) and added to a round bottom flask fitted with a mechanical stirrer. Dichloromethane and water (3:1 by volume) can be added and the mixture stirred for 30 minutes. The dichloromethane can be separated (without including the interface or aqueous layer) and the solution evaluated by HPLC.

6c can be further purified according to the following procedure. The above solution can be added to a flask, fitted with mechanical stirrer, and cooled to 5±5° C. Morpholine can be added and the mixture stirred at 5±5° C. for 30-60 minutes and evaluated by HPLC. If the amount of 6d is greater than 2%, the reaction can be stirred for an additional hour. Once the reaction reached completion, 6c can be precipitated from cold acetone/methanol solution, filtered, washed and dried under vacuum at 50±5° C.

c) Preparation of methyl 4-hydroxy-1-methyl-6-(4-methoxy-phenoxy)-isoquinoline-3-carboxylate (6e)

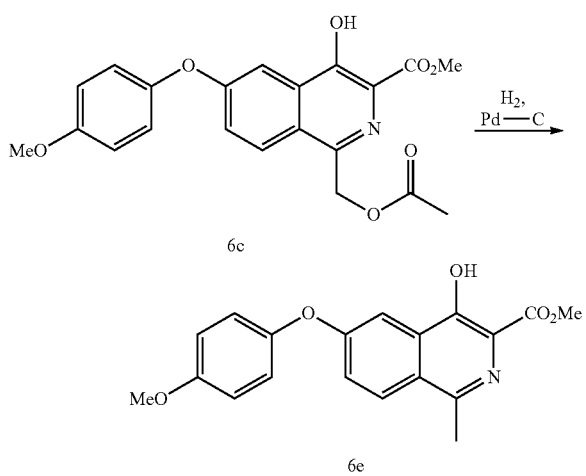

A glass lined Parr pressure reactor vessel equipped with a 4-blade impeller can be charged with 6c, Pd/C (about 0.4 to 0.5 molar equivalents), anhydrous $Na_2CO_3$ (about 0.5 molar equivalents), and ethyl acetate. The flask can then be vacuum-purged with nitrogen (3×) and vacuum-purged with hydrogen (3×). The flask can then be pressurized with hydrogen to set point 60 psi and stirred at 60° C. for 6-8 hrs until completion of reaction (6c <0.5%). The flask can then be cooled to 20-25° C., the pressure released to ambient, the head space purged with nitrogen three times and filtered through glass microfiber filter paper. The filtrate can be concentrated and precipitated from cold methanol and dried under vacuum at 50±5° C.

d) Preparation of 2-[4-hydroxy-1-methyl-6-(4-methoxy-phenoxy)-isoquinoline-3-carboxamido]acetic acid (61)

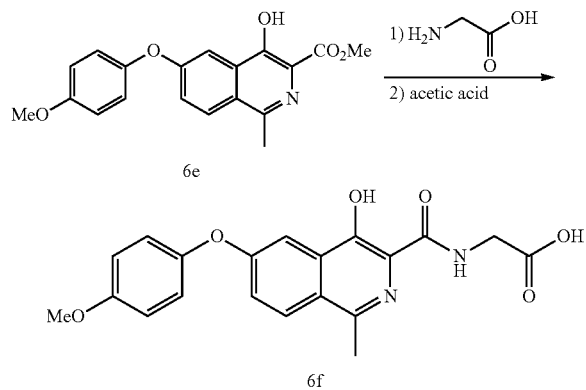

2-[4-Hydroxy-1-methyl-6-(4-methoxy-phenoxy)-isoquinoline-3-carboxamido]acetic acid is prepared from 6e according to the following procedure.

A pressure glass reaction flask which included top threads for a screw cap lid can be fitted with a magnetic stirrer, charged with 6e, glycine (about 3 molar equivalents), methanol, and a sodium methoxide solution (with 1.2 molar eqivalents NaOCH₃) and sealed. The reaction can then be heated to 110° C. for at least 6 h during which time the reaction forms a yellow suspension. The reaction can then be cooled to 20-25° C. and evaluated by HPLC. The reaction can be continued until less than 1% 6e remains as determined by HPLC, filtered, washed with methanol, dried under vacuum, dissolved in water and extracted with ethyl acetate to remove impurities to below 0.1%. The ethyl acetate can be removed and an acetic acid solution (with 3 molar eqivalents acetic acid) can be added over one hour. The suspension can be stirred at room temperature for at least 3 hours, filtered, and the solid washed with water (3×), cold acetone (5-10° C., 2×) and evaluated for impurities by HPLC. If acetone removable impurities are present, the flask can be charged with acetone and refluxed for at least 8 h, slowly cooled to 5-10° C., stirred for at least 2-3 h, filtered, washed with cold acetone (5-10° C., 3×) and dried under vacuum to obtain 2-[4-hydroxy-1-methyl-6-(4-methoxy-phenoxy)-isoquinoline-3-carboxamido] acetic acid.

Example 7

Preparation of 2-[4-hydroxy-1-methyl-7-(3,5-difluoro-phenoxy)-isoquinoline-3-carboxamido]acetic acid a) Preparation of methyl 1-((dimethylamino)methyl)-4-hydroxy-7-(3,5-difluoro-phenoxy)-isoquinoline-3-carboxylate (7b)

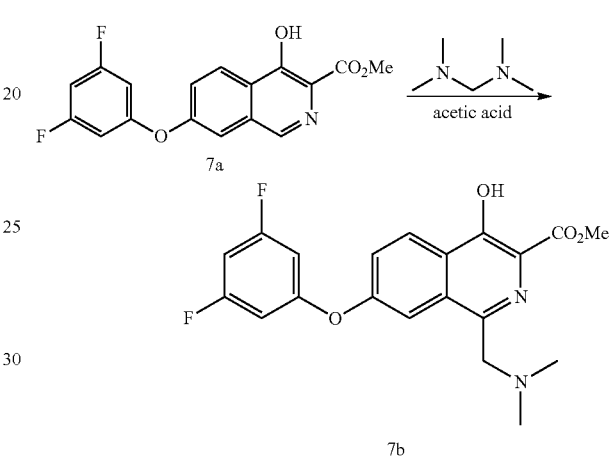

A round bottom flask fitted with thermocouple and condenser can be charged with 7a and acetic acid (about 7 molar equivalents±5%). The suspension of 7a in acetic acid can be stirred vigorously with magnetic stirring (note: overhead stirring should be done for larger scale work). A slight excess of bis-dimethylaminomethane (about 1.25 molar equivalents) can then be slowly added to the mixture [Note: Reaction is slightly exothermic, 15-20° C. temperature rise can be observed]. After the addition is complete, the mixture can be heated to 55±5° C. and maintained for at least 8 h. The reaction can then be evaluated by HPLC. If the amount of 7a is greater than 0.5%, the reaction can be stirred for additional 2 hours at 55±5° C. and reevaluated by HPLC.

b) Preparation of methyl 1-((acetoxy)methyl)-4-hydroxy-7-(3,5-difluoro-phenoxy)-isoquinoline-3-carboxylate (7c)

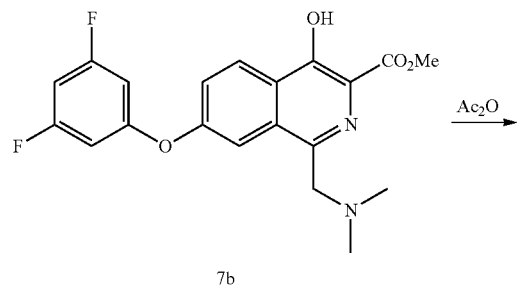

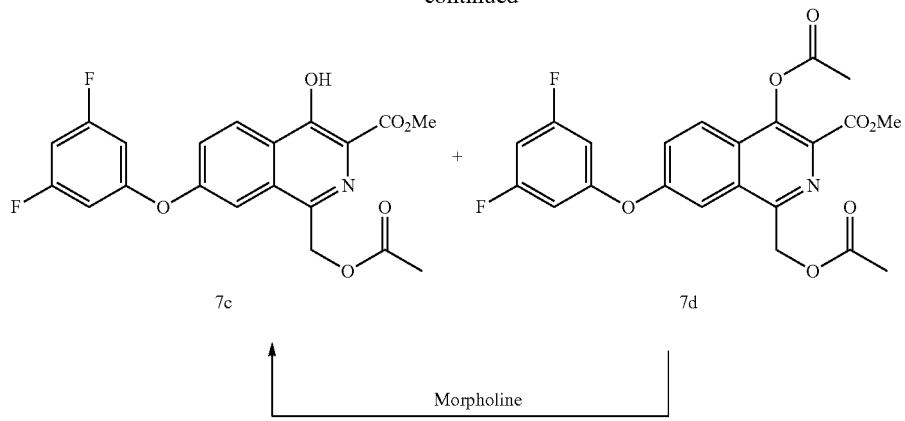

The solution of 7b from Example 7a) can be cooled to below 25° C., at which time acetic anhydride (about 3 molar equivalents) can be added slowly at a temperature below 50° C. [Note: Reaction is exothermic, 20-25° C. temperature rise can be observed. Rate of addition is important to control the exothermic reaction between acetic anhydride and dimethyl amine or 7b. Excess heat generated will cause unsafe rapid evolution of gaseous dimethyl amine]. After the addition is complete, the mixture can be heated to 100±5° C. for 20-24 hours. The reaction can then be evaluated by HPLC. If 7b is in an amount greater than 2%, the reaction can be stirred for an additional 2 hours and then reevaluated by HPLC.

7d can be converted to 7c by the following procedure. The solution of 7c and 7d from the above procedure can be cooled to less than 65±5° C. with good mixing. If the reaction temperature goes below 30° C., the reaction may solidify. Water can be slowly and steadily added (the first half can be added over 1 hour and the rest added over 30 minutes). The mixture can then be cooled and stirred at 20±5° C. for at least 3 hours, at which time the mixture can be filtered and the wet cake washed with water (3×) and added to a round bottom flask fitted with a mechanical stirrer. Dichloromethane and water (3:1 by volume) can be added and the mixture stirred for 30 minutes. The dichloromethane can be separated (without including the interface or aqueous layer) and the solution evaluated by HPLC.

7c can be further purified according to the following procedure. The above solution can be added to a flask, fitted with mechanical stirrer, and cooled to 5±5° C. Morpholine can be added and the mixture stirred at 5±5° C. for 30-60 minutes and evaluated by HPLC. If the amount of 7d is greater than 2%, the reaction can be stirred for an additional hour. Once the reaction reached completion, 7c can be precipitated from cold acetone/methanol solution, filtered, washed and dried under vacuum at 50±5° C.

c) Preparation of methyl 4-hydroxy-1-methyl-7-(3,5-difluoro-phenoxy)-isoquinoline-3-carboxylate (7e)

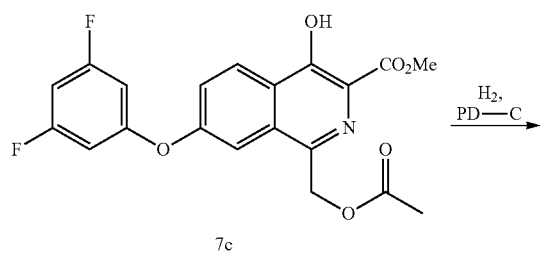

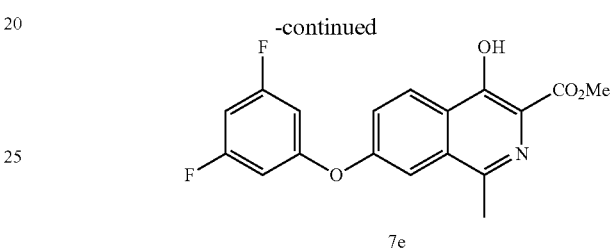

A glass lined Parr pressure reactor vessel equipped with a 4-blade impeller can be charged with 7c, Pd/C (about 0.4 to 0.5 molar equivalents), anhydrous $Na_2CO_3$ (about 0.5 molar equivalents), and ethyl acetate. The flask can then be vacuum-purged with nitrogen (3×) and vacuum-purged with hydrogen (3×). The flask can then be pressurized with hydrogen to set point 60 psi and stirred at 60° C. for 6-8 hrs until completion of reaction (7c <0.5%). The flask can then be cooled to 20-25° C., the pressure released to ambient, the head space purged with nitrogen three times and filtered through glass microfiber filter paper. The filtrate can be concentrated and precipitated from cold methanol and dried under vacuum at 50±5° C.

d) Preparation of 2-[4-hydroxy-1-methyl-7-(3,5-difluoro-phenoxy)-isoquinoline-3-carboxamido]acetic acid (7f)

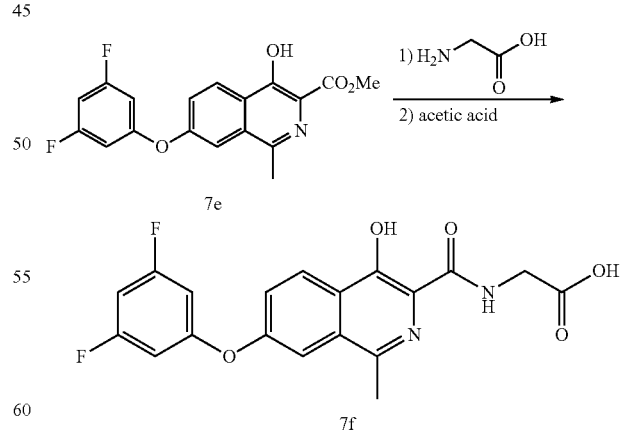

2-[4-Hydroxy-1-methyl-7-(3,5-difluoro-phenoxy)-isoquinoline-3-carboxamido]acetic acid is prepared from 7e according to the following procedure.

A pressure glass reaction flask which included top threads for a screw cap lid can be fitted with a magnetic stirrer, charged with 7e, glycine (about 3 molar equivalents), methanol, and a sodium methoxide solution (with 1.2 molar eqivalents NaOCH₃) and sealed. The reaction can then be heated to 110° C. for at least 6 h during which time the reaction forms a yellow suspension. The reaction can then be cooled to 20-25° C. and evaluated by HPLC. The reaction can be continued until less than 1% 7e remains as determined by HPLC, filtered, washed with methanol, dried under vacuum, dissolved in water and extracted with ethyl acetate to remove impurities to below 0.1%. The ethyl acetate can be removed and an acetic acid solution (with 3 molar eqivalents acetic acid) can be added over one hour. The suspension can be stirred at room temperature for at least 3 hours, filtered, and the solid washed with water (3×), cold acetone (5-10° C., 2×) and evaluated for impurities by HPLC. If acetone removable impurities are present, the flask can be charged with acetone and refluxed for at least 8 h, slowly cooled to 5-10° C., stirred for at least 2-3 h, filtered, washed with cold acetone (5-10° C., 3×) and dried under vacuum to obtain 2-[4-hydroxy-1-methyl-7-(3,5-difluoro-phenoxy)-isoquinoline-3-carboxamido] acetic acid.

Example 8

Preparation of 2-[4-hydroxy-1-methyl-6-(3,5-difluoro-phenoxy)-isoquinoline-3-carboxamido]acetic acid a) Preparation of methyl 1-((dimethylamino)methyl)-4-hydroxy-6-(3,5-difluoro-phenoxy)-isoquinoline-3-carboxylate (8b)

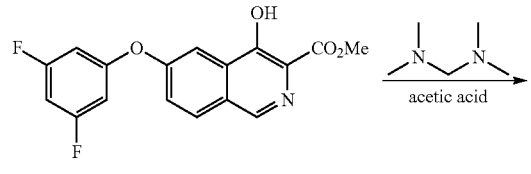

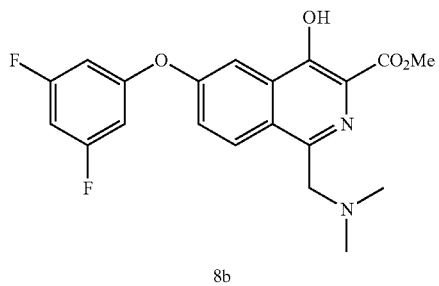

A round bottom flask fitted with thermocouple and condenser can be charged with 8a and acetic acid (about 7 molar equivalents±5%). The suspension of 8a in acetic acid can be stirred vigorously with magnetic stirring (note: overhead stirring should be done for larger scale work). A slight excess of bis-dimethylaminomethane (about 1.25 molar equivalents) can then be slowly added to the mixture [Note: Reaction is slightly exothermic, 15-20° C. temperature rise can be observed]. After the addition is complete, the mixture can be heated to 55±5° C. and maintained for at least 8 h. The reaction can then be evaluated by HPLC. If the amount of 8a is greater than 0.5%, the reaction can be stirred for additional 2 hours at 55±5° C. and reevaluated by HPLC.

b) Preparation of methyl 1-((acetoxy)methyl)-4-hydroxy-6-(3,5-difluoro-phenoxy)-isoquinoline-3-carboxylate (8c)

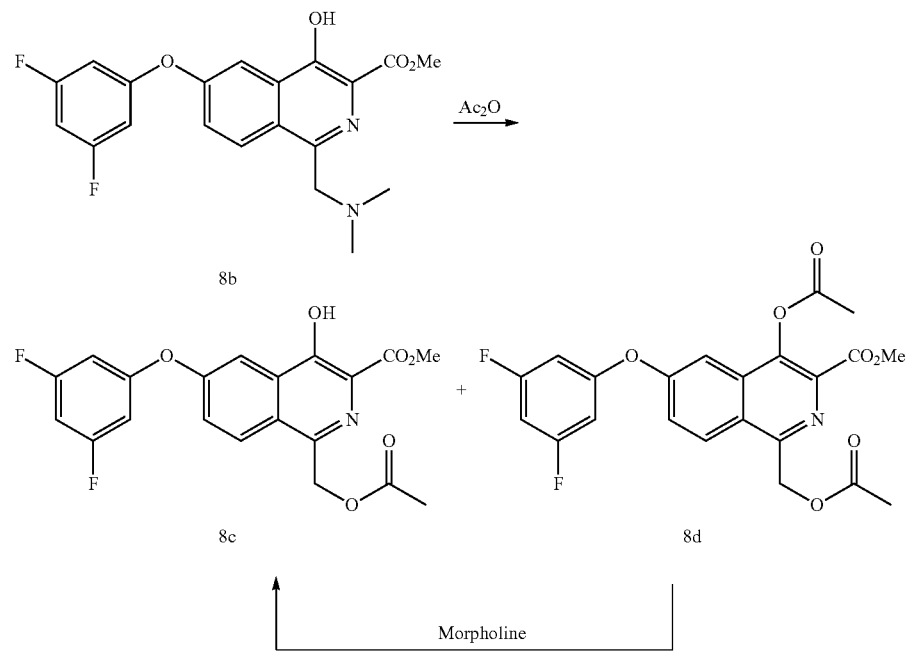

The solution of 8b from Example 8a) can be cooled to below 25° C., at which time acetic anhydride (about 3 molar equivalents) can be added slowly at a temperature below 50° C. [Note: Reaction is exothermic, 20-25° C. temperature rise can be observed. Rate of addition is important to control the exothermic reaction between acetic anhydride and dimethyl amine or 8b. Excess heat generated will cause unsafe rapid evolution of gaseous dimethyl amine]. After the addition is complete, the mixture can be heated to 100±5° C. for 20-24 hours. The reaction can then be evaluated by HPLC. If 8b is in an amount greater than 2%, the reaction can be stirred for an additional 2 hours and then reevaluated by HPLC.

8d can be converted to 8c by the following procedure. The solution of 8c and 8d from the above procedure can be cooled to less than 65±5° C. with good mixing. If the reaction temperature goes below 30° C., the reaction may solidify. Water can be slowly and steadily added (the first half can be added over 1 hour and the rest added over 30 minutes). The mixture can then be cooled and stirred at 20±5° C. for at least 3 hours, at which time the mixture can be filtered and the wet cake washed with water (3×) and added to a round bottom flask fitted with a mechanical stirrer. Dichloromethane and water (3:1 by volume) can be added and the mixture stirred for 30 minutes. The dichloromethane can be separated (without including the interface or aqueous layer) and the solution evaluated by HPLC.

8c can be further purified according to the following procedure. The above solution can be added to a flask, fitted with mechanical stirrer, and cooled to 5±5° C. Morpholine can be added and the mixture stirred at 5±5° C. for 30-60 minutes and evaluated by HPLC. If the amount of 8d is greater than 2%, the reaction can be stirred for an additional hour. Once the reaction reached completion, 8c can be precipitated from cold acetone/methanol solution, filtered, washed and dried under vacuum at 50±5° C.

c) Preparation of methyl 4-hydroxy-1-methyl-6-(3,5-difluoro-phenoxy)-isoquinoline-3-carboxylate (8e)

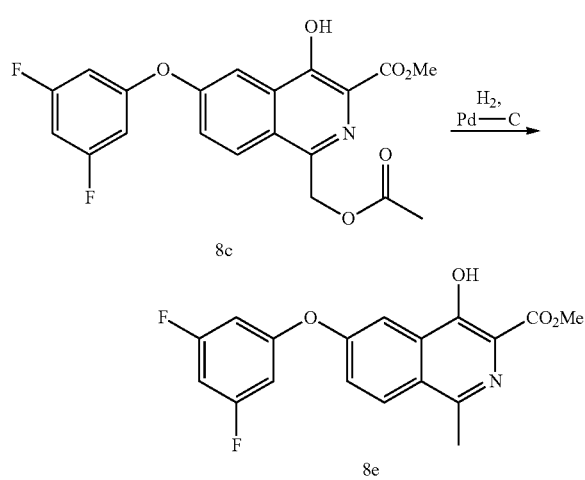

A glass lined Parr pressure reactor vessel equipped with a 4-blade impeller can be charged with 8c, Pd/C (about 0.4 to 0.5 molar equivalents), anhydrous $Na_2CO_3$ (about 0.5 molar equivalents), and ethyl acetate. The flask can then be vacuum-purged with nitrogen (3×) and vacuum-purged with hydrogen (3×). The flask can then be pressurized with hydrogen to set point 60 psi and stirred at 60° C. for 6-8 hrs until completion of reaction (8c <0.5%). The flask can then be cooled to 20-25° C., the pressure released to ambient, the head space purged with nitrogen three times and filtered through glass microfiber filter paper. The filtrate can be concentrated and precipitated from cold methanol and dried under vacuum at 50±5° C.

d) Preparation of 2-[4-hydroxy-1-methyl-6-(3,5-difluoro-phenoxy)-isoquinoline-3-carboxamido]acetic acid (8f)

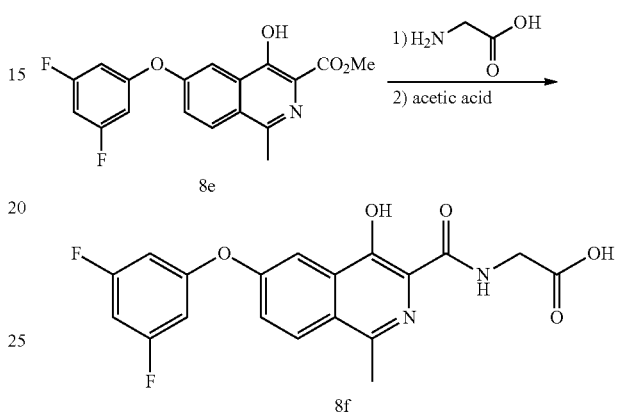

2-[4-hydroxy-1-methyl-6-(3,5-difluoro-phenoxy)-isoquinoline-3-carboxamido]acetic acid is prepared from 8e according to the following procedure.

A pressure glass reaction flask which included top threads for a screw cap lid can be fitted with a magnetic stirrer, charged with 8e, glycine (about 3 molar equivalents), methanol, and a sodium methoxide solution (with 1.2 molar eqivalents $NaOCH_3$) and sealed. The reaction can then be heated to 110° C. for at least 6 h during which time the reaction forms a yellow suspension. The reaction can then be cooled to 20-25° C. and evaluated by HPLC. The reaction can be continued until less than 1% 8e remains as determined by HPLC, filtered, washed with methanol, dried under vacuum, dissolved in water and extracted with ethyl acetate to remove impurities to below 0.1%. The ethyl acetate can be removed and an acetic acid solution (with 3 molar eqivalents acetic acid) can be added over one hour. The suspension can be stirred at room temperature for at least 3 hours, filtered, and the solid washed with water (3×), cold acetone (5-10° C., 2×) and evaluated for impurities by HPLC. If acetone removable impurities are present, the flask can be charged with acetone and refluxed for at least 8 h, slowly cooled to 5-10° C., stirred for at least 2-3 h, filtered, washed with cold acetone (5-10° C., 3×) and dried under vacuum to obtain 2-[4-hydroxy-1-methyl-6-(3,5-difluoro-phenoxy)-isoquinoline-3-carboxamido] acetic acid.

Example 9

Biological Testing

The compounds and methods of the invention can be used for the synthesis of various isoquinoline compounds. Such compounds are known to be useful for inhibiting HIF hydroxylase activity, thereby increasing the stability and/or activity of hypoxia inducible factor (HIF), and can be used to treat and prevent HIF-associated conditions and disorders (see, e.g., U.S. Pat. No. 7,323,475, U.S. Publication No. 2007/

0004627, U.S. Publication No. 2006/0276477, and U.S. Publication No. 2007/0259960, incorporated by reference herein).

The biological activity of exemplary substituted isoquinoline compounds may be assessed using any conventionally known methods. In particular embodiments, cells derived from animal tissues, preferably human tissues, capable of expressing erythropoietin when stimulated by compounds of the invention are cultured for the in vitro production of endogenous proteins. Cells contemplated for use in such methods include, but are not limited to, cells derived from hepatic, hematopoietic, renal, and neural tissues.

Cell culture techniques are generally available in the art and include any method that maintains cell viability and facilitates expression of endogenous proteins. Cells are typically cultured in a growth medium optimized for cell growth, viability, and protein production. Cells may be in suspension or attached to a substrate, and medium may be supplied in batch feed or continuous flow-through regimens. Compounds of the invention are added to the culture medium at levels that stimulate erythropoietin production without compromising cell viability. Erythropoietin produced by the cells is secreted into the culture medium. The medium is then collected and the erythopoietin is purified using methods known to those of skill in the art. (See, e.g., Lai et al. (1987) U.S. Pat. No. 4,667,016; and Egrie (1985) U.S. Pat. No. 4,558,006.)

Suitable assay methods are well known in the art. The following are presented only as examples and are not intended to be limiting.

Cell-Based HIFα Stabilization Assay

Human cells (e.g., Hep3B cells from hepatocellular tissue) derived from various tissues were separately seeded into 35 mm culture dishes, and grown at 37° C., 20% $O_2$, 5% $CO_2$ in standard culture medium, e.g., DMEM (Dulbecco's modification of Eagle's medium), 10% FBS (fetal bovine serum). When cell layers reach confluence, the media was replaced with OPTI-MEM media (Invitrogen Life Technologies, Carlsbad Calif.), and cell layers were incubated for approximately 24 hours in 20% $O_2$, 5% $CO_2$ at 37° C. Compound or 0.013% DMSO (dimethyl sulfoxide) was then added to existing medium and incubation was continued overnight.

Following incubation, the media was removed, centrifuged, and stored for analysis (see Cell-based VEGF and EPO assays below). The cells were washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates were centrifuged at 3,000×g for 5 minutes at 4° C., and the cytosolic fractions (supernatant) were collected. The nuclei (pellet) were resuspended and lysed in 100 µL, of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) were collected.

The Nuclear protein fractions collected were analyzed for HIF-1α using a QUANTIKINE immunoassay (R&D Systems, Inc., Minneapolis Minn.) according to the manufacturer's instructions.

Cell-Based EPO Assay

Hep3B cells (human hepatocellular carcinoma cells from ATCC, cat # HB-8064) were plated at 25,000 cells per well 96 well plates. The next day, the cells were washed once with DMEM (Cellgro, cat #10-013-CM)+0.5% fetal bovine serum (Cellgro, cat #35-010-CV) and incubated with various concentrations of compound or vehicle control (0.15% DMSO) in DMEM+0.5% fetal bovine serum for 72 hours. Cell free culture supernatants were generated by transfer to a conical bottom 96 well plate and centrifugation for 5 minutes at 2000 rpm. The supernatant was quantitated for EPO using a human EPO ELISA kit (R&D Systems, cat # DEP 00).

The EPO values for the compounds reported herein (e.g., Table 1) are the measured value for cells plus compound minus the value for the vehicle control for the same cell preparation. The EPO values for the vehicle control for the cell preparations used in experiments reported herein varied from 0-12.5 mIU/ml.

HIF-PH Assay

Ketoglutaric acid α-[1-$^{14}$C]-sodium salt, alpha-ketoglutaric acid sodium salt, and HPLC purified peptide were obtained from commercial sources, e.g., Perkin-Elmer (Wellesley Mass.), Sigma-Aldrich, and SynPep Corp. (Dublin Calif.), respectively. Peptides for use in the assay were fragments of HIFα as described above or as disclosed in International Publication WO 2005/118836, incorporated by reference herein. For example, a HIF peptide for use in the HIF-PH assay was [methoxycoumarin]-DLDLEALAPYI-PADDDFQL-amide. HIF-PH, e.g., HIF-PH2 (also known as EGLN1 or PHD2), was expressed in, e.g., insect Hi5 cells, and partially purified, e.g., through a SP ion exchange chromatography column. Enzyme activity was determined by capturing $^{14}CO_2$ using an assay described by Kivirikko and Myllyla (1982, *Methods Enzymol.* 82:245-304). Assay reactions contained 50 mM HEPES (pH 7.4), 100 µM α-ketoglutaric acid sodium salt, 0.30 µCi/mL α-ketoglutaric acid α-[1-$^{14}$C]-sodium salt, 40 µM $FeSO_4$, 1 mM ascorbate, 1541.8 units/mL Catalase, with or without 50 µM peptide substrate and various concentrations of compound of the invention. Reactions were initiated by addition of HIF-PH enzyme.

The peptide-dependent percent turnover was calculated by subtracting percent turnover in the absence of peptide from percent turnover in the presence of substrate peptide. Percent inhibition and $IC_{50}$ were calculated using peptide-dependent percent turnover at given inhibitor concentrations. Calculation of $IC_{50}$ values for each inhibitor was conducted using GraFit software (Erithacus Software Ltd., Surrey UK). The results were summarized in Table 1.

Table 1 below was intended to demonstrate the pharmacological utility of exemplary substituted isoquinoline compounds. By inhibiting HIF prolyl hydroxylase enzymes, substituted isoquinoline compounds stabilize HIFα, which then combines with HIFβ to form an active transcription factor that increases expression of numerous genes involved in response to hypoxic and ischemic conditions, including erythropoietin (EPO).

TABLE 1

| Example No. | Compound No. | $IC_{50}$ PHD2 (µM) | Cell EPO* (mIU/ml) |
| --- | --- | --- | --- |
| 1 | 1f | 7.9 | 98.6 |
| 2 | 2f | 3.5 | 78 |
| 3 | 3f | 2.1 | 182 |
| 4 | 4f | 1.4 | 52 |
| 5 | 5f | 2.2 | 209 |
| 6 | 6f | 5.2 | 191 |
| 7 | 7f | 2.2 | 225 |
| 8 | 8f | not determined | 105 |

*Cell EPO measured at 30 µM compound in DMSO compared to DMSO only control

What is claimed is:

1. A method of making a compound of formula IV or a stereoisomer or mixture of stereoisomers thereof:

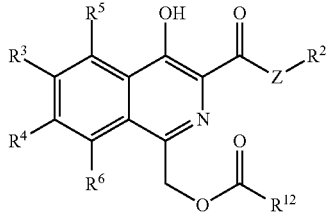

comprising contacting a compound of formula I:

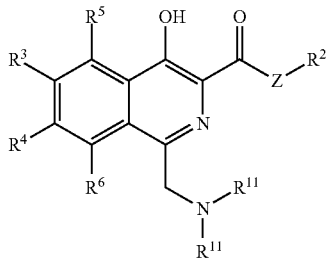

with a compound of formula

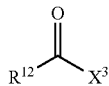

followed by a compound of formula

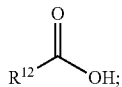

a compound of formula $R^{12}$—$X^3$ followed by a compound of formula

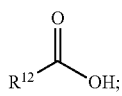

or a compound of formula V:

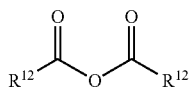

under reaction conditions sufficient to produce a compound of formula IV; wherein
Z is O, $NR^1$ or S;
$R^1$ is selected from the group consisting of hydrogen and alkyl;
$R^2$ is selected from the group consisting of hydrogen and alkyl which is unsubstituted or substituted with one or more substituents independently selected from the group consisting of cycloalkyl, heterocyclyl, aryl, and heteroaryl;
$R^3$ and $R^4$ are independently selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, —S(O)$_n$—N($R^8$)—$R^8$ where n is 0, 1, or 2, —$NR^8C(O)NR^8R^8$, —$X^1R^8$ where $X^1$ is oxygen, —S(O)$_n$— or —$NR^9$— where n is 0, 1, or 2, or $R^3$, $R^4$ together with the carbon atom pendent thereto, form a cycloalkyl, substituted cycloalkyl, heterocyclyl, substituted heterocyclyl, aryl, substituted aryl, heteroaryl, or substituted heteroaryl;
$R^5$ and $R^6$ are independently selected from the group consisting of hydrogen, halo, alkyl, substituted alkyl, alkoxy, substituted alkoxy, aryl, substituted aryl, heteroaryl, substituted heteroaryl and —$X^2R^{10}$ where $X^2$ is oxygen, —S(O)$_n$— or —$NR^{13}$— where n is 0, 1, or 2, or when $X^2$ is —$NR^{13}$—, then $R^{13}$ and $R^{10}$, together with the nitrogen atom to which they are bound, can be joined to form a heterocyclyl or substituted heterocyclyl group;
each $R^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when $X^1$ is —SO— or —SO$_2$—, then $R^8$ is not hydrogen;
$R^9$ and $R^{13}$ are independently selected from the group consisting of hydrogen, alkyl, and aryl;
$R^{10}$ is selected from the group consisting of alkyl, substituted alkyl, aryl, substituted aryl, heteroaryl, substituted heteroaryl, heterocyclyl and substituted heterocyclyl;
each $R^{11}$ is independently selected from alkyl, benzyl or aryl, or two $R^{11}$ together with the nitrogen atom to which they are attached form a 4-8 membered heterocyclyl or a heteroaryl;
each $R^{12}$ is independently selected from the group consisting of alkyl, aryl, heteroaryl, and heterocyclyl, or when two $R^{12}$ are present, two $R^{12}$ together with the carbon atom to which they are attached form a 4-8 membered heterocyclyl; and
$X^3$ is halo.

2. The method of claim 1, wherein Z is O.

3. The method of claim 1, wherein the reaction conditions sufficient to produce a compound of formula IV comprise a compound of formula V.

4. The method of claim 1, wherein the reaction conditions sufficent to produce a compound of formula IV comprise an inert atmosphere.

5. The method of claim 1, wherein the reaction conditions sufficient to produce a compound of formula IV comprise a nitrogen atmosphere.

6. The method of claim 1, wherein the reaction conditions sufficient to produce a compound of formula IV are anhydrous reaction conditions.

7. The method of claim 1, wherein the reaction conditions sufficient to produce a compound of formula IV comprise at a temperature greater than about 30° C.

8. The method of claim 1, wherein the reaction conditions sufficient to produce a compound of formula IV comprise at a temperature of about 100° C.

9. The method of claim 1, wherein $R^{11}$ and $R^{12}$ are $C_1$ to $C_4$ alkyl.

10. The method of claim 1, wherein $R^{11}$ and $R^{12}$ are methyl.

11. The method of claim 1, wherein the reaction conditions sufficient to produce a compound of formula IV comprise a compound of formula V where $R^{12}$ is $C_1$ to $C_4$ alkyl; and wherein the reaction is conducted at a temperature of about 100° C.

12. The method of claim 11, further wherein the reaction conditions sufficient to produce a compound of formula IV comprise under a nitrogen atmosphere.

13. The method of claim 1, wherein the reaction conditions sufficient to produce a compound of formula IV further comprise converting a compound of formula VII to a compound of formula IV;

VII

IV

14. The method of claim 13, wherein the reaction conditions sufficient to produce a compound of formula IV comprise an amine.

15. The method of claim 14, wherein the amine is morpholine.

16. The method of claim 13, wherein the reaction conditions sufficient to produce a compound of formula IV comprise dichloromethane.

17. The method of claim 13, wherein the reaction conditions sufficient to produce a compound of formula IV comprise a temperature below 25° C.

18. The method of claim 13, wherein the reaction conditions sufficient to produce a compound of formula IV comprise a temperature of from about 0° C. to about 10° C.

19. The method of claim 13, wherein the reaction conditions sufficient to produce a compound of formula IV comprise morpholine; and
wherein the reaction is conducted in dichloromethane and at a temperature of from about 0° C. to about 10° C.

20. The method of claim 1, wherein the method further comprises making a compound of formula VI or a stereoisomer or mixture of stereoisomers thereof:

VI comprising converting the compound of formula IV:

IV under reaction conditions sufficient to produce a compound of formula VI; wherein
Z is O, $NR^1$ or S;
$R^1$ is selected from the group consisting of hydrogen and alkyl;
$R^2$ is selected from the group consisting of hydrogen and alkyl which is unsubstituted or substituted with one or more substituents independently selected from the group consisting of cycloalkyl, heterocyclyl, aryl, and heteroaryl;
$R^3$ and $R^4$ are independently selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, $-S(O)_n-N(R^8)-R^8$ where n is 0, 1, or 2, $-NR^8C(O)NR^8R^8$, $-X^1R^8$ where $X^1$ is oxygen, $-S(O)_n-$ or $-NR^9-$ where n is 0, 1, or 2, or $R^3$, $R^4$ together with the carbon atom pendent thereto, form a cycloalkyl, substituted cycloalkyl, heterocyclyl, substituted heterocyclyl, aryl, substituted aryl, heteroaryl, or substituted heteroaryl;
$R^5$ and $R^6$ are independently selected from the group consisting of hydrogen, halo, alkyl, substituted alkyl, alkoxy, substituted alkoxy, aryl, substituted aryl, heteroaryl, substituted heteroaryl and $-X^2R^{10}$ where $X^2$ is oxygen, $-S(O)-$ or $-NR^{13}-$ where n is 0, 1, or 2, or when $X^2$ is $-NR^{13}-$, then $R^{13}$ and $R^{10}$, together with the nitrogen atom to which they are bound, can be joined to form a heterocyclyl or substituted heterocyclyl group;
each $R^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when $X^1$ is $-SO-$ or $-SO_2-$, then $R^8$ is not hydrogen;
$R^9$ and $R^{13}$ are independently selected from the group consisting of hydrogen, alkyl, and aryl; and
$R^{10}$ is selected from the group consisting of alkyl, substituted alkyl, aryl, substituted aryl, heteroaryl, substituted heteroaryl, heterocyclyl and substituted heterocyclyl; and
each $R^{12}$ is independently selected from the group consisting of alkyl, aryl, heteroaryl, and heterocyclyl.

21. The method of claim 20, wherein Z is O.

22. The method of claim 20, wherein the reaction conditions sufficient to produce a compound of formula VI comprise hydrogen.

23. The method of claim 20, wherein the reaction conditions sufficient to produce a compound of formula VI comprise a base.

24. The method claim of 23, wherein the base is sodium carbonate.

25. The method of claim 20, wherein the reaction conditions sufficient to produce a compound of formula VI comprise ethyl acetate.

26. The method of claim 20, wherein the reaction conditions sufficient to produce a compound of formula VI comprise a catalyst.

27. The method of claim 26, wherein the catalyst is Pd/C.

28. The method of claim 20, wherein the reaction conditions sufficient to produce a compound of formula VI comprise a condition under pressure.

29. The method of claim 20, wherein the reaction conditions sufficient to produce a compound of formula VI comprise a condition under pressure at about 60 psi.

30. The method of claim 20, wherein the reaction conditions sufficient to produce a compound of formula VI comprise hydrogen, sodium carbonate, ethyl acetate, Pd/C, and a condition under pressure.

31. The method of claim 20, wherein the reaction conditions sufficient to produce a compound of formula VI comprise hydrogen, sodium carbonate, ethyl acetate, Pd/C, and a condition under pressure at about 60 psi.

32. The method of claim 20, wherein $R^{12}$ is $C_1$ to $C_4$ alkyl.

33. The method of claim 20, wherein $R^{12}$ is methyl.

34. The method of claim 1, wherein the a compound of formula I or a stereoisomer or mixture of stereoisomers thereof:

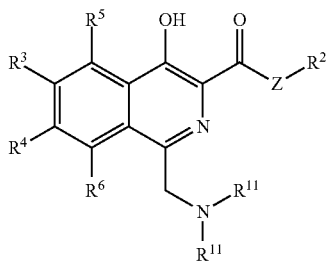

I is prepared by a method comprising contacting a compound of formula II:

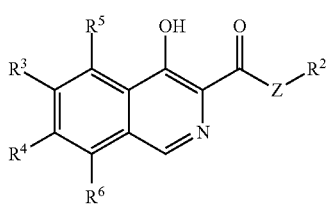

II with a compound of formula III:

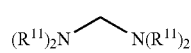

III under reaction conditions sufficient to produce a compound of formula I; wherein Z is O, $NR^1$, or S;

$R^1$ is selected from the group consisting of hydrogen and alkyl;

$R^2$ is selected from the group consisting of hydrogen and alkyl which is unsubstituted or substituted with one or more substituents independently selected from the group consisting of cycloalkyl, heterocyclyl, aryl, and heteroaryl;

$R^3$ and $R^4$ are independently selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, $-S(O)_{n-N(R^8)}-R^8$, $-NR^8C(O)NR^8R^8$, and $-X^1R^8$;

where X' is oxygen, $-S(O)_n-$, or $-NR^9-$;

n is 0, 1, or 2;

each $R^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when $X^1$ is $-SO-$ or $-SO_2-$, then $R^8$ is not hydrogen; and $R^9$ is selected from the group consisting of hydrogen, alkyl, and aryl;

or $R^3$ and $R^4$ together with the carbon atoms pendent thereto, form a cycloalkyl, substituted cycloalkyl, heterocyclyl, substituted heterocyclyl, aryl, substituted aryl, heteroaryl, or substituted heteroaryl;

$R^5$ and $R^6$ are independently selected from the group consisting of hydrogen, halo, alkyl, substituted alkyl, alkoxy, substituted alkoxy, aryl, substituted aryl, heteroaryl, substituted heteroaryl and $-X_2R_{10}$;

where $X^2$ is oxygen, $-S(O)_n-$, or $-NR^{13}-$;

n is 0, 1, or 2;

$R^{10}$ is selected from the group consisting of alkyl, substituted alkyl, aryl, substituted aryl, heteroaryl, substituted heteroaryl, heterocyclyl and substituted heterocyclyl; and $R^{13}$ is selected from the group consisting of hydrogen, alkyl, and aryl;

or when $X^2$ is $-NR^{13}-$, then $R^{10}$ and $R^{13}$, together with the nitrogen atom to which they are bound, can be joined to form a heterocyclyl or substituted heterocyclyl group; and each $R^{11}$ is independently selected from alkyl, benzyl or aryl, or two $R^{11}$ together with the nitrogen atom to which they are attached form a 4-8 membered heterocyclyl or a heteroaryl.

35. The method of claim 34, wherein Z is O.

36. The method of claim 34, wherein the reaction conditions sufficient to produce a compound of formula I comprise an acid.

37. The method of claim 36, wherein the acid is glacial acetic acid.

38. The method of claim 34 wherein the reaction conditions sufficient to produce a compound of formula I comprise a temperature greater than about 30 ° C.

39. The method of claim 34, wherein the reaction conditions sufficient to produce a compound of formula I comprise a temperature of from about 50 ° C. to about 60 ° C.

40. The method of claim 34, wherein $R^{11}$ is $C_1$ to $C_4$ alkyl.

41. A method of making a compound of formula VI or a stereoisomer or mixture of stereoisomers thereof:

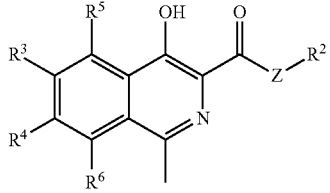

the method comprising the steps of:
a) contacting a compound of formula II with a compound of formula III

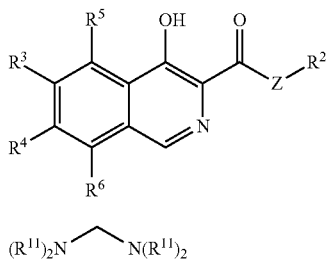

under reaction conditions sufficient to produce a compound of formula I:

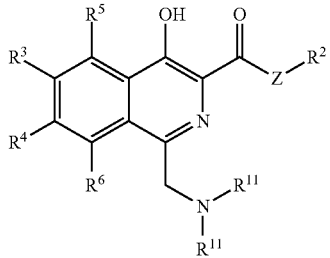

b) contacting a compound of formula I with a compound of formula

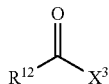

followed by a compound of formula

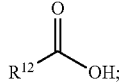

a compound of formula $R^{12}$—$X^3$ followed by a compound of formula

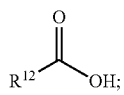

or a compound of formula V:

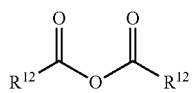

under reaction conditions sufficient to produce a compound of formula IV:

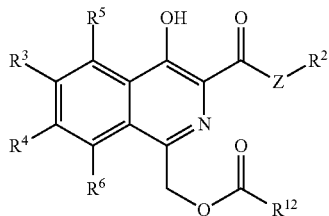

c) optionally converting a compound of formula VII:

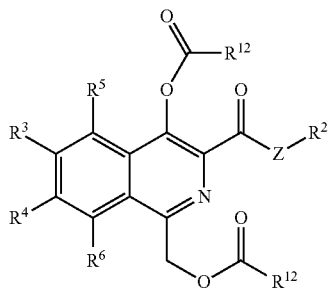

under reaction conditions sufficient to produce a compound of formula IV; and d) converting a compound of formula IV under reaction conditions sufficient to produce a compound of formula VI;
wherein
Z is O, $NR^1$ or S;
$R^1$ is selected from the group consisting of hydrogen and alkyl;
$R^2$ is selected from the group consisting of hydrogen and alkyl which is unsubstituted or substituted with one or more substituents independently selected from the group consisting of cycloalkyl, heterocyclyl, aryl, and heteroaryl;
$R^3$ and $R^4$ are independently selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, —S(O)$_n$—N($R^8$)—$R^8$ where n is 0, 1, or 2, —$NR^8C(O)NR^8R^8$, —$X^1R^8$ where $X^1$ is oxygen, —S(O)$_n$— or —NR$^9$— where n is 0, 1, or 2, or R$^3$, R$^4$ together with the carbon atom pendent thereto, form a cycloalkyl, substituted cycloalkyl, heterocyclyl, substituted heterocyclyl, aryl, substituted aryl, heteroaryl, or substituted heteroaryl;

$R^5$ and $R^6$ are independently selected from the group consisting of hydrogen, halo, alkyl, substituted alkyl, alkoxy, substituted alkoxy, aryl, substituted aryl, heteroaryl, substituted heteroaryl and —X$^2$R$^{10}$ where X$^2$ is oxygen, —S(O)$_n$— or —NR$^{13}$— where n is 0, 1, or 2, or when X$^2$ is —NR$^{13}$—, then R$^{13}$ and R$^{10}$, together with the nitrogen atom to which they are bound, can be joined to form a heterocyclyl or substituted heterocyclyl group;

each $R^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when $X^1$ is —SO— or —SO$_2$—, then $R^8$ is not hydrogen;

$R^9$ and $R^{13}$ are independently selected from the group consisting of hydrogen, alkyl, and aryl; and $R^{1o}$ is selected from the group consisting of alkyl, substituted alkyl, aryl, substituted aryl, heteroaryl, substituted heteroaryl, heterocyclyl and substituted heterocyclyl;

each $R^{11}$ is independently selected from alkyl, benzyl or aryl, or two $R^{11}$ together with the nitrogen atom to which they are attached form a 4-8 membered heterocyclyl or a heteroaryl;

each $R'^2$ is independently selected from the group consisting of alkyl, aryl, heteroaryl, and heterocyclyl, or when two $R'^{12}$ are present, two $R^{12}$ together with the carbon atom to which they are attached form a 4-8 membered heterocyclyl; and $X^3$ is halo.

42. The method of claim 41, wherein Z is O.

43. The method of claim 41, wherein the reaction conditions of steps a) and b) comprise an acid.

44. A method of making a compound of formula VIC or a stereoisomer or mixture of stereoisomers thereof:

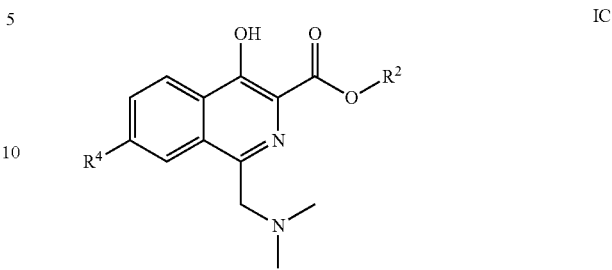

comprising the steps of:
a) contacting a compound of formula IIC with a compound of formula IIIA

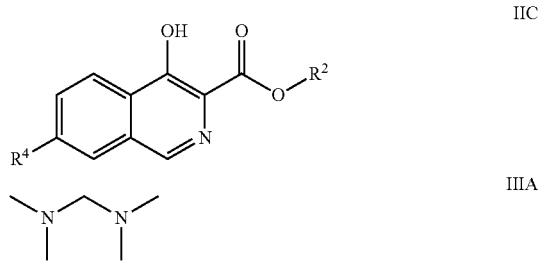

under reaction conditions sufficient to produce a compound of formula IC:

b) contacting a compound of formula IC with a compound of formula VA under reaction conditions sufficient to produce a compound of formula IVC:

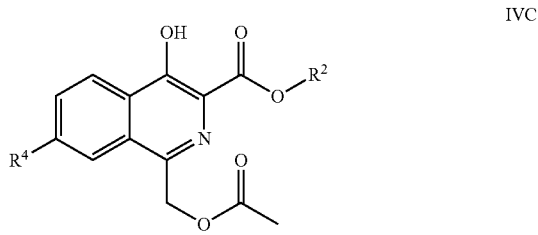

c) optionally converting a compound of formula VIIC:

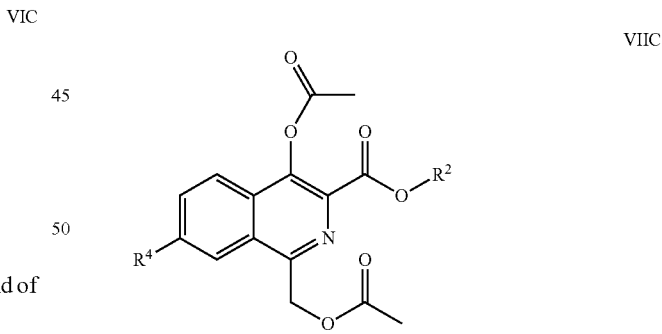

under reaction conditions sufficient to produce a compound of formula IVC; and
d) converting a compound of formula IVC under reaction conditions sufficient to produce a compound of formula VIC;
wherein
$R^2$ is selected from the group consisting of hydrogen and alkyl which is unsubstituted or substituted with one or more substituents independently selected from the group consisting of cycloalkyl, heterocyclyl, aryl, and heteroaryl;

$R^4$ is selected from the group consisting of hydrogen, alkyl, substituted alkyl, cycloalkyl, substituted cycloalkyl, heterocyclyl, substituted heterocyclyl, aryl, substituted aryl, heteroaryl, substituted heteroaryl, halo, hydroxy, cyano, —S(O)$_n$—N(R$^8$)—R$^8$ where n is 0, 1, or 2, —NR$^8$C(O)NR$^8$R$^8$, —X$^1$R$^8$ where X$^1$ is oxygen, —S(O)$_n$— or —NR$^9$— where n is 0, 1, or 2, or R$^3$, R$^4$ together with the carbon atom pendent thereto, form a cycloalkyl, substituted cycloalkyl, heterocyclyl, substituted heterocyclyl, aryl, substituted aryl, heteroaryl, or substituted heteroaryl;

each R$^8$ is independently selected from the group consisting of hydrogen, alkyl, substituted alkyl, aryl, substituted aryl, cycloalkyl, substituted cycloalkyl, heteroaryl, substituted heteroaryl, heterocyclyl and substituted heterocyclyl provided that when X$^1$ is —SO— or —SO$_2$—, then R$^8$ is not hydrogen; and each R$^9$ is selected from the group consisting of hydrogen, alkyl, and aryl.

45. The method of claim 44, further comprising step e) contacting a compound of formula VIC with glycine under reaction conditions sufficient to produce a compound of formula XC:

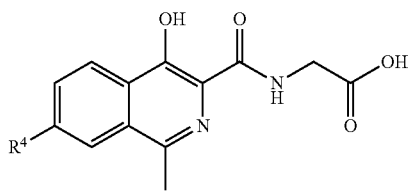

or a stereoisomer or mixture of stereoisomers thereof.

46. A method of making a compound of formula 3c:

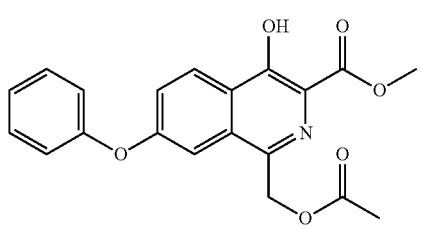

comprising contacting a compound of formula 3b:

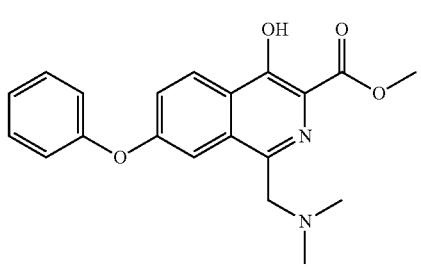

with a compound of formula VA:

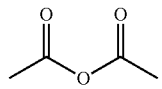

under reaction conditions sufficient to produce a compound of formula 3c.

47. A method of making a compound of formula 3e:

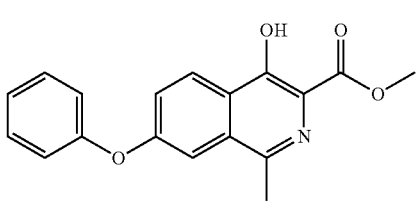

comprising the steps of:

a) contacting a compound of formula 3a with a compound of formula IIIA

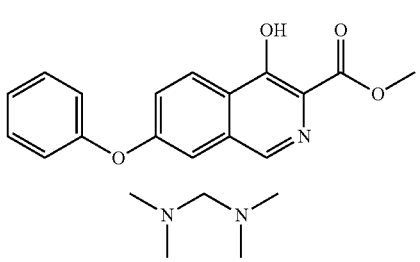

under reaction conditions sufficient to produce a compound of formula 3b:

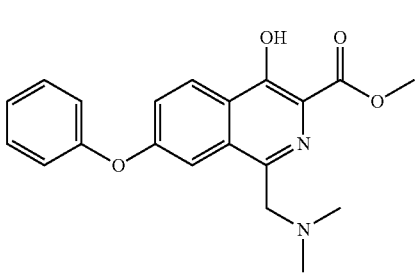

b) contacting a compound of formula 3b with a compound of formula VA

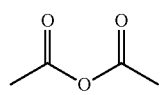

under reaction conditions sufficient to produce a compound of formula 3c:

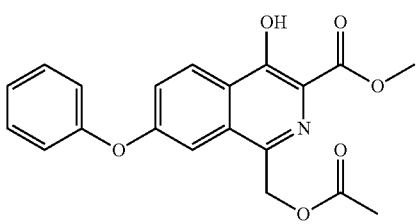

c) optionally converting a compound of formula 3d:

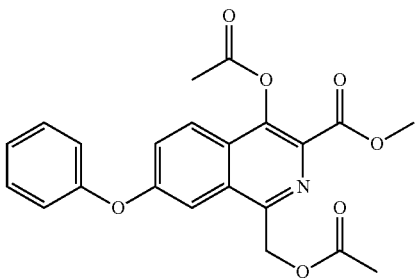

under reaction conditions sufficient to produce a compound of formula 3c; and d) converting a compound of formula 3c under reaction conditions sufficient to produce a compound of formula 3e.

48. The method of claim 47, further comprising step e) contacting a compound of formula 3e with glycine under reaction conditions sufficient to produce a compound of formula 3f:

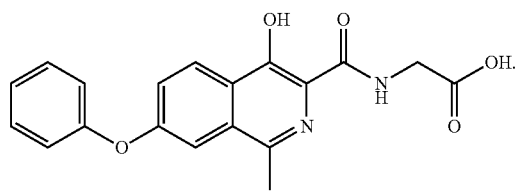

* * * * *